(12) United States Patent
Altieri

(10) Patent No.: US 11,208,478 B2
(45) Date of Patent: Dec. 28, 2021

(54) METHODS OF DETECTING AND TREATING A TUMOR EXPRESSING PT346 PDK1

(71) Applicant: The Wistar Institute of Anatomy and Biology, Philadelphia, PA (US)

(72) Inventor: Dario C. Altieri, Philadelphia, PA (US)

(73) Assignee: THE WISTAR INSTITUTE OF ANATOMY AND BIOLOGY, Philadelphia, PA (US)

( * ) Notice: Subject to any disclaimer, the term of this patent is extended or adjusted under 35 U.S.C. 154(b) by 263 days.

(21) Appl. No.: 16/323,648

(22) PCT Filed: Aug. 4, 2017

(86) PCT No.: PCT/US2017/045513
§ 371 (c)(1),
(2) Date: Feb. 6, 2019

(87) PCT Pub. No.: WO2018/031407
PCT Pub. Date: Feb. 15, 2018

(65) Prior Publication Data
US 2019/0177411 A1 Jun. 13, 2019

Related U.S. Application Data

(60) Provisional application No. 62/371,804, filed on Aug. 7, 2016, provisional application No. 62/400,314, filed on Sep. 27, 2016.

(51) Int. Cl.
| | | |
|---|---|---|
| *C07K 16/28* | (2006.01) |
| *A61K 31/167* | (2006.01) |
| *A61K 31/444* | (2006.01) |
| *A61K 31/496* | (2006.01) |
| *A61K 31/519* | (2006.01) |
| *A61K 31/5383* | (2006.01) |
| *G01N 33/573* | (2006.01) |
| *G01N 33/574* | (2006.01) |
| *A61K 45/06* | (2006.01) |
| *A61K 31/385* | (2006.01) |
| *A61K 31/19* | (2006.01) |
| *A61K 31/4439* | (2006.01) |
| *A61K 31/20* | (2006.01) |
| *A61P 35/00* | (2006.01) |

(52) U.S. Cl.
CPC ............ *C07K 16/28* (2013.01); *A61K 31/167* (2013.01); *A61K 31/19* (2013.01); *A61K 31/20* (2013.01); *A61K 31/385* (2013.01); *A61K 31/444* (2013.01); *A61K 31/4439* (2013.01); *A61K 31/496* (2013.01); *A61K 31/519* (2013.01); *A61K 31/5383* (2013.01); *A61K 45/06* (2013.01); *A61P 35/00* (2018.01); *G01N 33/573* (2013.01); *G01N 33/574* (2013.01); *G01N 33/57407* (2013.01); *G01N 2333/91205* (2013.01); *G01N 2440/14* (2013.01)

(58) Field of Classification Search
CPC ........................................................ C07K 16/28
USPC ........................................................ 424/133.1
See application file for complete search history.

(56) References Cited

U.S. PATENT DOCUMENTS

| | | | |
|---|---|---|---|
| 6,727,284 B2 | 4/2004 | Lopaschuk et al. |
| 8,034,815 B2 | 10/2011 | Danter et al. |
| 8,263,653 B2 | 9/2012 | Shorr et al. |
| 9,221,838 B2 | 12/2015 | Zhang et al. |
| 2009/0209618 A1 | 8/2009 | Dang et al. |
| 2010/0015140 A1 | 1/2010 | Danter |
| 2013/0287763 A1* | 10/2013 | Sathyanarayanan ........................ A61K 39/39558 424/133.1 |
| 2015/0133524 A1 | 5/2015 | Dang et al. |
| 2015/0320754 A1* | 11/2015 | Kutok ............... A61K 31/52 424/278.1 |

FOREIGN PATENT DOCUMENTS

| | | |
|---|---|---|
| WO | 2011077098 A1 | 6/2011 |
| WO | 2011082270 A2 | 7/2011 |

OTHER PUBLICATIONS

Luo et al. (Mol Cancer Ther, 2005, 4(6): 977-986).*
Mann et al., "Diverse mechanisms of inhibition of pyruvate dehydrogenase kinase by structurally distinct inhibitors," Biochimica et Biophysica Acta, 1480: 283-292 (2000).
Rigbolt et al., "System-Wide Temporal Characterization of the Proteome and Phosphoproteome of Human Embryonic Stem Cell Differentiation," ScienceSignaling, 4: rs3 (2011).
International Search Report issued in corresponding International Patent Application No. PCT/US2017/045513 dated Dec. 4, 2017.
Written Opinion issued in corresponding International Patent Application No. PCT/US2017/045513 dated Dec. 4, 2017.
Supplementary European Search Report for European Application No. 17840060 dated Mar. 16, 2020, 3 pages.
European Search opinion for European Application No. 17840060.2 dated Mar. 16, 2020, 4 pages.
Chae et al., "Mitochondrial Akt Regulation of Hypoxic Tumor Reprogramming", Cancer Cell, 2016, vol. 30, pp. 257-272.
Kato et al., "Distinct Structural Mechanisms for inhibition of pyruvate dehydrogenase kinase isoforms by AZD7545, Dichloroacetate, and Radicicol", Structure, 2007, vol. 15, pp. 992-1004.
Hockel, Tumor Hypoxia: Definitions and Current Clinical, Biologic, and Molecular Aspects, J Natl Cancer Inst. 2001, vol. 93, pp. 266-276.
Graeber, Hypoxia-mediated selection of cells with diminished apoptotic potential in solid tumors, Nature, 1996, vol. 379, pp. 88-91.
Tredan, Drug resistance and the solid tumor microenvironment, J Natl Cancer Inst., 2007, vol. 99, pp. 1441-1454.

(Continued)

*Primary Examiner* — Sean E Aeder
(74) *Attorney, Agent, or Firm* — Morgan, Lewis & Bockius LLP

(57) ABSTRACT

Therapeutic treatments of a tumor expressing pT346 PDK1, including glioma expressing pT346 PDK1, are disclosed.

8 Claims, 15 Drawing Sheets

Specification includes a Sequence Listing.

(56) References Cited

OTHER PUBLICATIONS

Cox, The hypoxic cancer secretome induces pre-metastatic bone lesions through lysyl oxidase, Nature, 2015, vol. 522, pp. 106-110.
Keith, HIF1α and HIF2α: sibling rivalry in hypoxic tumour growth and progression, Nat. Rev. Cancer, 2012, vol. 12, pp. 9-22.
Semenza, HIF-1 mediates metabolic responses to intratumoral hypoxia and oncogenic mutations, J Clin Invest, 2013, vol. 123, pp. 3664-3671.
Mazumdar, O2 regulates stem cells through Wnt/βcatenin signaling, Nat Cell Biol., 2010, vol. 12, pp. 1007-1013.
Ravi, Regulation of tumor angiogenesis by p53-induced degradation of hypoxia-inducible factor 1α, Genes Dev., 2000, vol. 14, pp. 34-44.
Gilkes, Hypoxia and the extracellular matrix: drivers of tumour metastasis, Nat Rev Cancer, 2014, vol. 14, pp. 430-439.
Denko, Hypoxia, HIF1 and glucose metabolism in the solid tumor, Nat Rev Cancer, 2008, vol. 8, pp. 705-713.
Kim, HIF-1-mediated expression of pyruvate dehydrogenase kinase: a metabolic switch required for cellular adaptation to hypoxia, Cell Metab., 2006, vol. 3, pp. 177-185.
Patel, The pyruvate dehydrogenase complexes: structure-based function and regulation, J Biol Chem., 2014, vol. 289, pp. 16615-16623.
Gatenby, Why do cancers have high aerobic glycolysis? Nat Rev Cancer, 2004, vol. 4, pp. 891-899.
Papandreou, HIF-1 mediates adaptation to hypoxia by actively downregulating mitochondrial oxygen consumption, Cell Metab. 2006, vol. 3, pp. 187-197.
Therasse, New guidelines to evaluate the response to treatment in solid tumors. European Organization for Research and Treatment of Cancer, National Cancer Institute of the United States, National Cancer Institute of Canada, J Natl Cancer Inst., 2000 vol. 92, pp. 205-216.
Steinberger, Construction of a Combinatorial IgE Library from an Allergic Patient, Phl p. 5, J. Biol. Chem. 1996, vol. 271, pp. 10967-10972.
Latchman et al., PD-L2 is a second ligand for PD-1 and inhibits T cell activation, Nature immunology, 2001, vol. 2, Issue 3, pp. 261-267.
Nitulescu, Akt inhibitors in cancer treatment: The long journey from drug discovery to clinical use (Review), International Journal of Oncology, 2016, vol. 48, pp. 869-885.
Di Cristofori et al. The vacuolar H+ ATPase is a novel therapeutic target for glioblastoma, Oncotarget, 2015, vol. 6, pp. 17514-17531.
Du, Bead-based profiling of tyrosine kinase phosphorylation identifies SRC as a potential target for glioblastoma therapy, Nat Biotechnol., 2009, vol. 27, pp. 77-83.

\* cited by examiner

METHODS OF DETECTING AND TREATING A TUMOR EXPRESSING PT346 PDK1

GOVERNMENT SUPPORT

This invention was made with government support from National Institutes of Health (NIH) grants P30-CA010815, P01-CA140043, R01-CA078810, R01-CA190027 and F32-CA177018. This invention was made with government support from the Office of the Assistant Secretary of Defense for Health Affairs under Award No. W81XWH-13-1-0193. The government has certain rights in the invention.

Sequence Listing Submission via EFS-Web

A computer readable text file, entitled "SequenceListing.txt" created on or about Feb. 6, 2019 with a file size of about 7 kb contains the sequence listing for this application and is hereby incorporated by reference in its entirety.

FIELD OF THE INVENTION

Therapeutic treatments of a subject with a cancer wherein cancer cells expressing pT346 PDK1, such as glioma expressing pT346 PDK1, are disclosed.

BACKGROUND OF THE INVENTION

Hypoxia is a nearly universal feature of tumor growth (Hockel (2001) J Natl Cancer Inst 93, 266-276.), conferring worse disease outcome via protection from apoptosis (Graeber (1996) Nature 379, 88-91.), resistance to therapy (Tredan (2007) J Natl Cancer Inst 99, 1441-1454), and enhanced metastatic competence (Cox (2015) Nature 522, 106-110). This pathway requires the transcriptional activity of hypoxia-inducible factor 1 (HIF1), a master regulator of oxygen homeostasis (Keith (2012) Nat Rev Cancer 12, 9-22) that becomes stabilized upon drops in oxygen pressure by escaping prolyl hydroxylation and proteasome-dependent destruction by the von Hippel-Lindau tumor suppressor (Semenza (2013) J Clin Invest 123, 3664-3671). In turn, nuclear localized HIF1 contributes to oncogene signaling (Mazumdar (2010) Nat Cell Biol 12, 1007-1013), angiogenesis (Ravi (2000) Genes Dev 14, 34-44), cell invasion (Gilkes (2014) Nat Rev Cancer 14, 430-439), and tumor metabolic reprogramming.

In this context, mitochondria are the primary site of hypoxia-induced metabolic reprogramming in tumors (Denko (2008) Nat Rev Cancer 8, 705-713). This response involves HIF1-dependent transcription of mitochondrial pyruvate dehydrogenase kinase (PDK) (Kim (2006) Cell Metab 3, 177-185), which in turn phosphorylates the pyruvate dehydrogenase complex (PDC) on three separate sites (Patel (2014) J Biol Chem 289, 16615-16623). By suppressing the oxidative decarboxylation of pyruvate into acetyl-CoA (Patel (2014) J Biol Chem 289, 16615-16623), an active PDK shuts off oxidative phosphorylation, lowers the production of toxic ROS, and switches tumor bioenergetics towards glycolysis (Denko (2008) Nat Rev Cancer 8, 705-713), a driver of more aggressive disease traits (Gatenby (2004) Nat Rev Cancer 4, 891-899). What has remained unclear, however, is whether HIF1-dependent transcription is the sole mechanism for PDK activation in hypoxia (Kim (2006) Cell Metab 3, 177-185.); (Papandreou (2006) Cell Metab 3, 187-197.), and the existence of other potential regulators of this response has not been widely investigated.

SUMMARY OF THE INVENTION

In one aspect, the present disclosure is related to methods of treating cancer in a human subject in which cancer cells express Pyruvate Dehydrogenase Kinase-1 (PDK1) that is phosphorylated at T346 (pT346 PDK1), the method comprising the step of administering a therapeutically effective dose of a PDK1 inhibitor and/or an Protein Kinase B-beta (AKT) inhibitor to the human subject. In some embodiments, the cancer is a hypoxic tumor. In further embodiments, the cancer may be selected from the group consisting of glioma, prostate cancer and breast cancer. In additional embodiments, the methods may further comprise isolating a biological sample from the human subject and detecting pT346 in the biological sample. In yet additional embodiments, the pT346 PDK1 level in the biological sample is compared to a level of pT346 PDK in normoxic cells. In further embodiments, the biological sample is a tissue biopsy or blood sample. In yet further embodiments, the detecting comprises contacting the biological sample with an anti-pT346 antibody and detecting binding between pT346 PDK1 and the antibody.

In another aspect, the methods of the present disclosure may comprise administering the PDK1 and the AKT inhibitor to the human subject. In some embodiments, the PDK1 inhibitor is selected from the group consisting of:

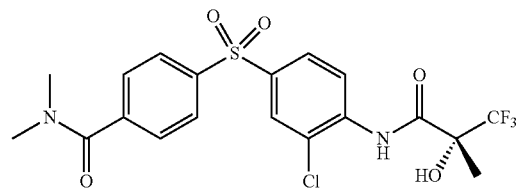 [SMILES: CN(C)C(=O)c1ccc(S(=O)(=O)c2ccc(NC(=O)[C@@](C)(O)C(F)(F)F)c(Cl)c2)cc1]

4-[3-chloro-4-[[(2R)-3,3,3-trifluoro-2-hydroxy-2-methylpropanoyl]amino]phenyl]sulfonyl-N,N-dimethylbenzamide (AZD7545);

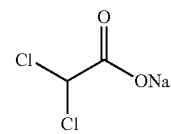

sodium dichloroacetate (Ceresine);

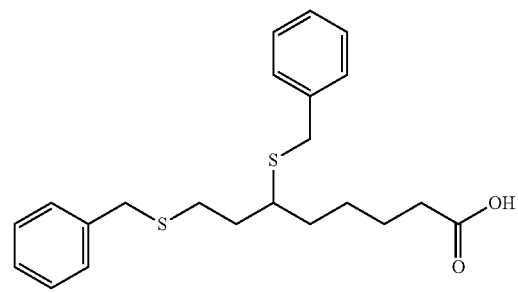 [SMILES: O=C(O)CCCCC(CCSCc1ccccc1)SCc1ccccc1]

6,8-bis(benzylsulfanyl)octanoic acid (CPI613);

lipoic acid; and

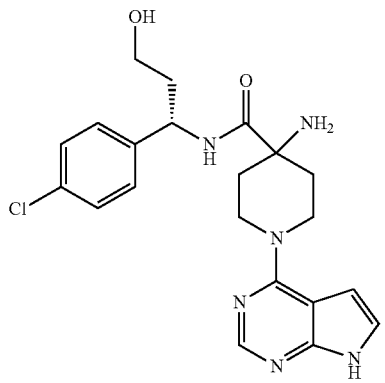 [SMILES: NC1(C(=O)N[C@@H](CCO)c2ccc(Cl)cc2)CCN(c2ncnc3[nH]ccc23)CC1]

4-amino-N-[(1 S)-1-(4-chlorophenyl)-3-hydroxypropyl]-1-(7H-pyrrolo[2,3-d]pyrimidin-4-yl)piperidine-4-carboxamide (AZD5363). In additional embodiments, the AKT inhibitor is selected from the group consisting of:

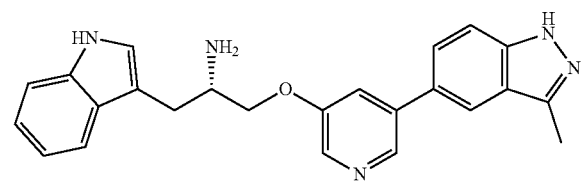 [SMILES: Cc1n[nH]c2ccc(-c3cncc(OC[C@@H](N)Cc4c[nH]c5ccccc45)c3)cc12]

(2s)-1-(1h-Indol-3-Yl)-3-{[5-(3-Methyl-1h-Indazol-5-Yl)pyridin-3-Yl]oxy}propan-2-Amine (A443654);

5-{5-[(2S)-2-amino-3-(1H-indol-3-yl)propoxy]pyridin-3-yl}-3-methyl-1H-indazole;

6-(4-(1-aminocyclobutyl)phenyl)-1-methyl-7-phenyl-1H-pyrido[2,3-b][1,4]oxazin-2(3H)-one 2-(6-(4-(1-aminocyclobutyl)phenyl)-2-oxo-7-phenyl-2,3-dihydro-1H-pyrido[2-,3-b][1,4]oxazin-1yl)acetonitrile;

2-(6-(4-(1-aminocyclobutyl)phenyl)-2-oxo-7-phenyl-2,3-dihydro-1H-pyrido[2-,3-b][1,4]oxazin-1yl)acetonitrile;

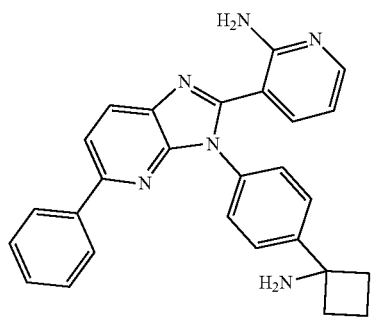 [SMILES: Nc1ncccc1-c1nc2ccc(-c3ccccc3)nc2n1-c1ccc(C2(N)CCC2)cc1]

3-(3-(4-(1-aminocyclobutyl)phenyl)-5-phenyl-3H-imidazo[4,5-b]pyridin-2-yl)pyridin-2-amine (ARQ092);

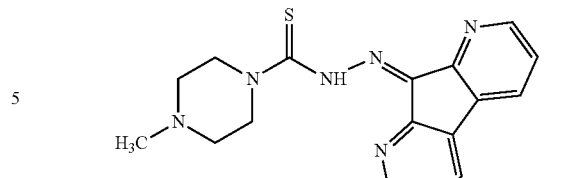

N'-(9H-cyclopenta[1,2-b:4,3-b']dipyridin-9-ylidene)-4-methylpiperazine-1-carbothiohydrazide; and

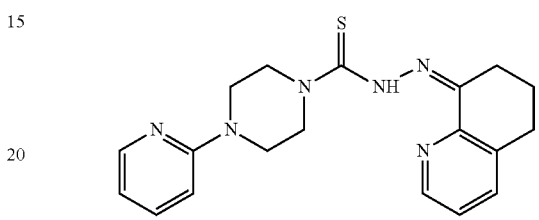

(Z)—N'-(6,7-dihydroquinolin-8(5H)-ylidene)-4-(pyridin-2-yl)piperazine-1-carbothiohydrazide.

In another aspect, the present disclosure is related to methods of detecting the presence of a hypoxic glioma tumor in a human subject comprising isolating a biological sample from the human subject and detecting the presence of pT346 PDK1 in the biological sample. In some embodiments, the presence of pT346 PDK1 indicates the presence of a hypoxic glioma tumor. In additional embodiments, the pT346 PDK1 level in the biological sample is compared to a level of pT346 PDK1 in normoxic cells.

BRIEF DESCRIPTION OF THE DRAWINGS

The foregoing summary, as well as the following detailed description of the invention, will be better understood when read in conjunction with the appended drawings.

FIG. 5 shows requirement of mitochondrial Akt for tumor cell proliferation in hypoxia. A and B: Bioluminescence imaging of immunocompromised mice carrying U251 intracranial GBMs (3 animals/group) expressing luciferase under the control of HIF1-responsive elements (Luc) and mCherry (cell viability) and exposed to a hypoxia-sensitive probe (Hypox). Scans were obtained at days 20 and 34 (A) and fluorescence signals were quantified (B). *, p=0.016-0.057 by Mann-Whitney test. C: Tissue samples from intracranial GBMs as in (A) were harvested at day 34 and analyzed for expression of HIF1α, phosphorylated (p) PDK1 (pT346 Ab) or pPDHE1, by immunohistochemistry. Yellow lines were used to delineate the tumor mass within mice' brain. Scale bar, 100 µm. Asterisks, mitotic cells; Insets (H&E and pPDK1 panels), high-power magnification of mitotic cells. Scale bar, 25 µm. D and E: PC3 cells transfected with control siRNA (Ctrl) or Akt1- or Akt2-directed siRNA (D) or stably transduced with pLKO or PDK1-directed shRNA (E) were analyzed for cell proliferation in normoxia or hypoxia by direct cell counting (n=5). Mean±SEM. *, p<0.001; , p=0.002. F and G: PC3 cells stably transduced with pLKO or PDK1-directed shRNA were analyzed in normoxia or hypoxia for colony formation by crystal violet staining after 10 days (F) and quantified (n=3) (G). Mean±SEM. ns, not significant. ** p=0.003. For all panels, data were analyzed using the two-sided unpaired Student's t test. See also FIG. 13.

Figure 6:
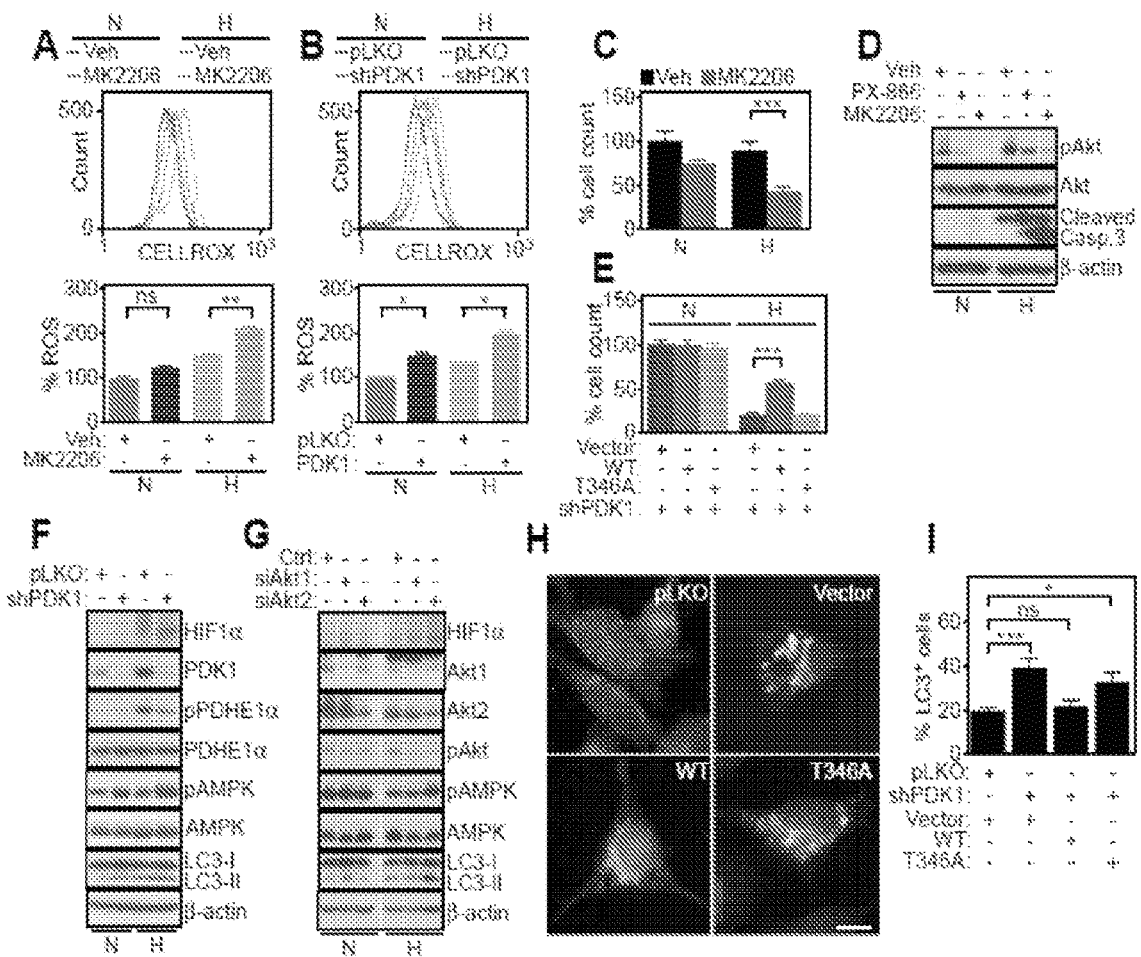

FIG. 6 illustrates mitochondrial Akt regulation of stress signaling in hypoxia. A and B: PC3 cells in normoxia (N) or hypoxia (H) were treated with vehicle (Veh) or MK2206 (1 µM) (A) or transduced with pLKO or PDK1-directed shRNA (B) and analyzed for ROS production by CELLROX Green staining and flow cytometry. Upper panels, representative tracings. Bottom panels, quantification of ROS production under the various conditions tested (n=2). Mean±SD for both datasets. *, p=0.01-0.02; , p=0.004; ns, not significant. C: The experimental conditions are as in (A) and treated cells were analyzed for cell viability by direct cell counting relative to control (n=3). Mean± SEM. *, p<0.0001. D: PC3 cells in normoxia (N) or hypoxia (H) were incubated with vehicle (Veh) or small molecule inhibitors of Akt (MK2206, 1 µM) or PI3K (PX-866, 10 µM) and analyzed by Western blotting. E: PC3 cells stably silenced for PDK1 were reconstituted with vector, WT PDK1 or T346A PDK1 mutant and analyzed for cell viability by direct cell counting relative to control (n=3). Mean±SEM. ***, p=0.0002. F and G: PC3 cells in normoxia (N) or hypoxia (H) were transduced with pLKO or PDK1-directed shRNA (F) or control siRNA (Ctrl) or Akt1- or Akt2-directed siRNA (G), and analyzed by Western blotting. H and I: PC3 cells as in (E) were analyzed for LC3 reactivity by fluorescence microscopy, Scale bars, 10 µm (H), and cells with LC3 puncta (>3) were quantified (n=250-860 cells) (I). Mean±SEM.*, p=0.014; ***, p=0.0005. ns, not significant. For all panels, data were analyzed using the two-sided unpaired Student's t test. See also FIG. 14.

Figure 7:
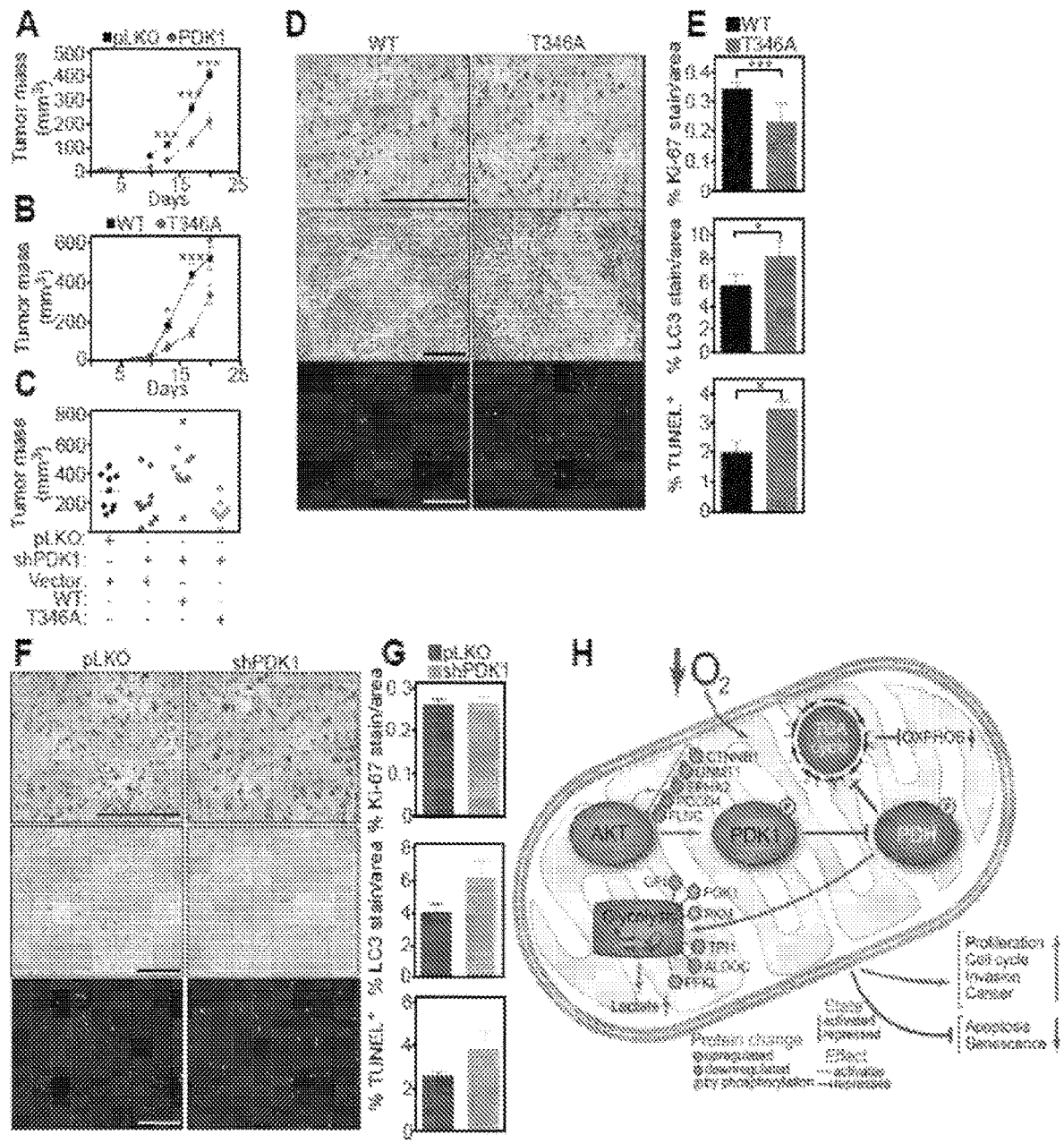

FIG. 7 illustrates mitochondrial Akt-directed hypoxic reprogramming supports tumor growth in vivo. A: PC3 cells transduced with pLKO or PDK1-directed shRNA were injected s.c. in the flanks of male NSG immunocompromised mice (3 animals/group; 2 tumors/mouse) and superficial tumor growth was quantified with a caliper at the indicated time intervals for 20 days. Data were analyzed using the two-sided unpaired Student's t test. Mean± SEM. ***, p<0.0001. B: PC3 cells stably transduced with pLKO or PDK1-directed shRNA were reconstituted with WT PDK1 or T346A PDK1 mutant and injected s.c. in the flanks of immunocompromised mice (5 mice/group; 2 tumors/mouse). Tumor growth in the various groups was quantified at the indicated time intervals for 20 days. Data were analyzed using the two-sided unpaired Student's t test. Mean±SEM. *, p=0.01-0.02; ***, p<0.0001. C: PC3 cells stably transduced with pLKO or PDK1-directed shRNA were reconstituted with vector, WT PDK1 or T346A PDK1 mutant and injected s.c. in immunocompromised mice with determination of tumor growth after 18 days. Each point corresponds to an individual tumor. D and E: Tumors harvested from the animals in (C) were analyzed for histology (D) and cell proliferation (top, Ki-67), autophagy (middle, LC3-II) or apoptosis (bottom, TUNEL) was quantified (E). The statistical analysis of the various groups by ANOVA is as follows: Ki-67, p<0.0001; LC3, p=0.024; TUNEL, p=0.039. Scale bars, 100 µm. F and G: Superficial flank tumors of PC3 cells transduced with control pLKO or PDK1-directed shRNA were harvested after 18 day and processed for immunohistochemistry (F) with quantification of reactivity for Ki-67 (top), LC3 (middle) or TUNEL (bottom) (H). Representative images per each condition are shown. (n=3, 10 images per mouse), Mean±SD. Scale bars, 100 µm. H: Schematic model of a mitochondrial Akt-PDK1-PDHE1 phosphorylation axis in hypoxic tumor reprogramming.

Figure 8:
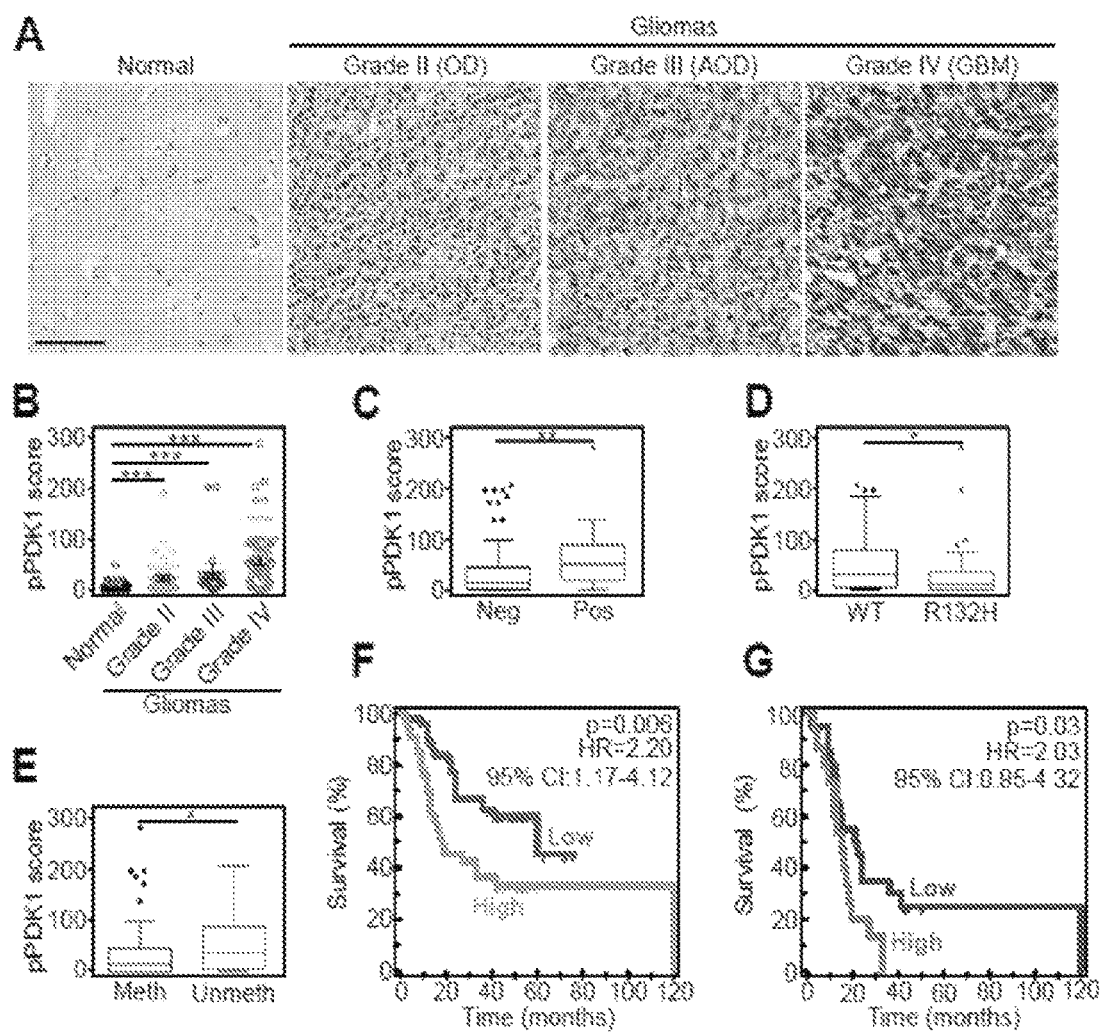

FIG. 8 illustrates mitochondrial Akt phosphorylation of PDK1 is a negative prognostic marker in human gliomas. A: Representative micrographs of immunohistochemical staining of non-neoplastic human brain parenchyma (normal) or grade II-IV gliomas (WHO classification) with PDK1 pT346 Ab. OD, oligodendroglioma; AOD, anaplastic OD; GBM, glioblastoma. Scale bar, 100 µm. B: Quantification of pT346 staining in a series of human brain tumors (n=116) and 85 non-neoplastic brain parenchyma using a two-factor scoring system that considers the percentage of positive cells and the intensity of the staining (pPDK1 score). *, p<0.0001; , p=0.002 by Mann Whitney U-test. Each symbol represents an individual patient. C-E: Differences in pPDK1 score in human brain tumors as in (B) (n=116) according to nuclear HIF1α expression (C, **, p=0.008 by Mann Whitney U-test), IDH1 mutation status (D; *, p=0.02 by Mann Whitney U-test), or MGMT promoter methylation (D; *, p=0.01 by Mann Whitney U-test). Data are presented as Tukey box-and-whisker plots. The bottom and top of the box represent the first and third quartiles, and the band inside the box represents the median (i.e. the $2^{nd}$ quartile). The bottom end of the whisker represents the lowest datum within the 1.5 interquartile range (IQR) of the lower quartile, and the top end of the whisker represents the highest datum within 1.5 IQR of the upper quartile. Outlier data, if any, are represented by single points. F and G: Kaplan-Meier curves were generated with either the complete series of glioma patients (n=116; F) or with GBM cases only (n=61; G) sorted into "Low" or "High" groups according to pPDK1 score. Cutoffs to rank patients in these two categories were generated using ROC curves and the Youden's J statistic. Overall survival curves were compared using the Log-Rank test. HR, Hazard Ratio; CI, Confidence Interval. See also FIG. 15 and Table 3.

Figure 1:
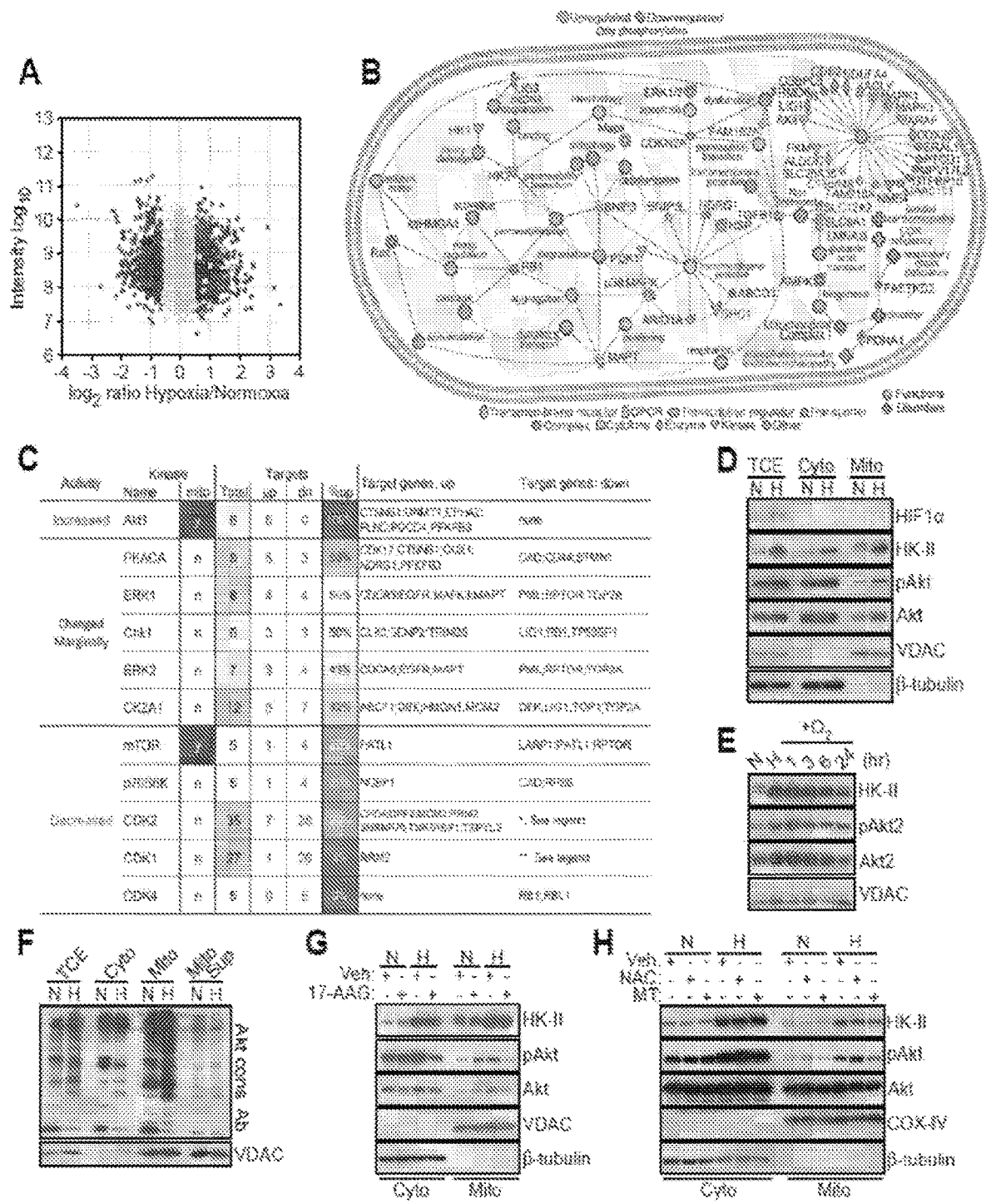
FIG. 1 illustrates mitochondrial phosphoproteome in hypoxia. A: Phosphoproteome of prostate adenocarcinoma PC3 cells in hypoxia versus normoxia. Identified phosphosites met a minimum MaxQuant localization probability of 0.75 and a score difference of 5. Fold changes were calculated from the normalized Heavy/Light SILAC ratio. Six Akt target proteins showing increased phosphorylation in hypoxia are indicated. Grey, not significant; red, upregulated; blue, downregulated; yellow squares, Akt targets. B: Ingenuity pathway analysis of mitochondrial phospho- and global proteome in hypoxia. C: Kinases for which at least 5 known targets showed significant changes in phosphorylation in hypoxic versus normoxic conditions as in A. Up, upregulation; Dn, downregulation. *, The modulated genes are: ARID1A; HIST1HIE; HMGA1; LARP1; LIG1; LIG3; LMNB2; LRCH3; LRWD1; MARCKS; MED1; MKI67; NCL; NPM1; NUCKS1; PDS5B; PTPN2; RB1; RBL1; RBL2; SAMHD1; SETDB1; TERF2; VIM. **, The modulated genes are: DUT; EEF1D; HIST1HIE; HMGA1; IRS2; LIG1; LIG3; LMNA; LMNB1; MAP4; NOLC1; NPM1; NUCKS1; PDS5B; PTPN2; RB1; SAMHD1; TCOF1; TOP2A; TPX2; VIM. D: PC3 cells in normoxia (N) or hypoxia (H) were fractionated in cytosol (Cyto) or mitochondrial (Mito) extracts and analyzed by Western blotting. pAkt, phosphorylated Akt (Ser473). TCE, total cell extracts. E: PC3 cells in hypoxia (H) were exposed to reoxygenation (O$_2$) for the indicated time intervals and analyzed by Western blotting. N, normoxia. F: The indicated subcellular fractions isolated from normoxic (N) or hypoxic (H) PC3 cells were analyzed with an antibody to the Akt consensus phosphorylation site RxRxxS/T (Akt cons Ab) by Western blotting. Mito Sup, supernatant of mitochondrial extracts after preclearing with Akt cons Ab. G: PC3 cells in normoxia (N) or hypoxia (H) were treated with vehicle (Veh) or Hsp90 small molecule inhibitor 17-AAG (5 µM for 6 hr), and cytosolic (Cyto) or mitochondrial (Mito) extracts were analyzed by Western blotting. H: PC3 cells in normoxia (N) or hypoxia (H) were treated with vehicle (Veh), the antioxidant N-acetyl cysteine (NAC, 1 mM) or mitochondria-specific ROS scavenger, MitoTempo (MT, 25 µM), and subcellular fractions were analyzed by Western blotting. See also FIG. 9.
Figure 9:
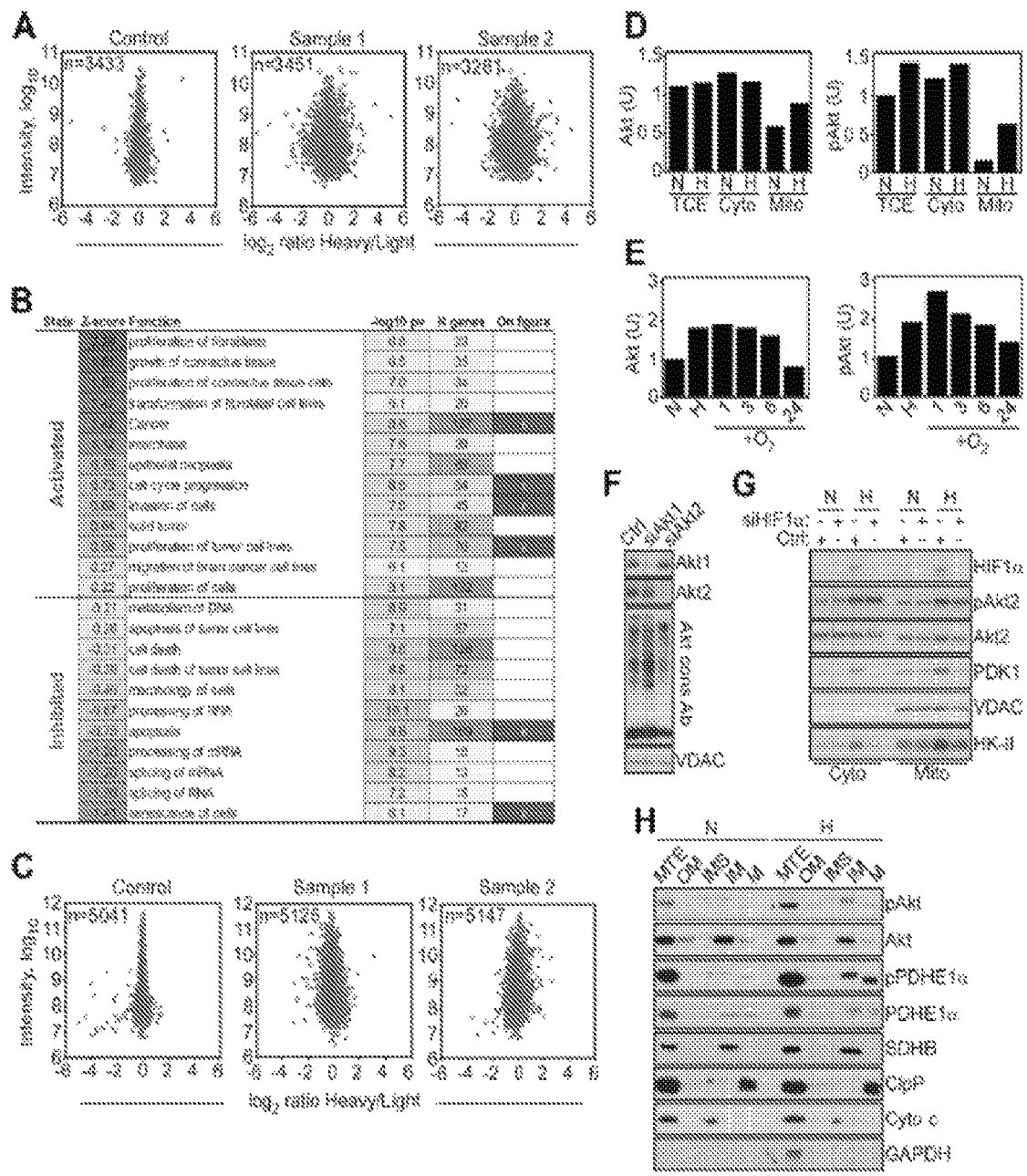

FIG. 9, related to FIG. 1, illustrates additional data regarding mitochondrial phosphoproteome in hypoxia. A: PC3 cells were subject to SILAC labeling and representative heavy/light ratio versus intensity plots of phosphosites identified following phosphopeptide enrichment in control (normoxia/normoxia), experimental sample 1 (normoxia/hypoxia) and experimental sample 2 (hypoxia/normoxia) are shown. "n", total number of unique phosphosites quantitated in the dataset. B: Functions enriched among proteins whose phosphorylation or expression in PC3 cells are modulated by hypoxia as determined by Ingenuity Pathway Analysis (IPA). Z-scores are calculated by IPA based on direction of change of involved genes, and indicate predicted downstream changes in activation state (activated or inhibited) of the enriched functions. Additional information shows function enrichment significance (pv) and number of genes from the functions that showed expression changes (N genes). The last column indicates enriched functions used in the model shown in item F in FIG. 7. C: PC3 cells were subject to SILAC labeling and representative heavy/light ratio versus intensity plots of proteins identified without phosphopeptide enrichment in control and experimental sample 1 and experimental sample 2 as in (A) are shown. "n", total number of unique proteins quantitated in the dataset. D and E: Densitometric quantification of Akt and phosphorylated (p) Akt levels in individual subcellular fractions in normoxia (N) or hypoxia (H) (D) or in a time course after hypoxia and reoxygenation (+O2) (E). PC3 cells were used in both experiments. TCE, total cell extracts; Cyto, cytosol; Mito, mitochondria. U, arbitrary units. F: PC3 cells in hypoxia were transfected with control non-targeting siRNA (Ctrl) or Akt1- or Akt2-directed siRNA and mitochondrial extracts were analyzed by Western blotting. G: PC3 cells in normoxia (N) or hypoxia (H) were transfected with control non-targeting siRNA (Ctrl) or HIF1α-directed siRNA, and cytosol (Cyto) or mitochondrial (Mito) fractions were analyzed by Western blotting. H: Mitochondrial extracts (MTE) from PC3 cells in normoxia (N) or hypoxia (H) were fractionated in individual submitochondrial fractions including outer membrane (OM), inter-membrane space (IMS), inner membrane (IM) and matrix (M) and analyzed by Western blotting. GAPDH was a cytosolic marker.

Figure 2:
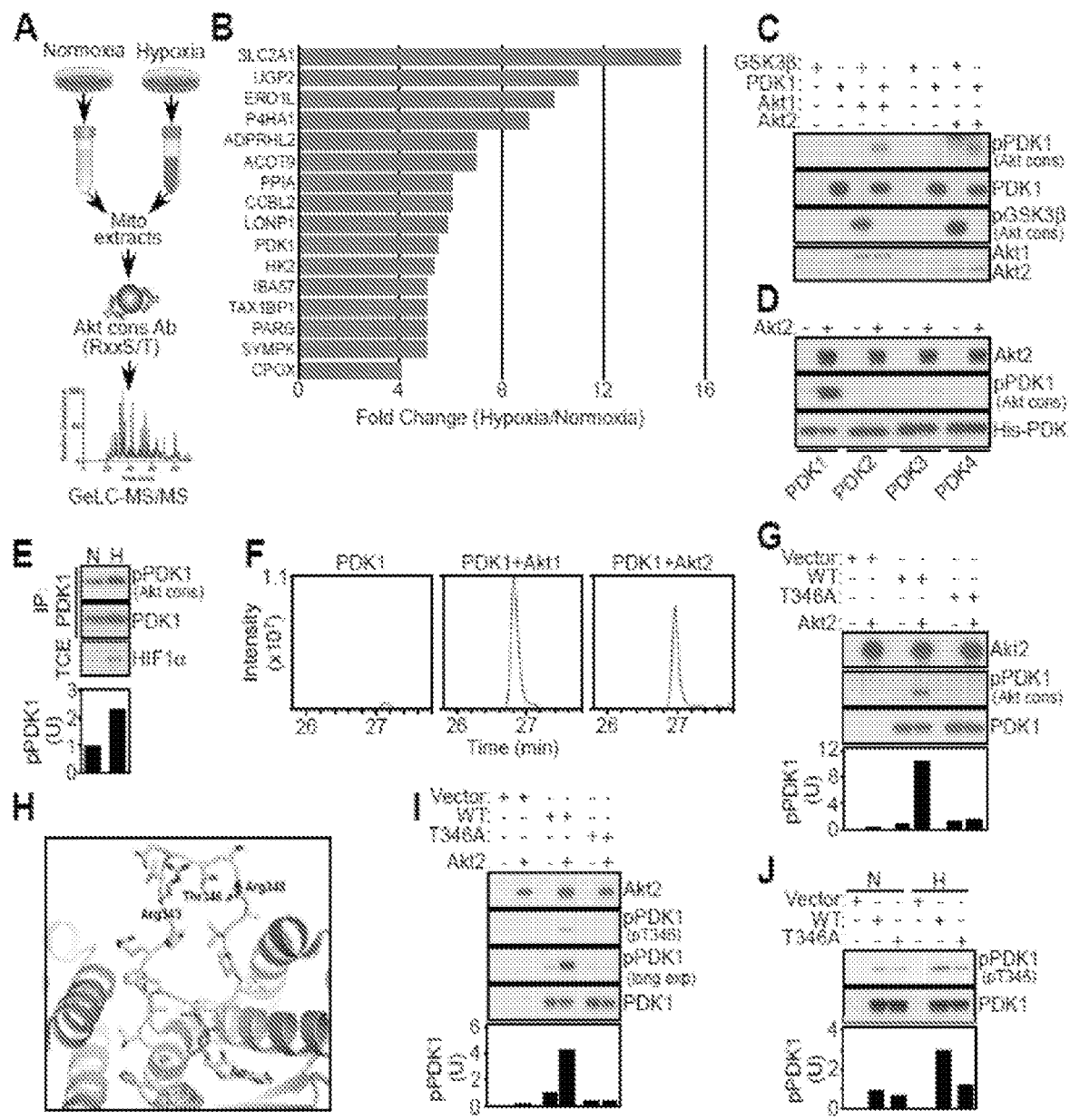
FIG. 2 illustrates Mitochondrial Akt phosphorylation of PDK1. A: Schematic diagram for the identification of a mitochondrial Akt phosphoproteome in hypoxic versus normoxic PC3 cells. B: Mitochondrial proteins reacting with Akt cons Ab showing differential expression in hypoxic versus normoxic PC3 cells. C: Recombinant PDK1 or GSK3α was mixed in a kinase assay with active Akt1 or Akt2, and phosphorylated bands were detected with Akt cons Ab by Western blotting. D: The indicated PDK isoforms were mixed in the presence or absence of active Akt2 in a kinase assay and phosphorylated bands were detected with Akt cons Ab, by Western blotting. E: PC3 cells in normoxia (N) or hypoxia (H) were immunoprecipitated (IP) with an antibody to PDK1 followed by Western blotting. HIF1α reactivity (bottom) was used as a marker of hypoxia. TCE, total cell extracts. Bottom, densitometric quantification of phosphorylated (p) PDK1 bands. U, arbitrary units. F: Extracted ion chromatogram of the PDK1 phosphorylated T346 chymotryptic peptide (STAPRPRVEpTSRAVPL, m/z 908.9751) resulting from incubation with or without active Akt1 or Akt2 in a kinase assay. G: PC3 cells were transfected with vector or Flag-tagged wild type (WT) PDK1 or T346A PDK1 mutant, immunoprecipitated with an antibody to Flag and immune complexes were mixed with active Akt2 in a kinase assay followed by Western blotting with Akt cons Ab. Bottom, densitometric quantification of phosphorylated (p) PDK1 bands. U, arbitrary units. H: Molecular dynamics simulation of the structure of PDK1 (ribbon) with stick representation of residues 336-356 comprising the "ATP lid". The ATP molecule is derived from the structure of PDK3-L2-ATP (PDB code 1Y8P) superimposed onto the structure of PDK1. The predicted location of Thr346 as well as Arg343 and Arg348 is shown. I: The experimental conditions are as in (G) except that Flag-PDK1 immune complexes mixed with active Akt2 in a kinase assay were analyzed with phospho-specific pT346 Ab by Western blotting. Exp., exposure. Bottom, densitometric quantification of phosphorylated (p) PDK1 bands. U, arbitrary units. J: Flag-PDK1 immune complexes as in (G) were precipitated from PC3 cells in normoxia (N) or hypoxia (H) and analyzed with pT346 Ab by Western blotting. p, phosphorylated. Bottom, densitometric quantification of pPDK1 bands. U, arbitrary units. See also FIG. 10 and Table 2.
Figure 10:
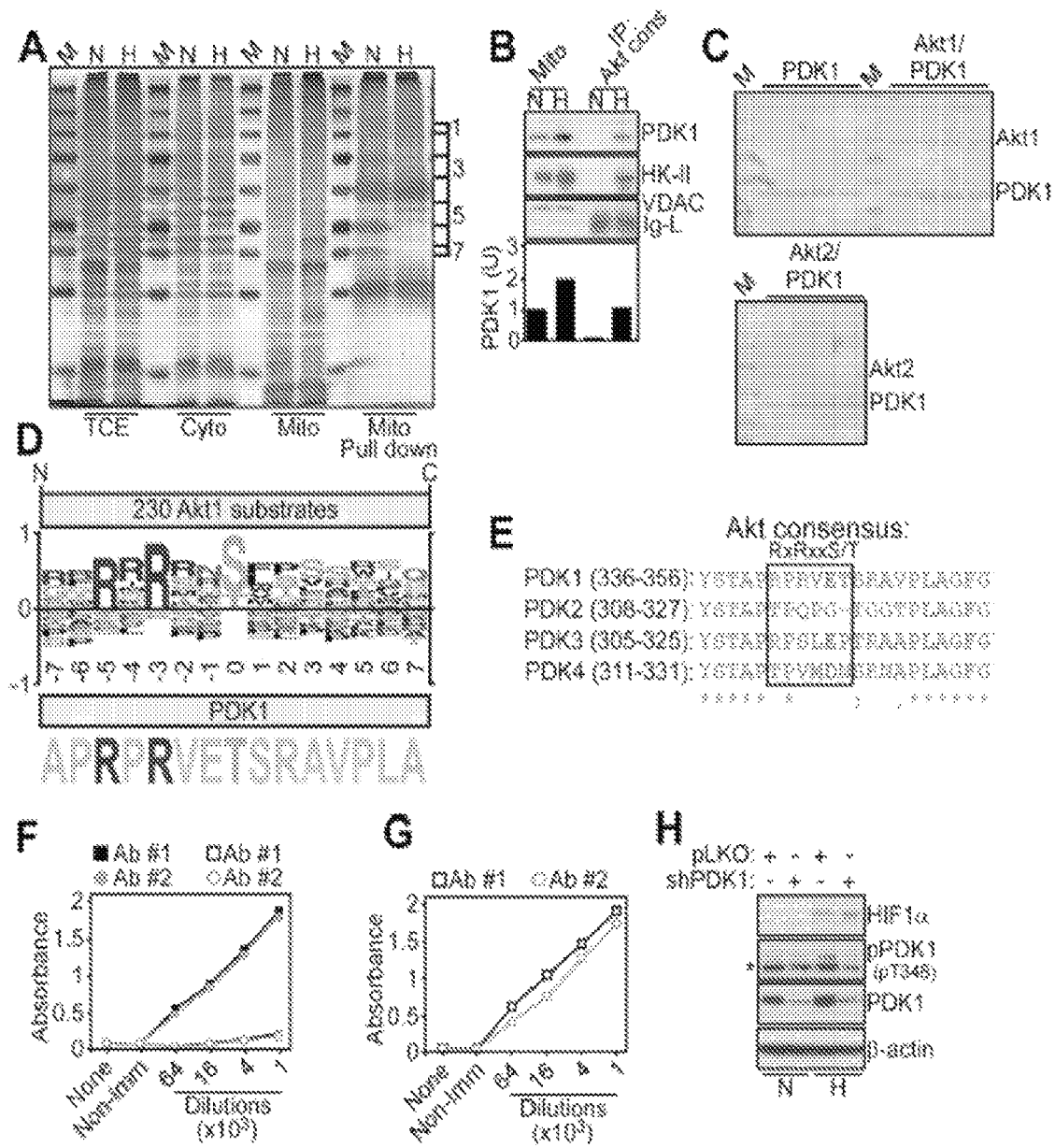

FIG. 10, related to FIG. 2, illustrates additional data regarding mitochondrial Akt phosphorylation of PDK1 in hypoxia. A: PC3 cells in normoxia (N) or hypoxia (H) were fractionated in cytosol (Cyto) or mitochondrial (Mito) extracts. Mitochondrial extracts were incubated with an antibody to Akt consensus phosphorylation site RxRxxS/T and pulldown proteins (Mito pull down) were identified by SDS gel electrophoresis and silver staining. The contiguous gel section containing protein bands differentially enriched between the samples (brackets) was cut into seven slices, digested with trypsin and subjected to 1D proteomics analysis. M, molecular weight markers. TCE, total cell extracts. B: Mitochondrial (Mito) extracts were immunoprecipitated (IP) with Akt cons Ab, and analyzed by Western blotting. IgL, Ig light chain. Bottom, densitometric quantification of PDK1 bands. U, arbitrary units. C: Recombinant PDK1 was incubated with active Akt1 or Akt2, and proteins were analyzed by Coomassie blue staining. M, molecular weight markers. D: Sequence alignment of Akt consensus phosphorylation site in 230 Akt substrates and matching protein sequence of PDK1 phosphorylation site. E: Sequence alignment of human PDK isoforms. An Akt consensus phosphorylation sequence is boxed. Amino acid numbers are indicated in parentheses. F: ELISA reactivity of two independent rabbit phospho-specific antibodies (pT346 Ab#1 and Ab#2) against the PDK1 phosphorylated sequence (APRPRVEpTSRAVPL, solid symbols) and the non-phosphorylated sequence (APRPRVETSRAVPL, open symbols). Representative experiments. G: Two independent rabbit antisera generated against the non-phosphorylated PDK1 peptide sequence as in (F) were tested at the indicated dilutions by ELISA. Non-Imm, non-immune rabbit serum. Representative experiments. H: PC3 cells in normoxia (N) or hypoxia (H) were transduced with control pLKO or PDK1-directed shRNA and analyzed by Western blotting. p, phosphorylated. *, non-specific.

Figure 3:
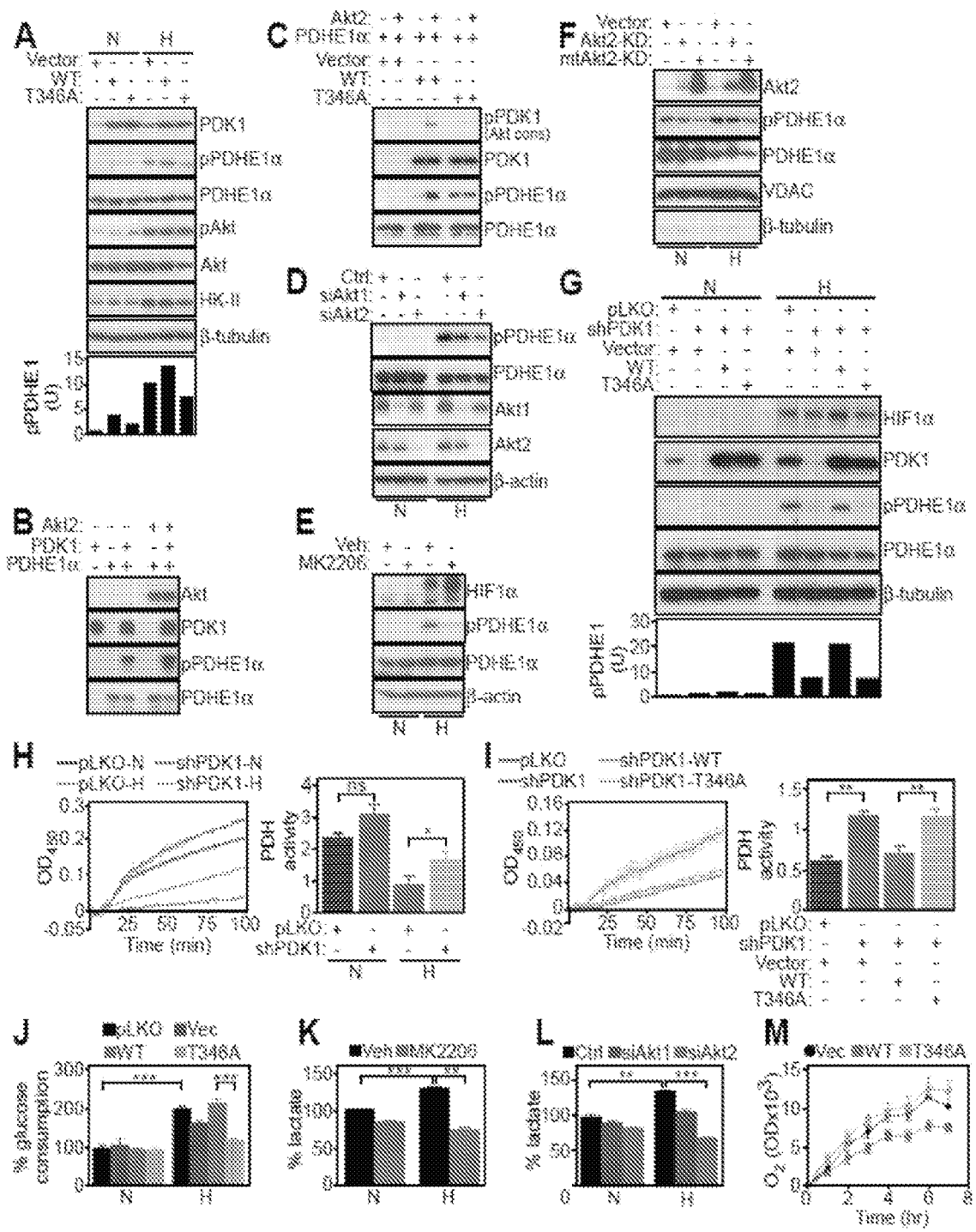
FIG. 3 illustrates mitochondrial Akt-PDK1-PDHE1 phosphorylation axis in hypoxia. A: PC3 cells in normoxia (N) or hypoxia (H) were transfected with vector, WT PDK1 or T346A PDK1 mutant and analyzed by Western blotting. Bottom, densitometric quantification of phosphorylated (p) PDHE1 bands. U, arbitrary units. B: The indicated recombinant proteins were mixed in a kinase assay and analyzed by Western blotting. C: PC3 cells transfected with vector or the indicated Flag-tagged WT PDK1 or T346A PDK1 mutant were immunoprecipitated (IP) with an antibody to Flag, and immune complexes were mixed in a kinase assay with recombinant Akt2 and PDHE1 followed by Western blotting. D: PC3 cells in normoxia (N) or hypoxia (H) were transfected with control siRNA (Ctrl) or siRNA to Akt1 or Akt2, and analyzed by Western blotting. E: PC3 cells in normoxia (N) or hypoxia (H) were treated with vehicle control (Veh) or a small molecule Akt inhibitor, MK2206 (1 µM), and analyzed by Western blotting. F: PC3 cells in normoxia (N) or hypoxia (H) were transfected with vector, Akt-kinase dead (Akt-KD) or mitochondrial-targeted Akt-KD (mtAkt-KD) mutant, and mitochondrial extracts (Mito) were analyzed by Western blotting. G: PC3 cells in normoxia (N) or hypoxia (H) were transduced with pLKO or PDK1-directed shRNA, reconstituted with vector, WT PDK1 or T346A PDK1 mutant cDNA and analyzed by Western blotting. Bottom, densitometric quantification of phosphorylated (p) PDHE1 bands. U, arbitrary units. H: PC3 cells transduced with pLKO or PDK1-directed shRNA were analyzed for PDH activity in normoxia (N) or hypoxia (H) conditions. Left, representative tracings (n=4). Right, quantification of PDH activity. ns, not significant. Mean±SEM. *, p=0.03. I: PC3 cells in hypoxia were transduced with PDK1-directed shRNA, reconstituted with vector, WT PDK1 or T346A PDK1 mutant cDNA and analyzed for PDH activity. Left, representative tracings (n=3). Right, quantification of PDH activity. Mean±SEM. , p=0.009. J: PC3 cells transduced with pLKO or PDK1-directed shRNA were reconstituted with vector, WT PDK1 or T346A PDK1 cDNA and analyzed for glucose consumption (n=4). Mean± SEM. *, p<0.0002. K: PC3 cells in normoxia (N) or hypoxia (H) were treated with vehicle control (Veh) or Akt inhibitor, MK2206 (1 µM), and analyzed for lactate production (n=3). Mean±SEM. , p=0.001-0.004; *, p=0.0005-0.0009. L: PC3 cells in normoxia (N) or hypoxia (H) were transfected with control siRNA (Ctrl) or siRNA to Akt1 or Akt2 and analyzed for lactate production (n=2). Mean± SD. , p=0.004; *, p=0.0005. M: PC3 cells stably silenced for PDK1 were transfected with vector (Vec), WT PDK1 or T346A PDK1 mutant, and analyzed for oxygen (O$_2$) consumption (n=3). Mean±SEM. For all panels, data were analyzed using the two-sided unpaired Student's t tests. See also FIG. 11.
Figure 11:
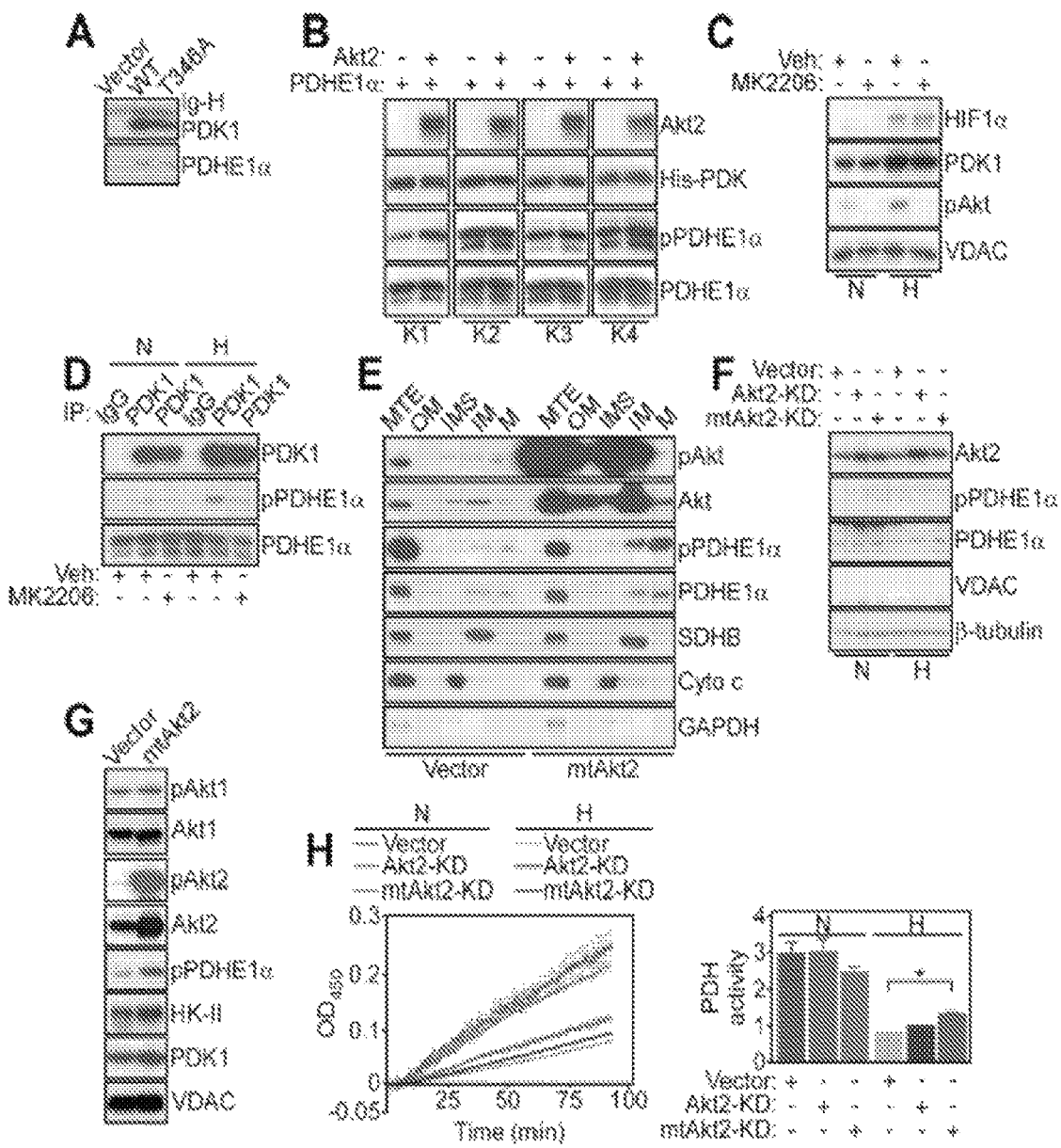

FIG. 11, related to FIG. 3, illustrates additional data regarding mitochondrial Akt regulation of PDK1. A: PC3 cells were transfected with vector or Flag-WT or -T346A PDK1 cDNA, immunoprecipitated with an antibody to Flag, and analyzed by Western blotting. B: Recombinant His-tagged PDK isoforms (K1, K2, K3, and K4) were mixed with active Akt2 plus PDHE1α in a kinase assay and phosphorylated bands were analyzed by Western blotting. C: PC3 cells in normoxia (N) or hypoxia (H) were treated with vehicle (Veh) or small molecule Akt inhibitor, MK2206 (1 μM) and analyzed by Western blotting. TCE, total cell extracts. p, phosphorylated. D: PC3 cells in normoxia (N) or hypoxia (H) were treated with vehicle (Veh) or MK2206 (1 μM), immunoprecipitated (IP) with IgG or an antibody to PDK1, and immune complexes were mixed with PDHE1 in a kinase assay, with analysis of phosphorylated bands by Western blotting. E: PC3 cells were transfected with vector or mitochondrial-targeted Akt2 (mtAkt2) and submitochondrial fractions comprising outer membrane (OM), inter-membrane space (IMS), inner membrane (IM) or matrix (M) were analyzed by Western blotting. MTE, total mitochondrial extracts. F: PC3 cells in normoxia (N) or hypoxia (H) were transfected with vector, Akt2 kinase-dead (KD) or mitochondrial (mt)-targeted Akt2-KD cDNA and cytosolic fraction was analyzed by Western blotting. G: PC3 cells were transfected with vector or mitochondrial-targeted Akt2 (mtAkt2) cDNA and mitochondrial fraction was analyzed by Western blotting. p, phosphorylated. H: PC3 cells in normoxia (N) or hypoxia (H) were transfected with Akt2-kinase dead (KD) or mitochondrial-targeted Akt2-KD cDNA, and continuously analyzed for PDH activity at the indicated increasing time intervals. Representative tracings are shown. Right, quantification of PDH activity under the various conditions tested (n=3). *, p=0.03. Mean±SEM.

Figure 4:
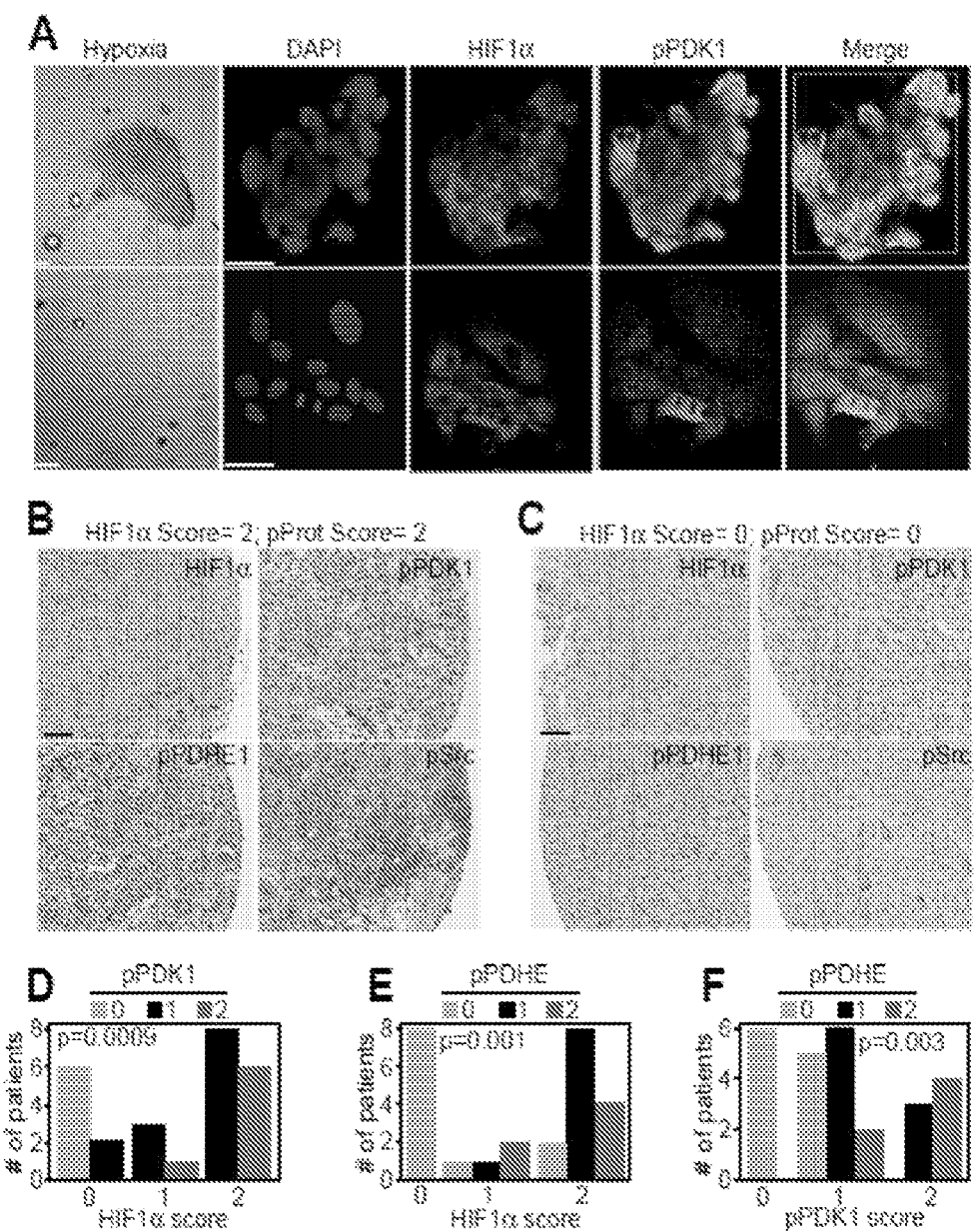
FIG. 4 illustrates mitochondrial Akt-PDK1 phosphorylation, in vivo. A: GBM neurospheres (top) or differentiated GBM cultures (bottom) were stained for DNA (DAPI), HIF1 α, pT346-phosphorylated PDK1, or hypoxia (hypoxia-sensitive probe). Merged images of nuclear-localized HIF1α in hypoxic neurospheres (by velocity mask) are indicated (Merge). Yellow box, Velocity analysis to identify cells with nuclear HIF1α in each single z-stack. Scale bar, 20 µm. B and C: Immunohistochemical staining of primary, patient-derived GBM samples with high (≥2) (B) or low (0) (C) score for HIF1α and phosphorylated protein (pProt) expression. Scale bar, 100 µm. p, phosphorylated. D-F: Quantitative immunohistochemical correlation of patient-derived GBM samples (n=24) or grade II gliomas (n=2) for HIF1α expression and pPDK1 (D), or pPDHE1 (E), or between pPDK1 and pPDHE1 (F). Four tissue microarray (TMA) cores/patient. The scoring is as follows: 0, no staining; 1, staining in at least one TMA core; 2, staining in ≥2 TMA cores. The individual p values per each analysis are indicated (Chi-Square test). See also FIG. 12 and Table 1.
Figure 12:
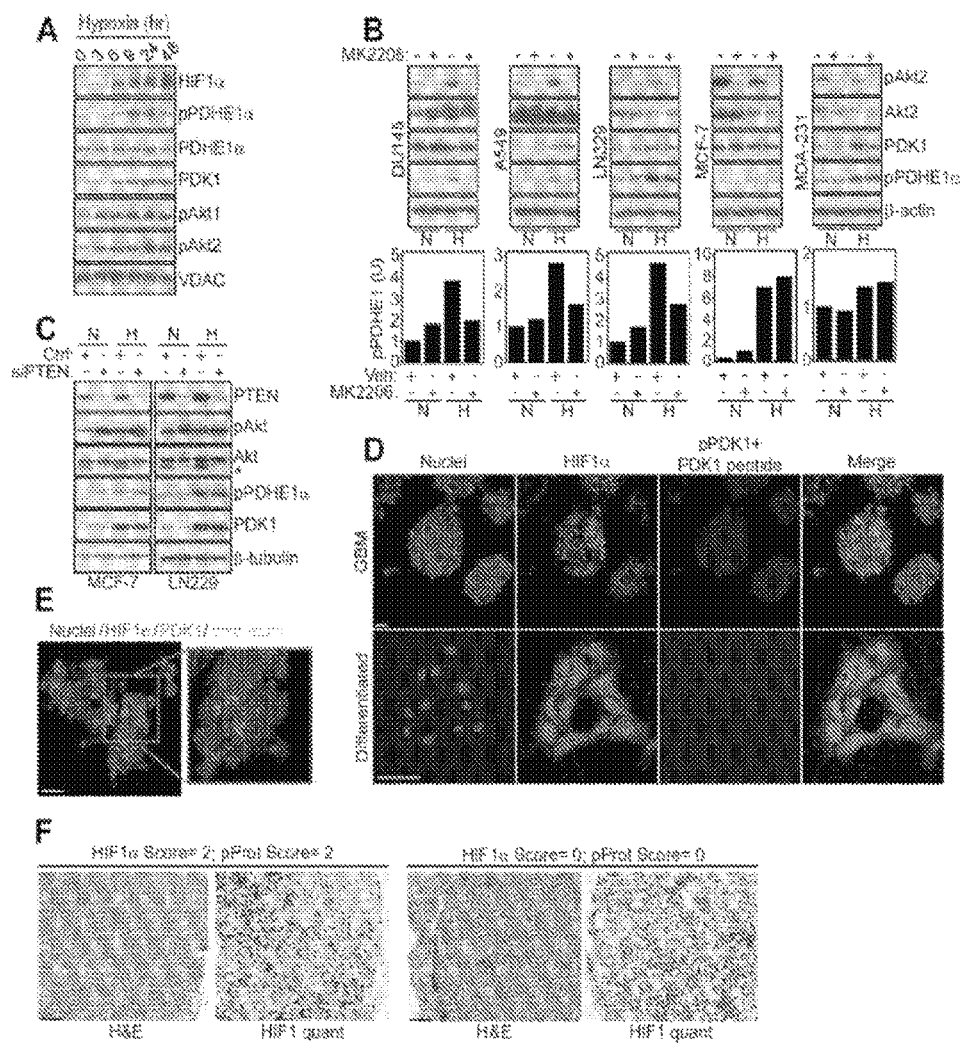

FIG. 12, related to FIG. 4, illustrates additional data regarding mitochondrial Akt-PDK1 regulation of tumor metabolic reprogramming. A: PC3 cells in hypoxia were analyzed at the indicated time intervals by Western blotting. B: The indicated tumor cell types in normoxia (N) or hypoxia (H) were treated with vehicle (−) or MK2206 (+) and analyzed by Western blotting. Bar graphs, densitometric quantification of phosphorylated (p) PDHE1 bands under the various conditions tested. C: The indicated MCF-7 or LN229 cells in normoxia (N) or hypoxia (H) were transfected with control non-targeting siRNA (Ctrl) or PTEN-directed siRNA, and analyzed by Western blotting. *, PTEN band. D and E: Primary, patient-derived glioblastoma (GBM) neurospheres enriched in stem cells (top) or differentiated GBM cultures maintained as monolayers and depleted in stem cells (bottom) were stained for Nuclei (Hoechst), HIF1α, or T346 phosphorylation in PDK1 (pT346 Ab) after pre-absorption of pT346 Ab with the corresponding immunizing peptide (C)APRPRVEpTSRAV-PL(A). Representative image merging analysis (Merge) revealed cytosolic localization of HIF1α in differentiated GBM cultures (D). A control z-stack image of a neurosphere without detectable nuclear HIF1α expression (as determined by Velocity mask) and color-coded reactivity is shown (E). Scale bar, 20 μm. F: Primary, patient-derived GBM tissue samples with high (≥2) or low (0) score for expression of HIF1α and phosphorylated proteins (pProt) were analyzed by immunohistochemistry. H&E, hematoxylin/eosin. HIF1α quant, quantification of nuclear HIF1α localization by Genie Histology Pattern Recognition software. Scale bar, 100 μm.

Figure 5:
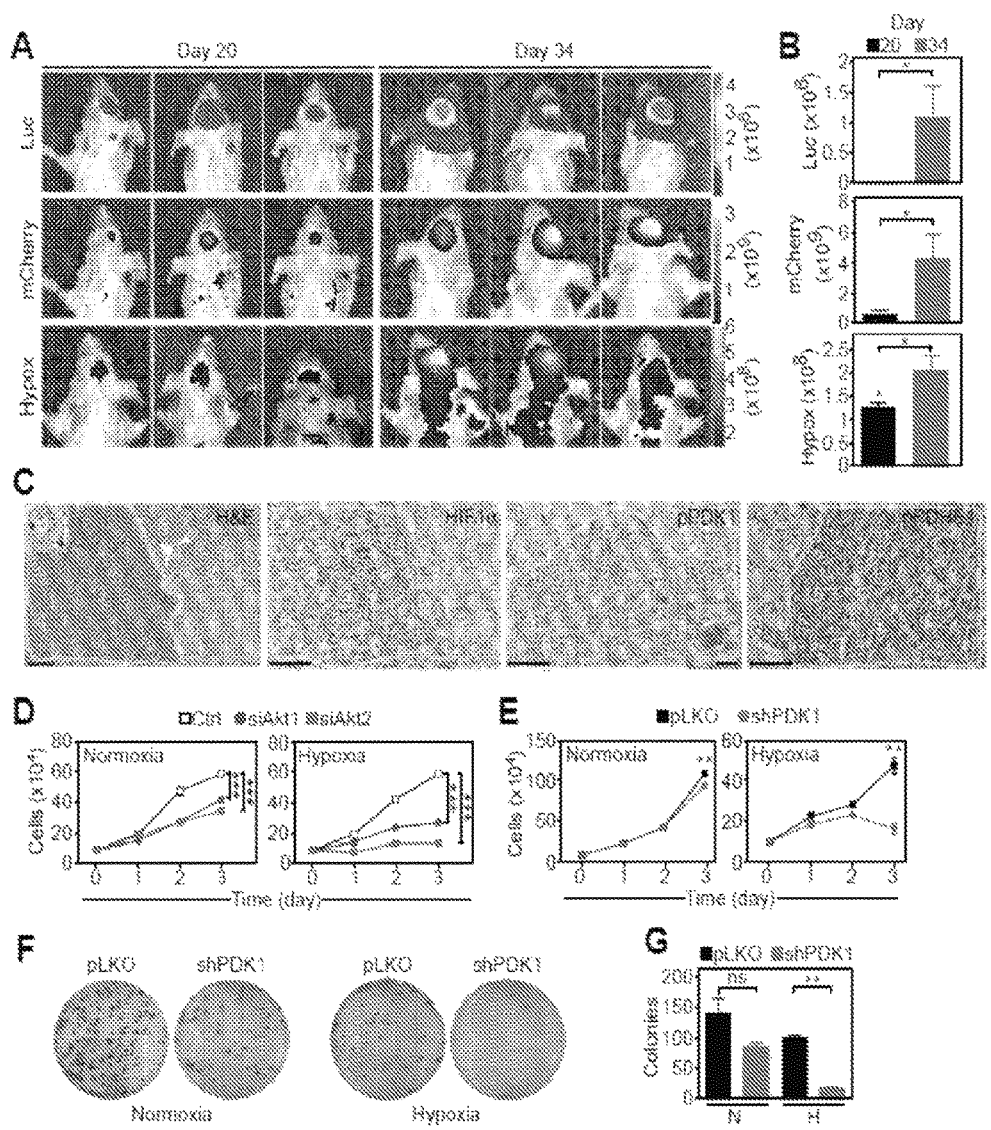
Figure 13:
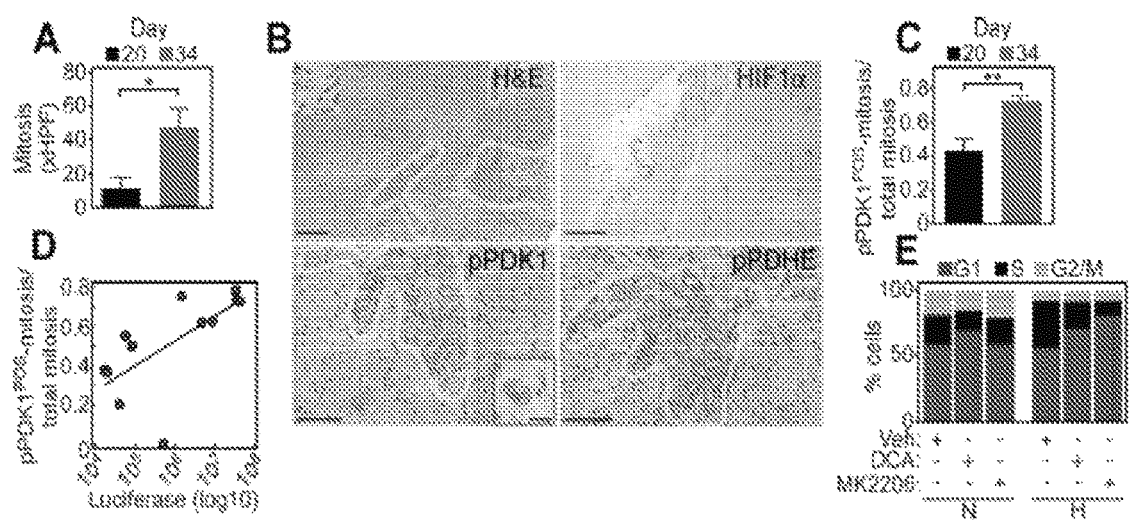

FIG. 13, related to FIG. 5, illustrates additional data regarding mitochondrial Akt signaling supports tumor growth in hypoxia in vivo. A: Human intracranial GBM samples (U251 cells) grown in immunocompromised mice were harvested at the indicated time intervals after stereotactic injection, and the number of mitotic cells was quantified. HPF, high-power microscopy field (n=6-7). Mean±SEM. *, p=0.01. B: Human intracranial GBM samples as in (A) were harvested at day 20 after stereotactic injection of U251 cells in immunocompromised mice, and analyzed for expression of HIF1α, phosphorylated PDK1 (pT346 Ab) or phosphorylated PDHE1α by immunohistochemistry. H&E, hematoxylin and eosin. Yellow lines were used to delineate the tumor mass within mice brain. Scale bar, 100 µm. Asterisk, mitotic cell positive for pPDK1 expression. Insets, high-power image of pPDK1-positive mitotic cells (pPDK1 panel) or nuclear Ki-67 expression (H&E panel). Scale bar, 25 µm. C: Quantification of mitotic cells expressing phosphorylated PDK1 (pT346 Ab) in intracranial GBM harvested from immunocompromised mice at the indicated time intervals (n=5-7). Mean±SEM. **, p=0.002. D: Intracranial GBM samples as in (A) were analyzed for correlation between HIF1α luciferase activity and the number of PDK1-phosphorylated mitotic cells (pT346 Ab). p=0.72, 95% C.I.=0.1-0.9; p=0.02. Each point corresponds to an individual tumor (n=12). E: PC3 cells in normoxia (N) or hypoxia (H) were treated with vehicle (Veh) or small molecule antagonists of PDK1 (DCA, 10 mM) or Akt (MK2206, 5 µM) and analyzed for DNA content by propidium iodide staining and flow cytometry. The percentage of cells in the various cell cycle phases is indicated per each condition. Representative experiment.

Figure 14:
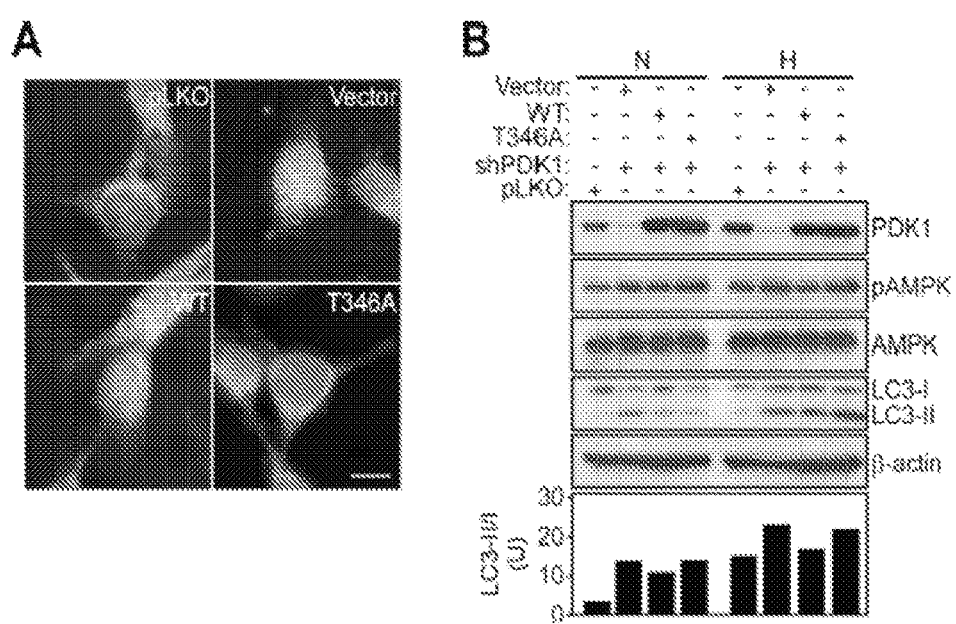

FIG. 14, related to FIG. 6, illustrates additional data regarding regulation of autophagy by mitochondrial Akt-PDK1 phosphorylation. A: PC3 cells in normoxia were stably transduced with control pLKO or PDK1-directed shRNA and analyzed for GFP-LC3 fluorescence by fluorescence microscopy. Scale bar, 10 µm. B: PC3 cells with stable shRNA (sh) knockdown of PDK1 or transduced with control pLKO were reconstituted in normoxia (N) or hypoxia (H) with control vector, WT PDK1 or T346A PDK1 mutant cDNA and analyzed by Western blotting. p, phosphorylated. Bottom, densitometric quantification of the ratio of LC3 conversion (LC3-I) to an autophagy-related, lipidated form (LC3-II). U, arbitrary units.

Figure 15:
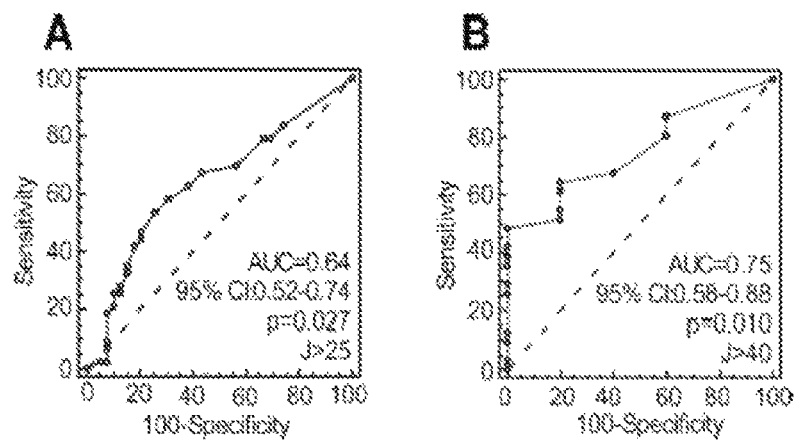

FIG. 15, related to FIG. 8, illustrates additional data regarding identification of pPDK1-IHC cut-offs to categorize glioma patients into high- or low-expressor group. Receiver Operating Characteristic (ROC) curve analysis was used to identify the optimal cut-off of pPDK1 IHC score for (A) glioma or (B) GBM patients categorization into low- or high-pPDK1 expressors. AUC, Area under curve. 95% CI, 95% Confidence Interval. J, Youden's Index associated criterion.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties.

Definitions

The term "pT346 PDK1" refers to human PDK1 that is phosphorylated at threonine (T; Thr) corresponding to position 346 having SEQ ID NO: 1 below.

(SEQ ID NO: 1)

```
  1  MRLARLLRGA ALAGPGPGLR AAGFSRSFSS DSGSSPASER GVPGQVDFYA RFSPSPLSMK

61  QFLDFGSVNA CEKTSFMFLR QELPVRLANI MKEISLLPDN LLRTPSVQLV QSWYIQSLQE

121  LLDFKDKSAE DAKAIYDFTD TVIRIRNRHN DVIPTMAQGV IEYKESFGVD PVTSQNVQYF

181  LDRFYMSRIS IRMLLNQHSL LFGGKGKGSP SHRKHIGSIN PNCNVLEVIK DGYENARRLC

241  DLYYINSPEL ELEELNAKSP GQPIQVVYVP SHLYHMVFEL FKNAMRATME HHANRGVYPP

301  IQVHVTLGNE DLTVKMSDRG GGVPLRKIDR LFNYMYSTAP RPRVETSRAV PLAGFGYGLP

361  ISRLYAQYFQ GDLKLYSLEG YGTDAVIYIK ALSTDSIERL PVYNKAAWKH YNTNHEADDW

421  CVPSREPKDM TTFRSA
```

For example, the Thr346 is identified in PDK1 chymotryptic peptides, including the sequence STAPRPRVE-pTSRAVPL (m/z=908.9751) as the sole phospho-amino acid modified by Akt1 or Akt2, compared to control (Item F in FIG. 2).

The term "T346 PDK1" refers to PDK1 that is not phosphorylated at threonine (T; Thr) corresponding to position 346 underlined above in SEQ ID NO: 1.

The terms "co-administration," "co-administering," "administered in combination with," "administering in combination with," "simultaneous," and "concurrent," as used herein, encompass administration of two or more active pharmaceutical ingredients to a human subject so that both active pharmaceutical ingredients and/or their metabolites are present in the human subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present is also encompassed in the methods of the invention.

The terms "active pharmaceutical ingredient" and "drug" include PDK1 and/or AKT inhibitors.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the human subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit in a human subject. A prophylactic effect includes delaying or eliminating the appearance of a disease or condition, delaying or eliminating the onset of symptoms of a disease or condition, slowing, halting, or reversing the progression of a disease or condition, or any combination thereof.

"Biological sample" may be obtained from a source, including, but not limited to, whole blood, serum, plasma, urine, saliva, sweat, fecal matter, tears, intestinal fluid, mucous membrane samples, lung tissue, tumors, transplanted organs, fetus, and/or other sources. The biological samples may be from an animal, including human, fluid, solid (e.g., stool) or tissue. Biological samples may include materials taken from a patient including, but not limited to tissue biopsy, cultures, blood, saliva, cerebral spinal fluid, pleural fluid, milk, lymph, sputum, semen, needle aspirates, and the like. In some embodiments, when the biological sample is plasma, the method described herein may comprise isolating the plasma from a blood sample of a subject. In further embodiments, when biological sample is serum, the method may comprise isolating the serum from a blood sample of a subject. These examples are not to be construed as limiting the sample types applicable to the present invention.

The term "antibody" refers to a protein molecule functioning as a receptor that specifically recognizes an antigen, and includes an immunoglobulin molecule immunologically reactive with a specific antigen. The term also includes polyclonal antibodies, monoclonal antibodies, whole antibodies and antibody fragments. Further, the term also include chimeric antibodies (for example, humanized murine antibodies), bivalent or bispecific molecules (for example, bispecific antibodies), dibodies, triabodies and tetrabodies. The whole antibodies have two full-length light chains and two full-length heavy chains, and each of the light chains is linked to the heavy chain by a disulfide bond. The whole antibodies include IgA, IgD, IgE, IgM and IgG, and IgG has subtypes, including IgG1, IgG2, IgG3 and IgG4. The antibody fragments refer to fragments having a function of binding to antigens and include Fab, Fab', F(ab')$_2$ and Fv. Fab has light chain and heavy chain variable regions, a light chain constant region and a first heavy chain constant region (CH1 domain) and includes one antigen-binding site. Fab' differs from Fab in that it has a hinge region including at least cysteine residue in the C-terminal region of the heavy chain CH1 domain. F(ab')$_2$ antibody is prepared by a disulfide bond between cysteine residues in the hinge region of Fab'. Fv (variable fragment) refers to the minimum antibody fragment having only a heavy chain variable region and a light chain variable region. Double-stranded Fv (dsFv) has a heavy chain variable region linked to a light chain variable region by a disulfide bond, and single-chain Fv (scFv) generally has a heavy chain variable region covalently linked to a light chain variable region by a peptide linker. Such antibody fragments can be obtained using proteases (for example, Fab fragments can be obtained by cleaving whole antibody with papain, and F(ab')$_2$ fragments can be obtained by cleaving whole antibody with pepsin). The antibody fragments may be constructed by genetic recombination technology.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

The pharmaceutical compositions to treat cancer as described herein may include a pharmaceutically acceptable carrier or pharmaceutically acceptable excipient. "Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The term "and/or" used herein is defined to indicate any combination of the components. Moreover, the singular forms "a," "an," and "the" may further include plural referents unless the context clearly dictates otherwise. Thus, for example, reference to "a sample" refers to one, more than one, or mixtures of samples.

Methods of Detecting and Treating Cancer

In one aspect, the compositions and methods described herein may be used in a method of detecting and treating cancer or tumor expressing pT346 PDK1. The compositions and methods described herein may have therapeutic effects on one or more cancers or tumors.

In another aspect, the present disclosure is related to the methods of treating cancer in a subject in which cancer cells express Pyruvate Dehydrogenase Kinase-1 (PDK1) that is phosphorylated at T346 (pT346 PDK1), the methods comprising administering a therapeutically effective dose of a PDK1 inhibitor and/or an Protein Kinase B-beta (AKT) inhibitor to the subject.

In some embodiments, the method described herein may detect and/or treat hypoxic tumor. In further embodiments, the cancer may be blood or solid tumor. In additional embodiments, the cancer may comprise any one or more of the following: Acute Lymphoblastic; Acute Myeloid Leukemia; Adrenocortical Carcinoma; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma; Central Nervous System Atypical Teratoid/Rhabdoid Tumor; Central Nervous System Embryonal Tumors; Cerebellar Astrocytoma; Cerebral Astrocytoma/Malignant Glioma; Craniopharyngioma; Ependymoblastoma; Ependymoma; Medulloblastoma; Medulloepithelioma; Pineal Parenchymal Tumors of Intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma; Cerebral Astrocytoma/Malignant Glioma, Childhood; Cervical Cancer; Chordoma; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Intraocular Melanoma; Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor; Gestational Trophoblastic Tumor; Glioma; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; Intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenström; Malignant Fibrous Histiocytoma of Bone and Osteosarcoma; Medulloblastoma; Melanoma; Melanoma, Intraocular (Eye); Merkel Cell Carcinoma; Mesothelioma; Metastatic Squamous Neck Cancer with Occult Primary; Mouth Cancer; Multiple Myeloma/Plasma Cell Neoplasm; Mycosis Fungoides; Myelodysplastic Syndromes; Myelodysplastic/Myeloproliferative Diseases; Myelogenous Leukemia; Myeloid Leukemia; Myeloma; Myeloproliferative Disorders; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Cell Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenström Macroglobulinemia; or Wilms Tumor.

In additional embodiments, the subject may be human.

In further embodiments, the methods may comprise isolating a biological sample from the subject and/or detecting pT346 PDK1 in the biological sample. For example, the biological sample may be a tissue biopsy or blood sample. In yet further embodiments, the methods may comprise comparing the pT346 PDK1 level in the biological sample to a level of pT346 PDK in normoxic cells. The methods may further comprise detecting pT346 PDK1 in normoxic cells. As used herein, "normoxic cells" refer to cells exposed to normal oxygen conditions. When cancer cells are cultured in vivo under normal atmospheric oxygen concentrations (e.g. about 20%, which, at a standard atmospheric pressure of 760 mm Hg, corresponds to a partial pressure of oxygen (pO2) of about 152 mm Hg) the culture medium has an oxygen concentration of about 13% (pO2«98 mm Hg) which corresponds approximately to the oxygen concentration of arterial blood. Thus, the term "normoxic" may be taken herein as referring to cancer cells subject to an oxygen concentration comparable to trophoblasts cultured under an atmosphere containing a normal oxygen concentration (e.g. about 20% or about 152 mm Hg).

In additional embodiments, an improvement in a measurable criterion in an individual to whom the treatment is applied may be measured, compared to one who has not received the treatment. For this purpose, a number of criteria may be designated, which reflect the progress of cancer or the well-being of the human subject. Useful criteria may include tumour size, tumour dimension, largest dimension of tumour, tumour number, presence of tumour markers (such as alpha-feto protein), degree or number of metastases, etc. Thus, as an example, a treated individual may show a decrease in tumour size or number as measured by an appropriate assay or test. A treated subject may for example show a 1%, 2%, 3%, 4%, 5%, 6%, 7%, 8%, 9%, 10%, 15%, 20%, 25%, 30%, 40%, 50%, 60%, 70%, 80%; 90%, 95% or more, or 100% decrease in tumour size of a particular tumour, or decrease in tumour number, or both, compared to an individual who has not been treated. In some embodiments, the effect of the treatment is suitably quantified using standard tests, such as the international criteria proposed by the Response Evaluation Criteria in Solid Tumours (RECIST) Committee, as described in detail in Therasse (2000) J Natl Cancer Inst 92: 205-16.

In some embodiments, detecting, discovering, determining, measuring, evaluating, counting, and assessing the cancer or cancer cells are used interchangeably and include quantitative and/or qualitative determinations, including, for example, determining presence and/or absence of the cancer, identifying the cancer, and quantifying the cancer cells, such as tumor size, dimension, or number.

In another aspect, the compositions and methods described herein can be used in a method of detecting a hypoxic tumor. In some embodiments, detecting, discovering, determining, measuring, evaluating, counting, and assessing the hypoxic tumor or hypoxic tumor cells are used interchangeably and include quantitative and/or qualitative determinations, including, for example, determining presence and/or absence of the hypoxic tumor or hypoxic tumor cells, identifying the tumor, and quantifying the hypoxic tumor or hypoxic tumor cells. In some embodiments, the present disclosure is related to methods of detecting a hypoxic tumor in a human subject comprising isolating a biological sample from a subject, and detecting pT346 PDK1 in the biological sample. In additional embodiments, the detecting may comprise contacting a biological sample with an anti-pT346 antibody and detecting binding between pT346 PDK1 and the antibody.

In another aspect, the methods of detecting and/or treating as set forth herein may comprise detecting hypoxic cancer or tumor cells in a subject. In some embodiments, the detecting may comprise contacting a biological sample with an anti-pT346 PDK1 antibody and detecting binding between pT346 PDK1 and the antibody. For example, the presence of pT346 PDK1 or a higher level of pT346 PDK1 in the biological sample compared to a control indicates the presence or increase of a hypoxic tumor. In further embodiments, the control indicates a level of pT346 PDK1 in normoxic cells or in a sample from a normal subject or the same subject at an earlier time. In yet additional embodiments, the detecting may comprise contacting a biological sample with an anti-T346 PDK1 antibody and detecting binding between T346 PDK1 and the antibody. For example, a lower level of T346 PDK1 in the biological sample compared to a control indicates the presence or increase of a hypoxic tumor.

In another aspect, the present disclosure may be related to use of the anti-pT346 PDK1 antibody or anti-T346 PDK1 antibody in detecting or measuring pT346 PDK1 in a biological sample. The methods described herein may comprise detecting or measuring pT346 PDK1 in a biological sample.

In another aspect, the present disclose may be related to methods of screening for the anti-pT346 PDK1 antibody or anti-T346 PDK1 antibody. Such antibodies may be screened using the technology known in the art. For example, it is reported that a human IgE monoclonal antibody and a fragment thereof can be screened by using a phage display method (e.g., Steinverger (1996) J. Biol. Chem. 271, 10967-10972). A human IgE monoclonal antibody having a desired bioactivity may be obtained by preparing a human IgE naive (i.e., non-immunized) library using filamentous phages such as M13 that express proteins from total RNA extracted from human IgE producing cells, and screening the library by panning.

In another aspect, the present disclose may be related to methods of manufacturing the anti-pT346 PDK1 antibody or anti-T346 PDK1 antibody. As an antibody to pT346 PDK1 and T346 PDK1, antibodies derived from human, mouse, rat, rabbit, or goat including polyclonal or monoclonal antibodies, complete or shorten (e.g., F(ab')$_2$, Fab', Fab, or Fv fragment) antibodies, chimeric antibodies, humanized antibodies, or completely humanized antibodies will be acceptable. Such antibodies can be manufactured using pT346 PDK1 and pT346 PDK1 as an antigen according to well-known production methods of antibody or antiserum. The polyclonal antibodies can be manufactured according to well-known methods. For example, they can be manufactured by separation and refinement of the antibody of which a mixture of an antigen and a carrier protein is immunized to suitable animal, and an antibody inclusion to the antigen is gathered from the immunized animal. As such animal, mouse, rat, sheep, goat, rabbit, and guinea pig are generally enumerated. To improve the antibody producibility, Freund's complete adjuvant or Freund's incomplete adjuvant can be administered with the antigen. The administering is usually executed once every two weeks about 3-10 times in total. The polyclonal antibody can be gathered from the immunized animal's blood and peritoneal fluid, etc. by the above method. The measurement of the polyclonal antibody's titer in antiserum can be measured by ELISA. The separation and refinement of the polyclonal antibody can be executed by refining techniques that use active adsorbents such as antigen binding solid phase, protein A. or protein G, etc., salting-out, alcohol precipitation, isoelectric precipitation, electrophoresis, adsorption and desorption with ion exchanger, ultracentrifugation, or separation and refinement of immunoglobulins such as gel filtration technique, etc. The monoclonal antibody producing cells can be prepared as hybridomas to be possible to subculture which produce the monoclonal antibody by selecting the individual of which the antibody titre is confirmed in an antigen immunized animals, gathering the spleen or the lymph node on day 2-5 after the final immunization, and fusing the antibody producing cells included in them with homogeneous or heterozoic myeloma cells. The antigen itself or with the carrier and the diluent is administered to the part in which the antibody production is possible. To improve the antibody producibility, Freund's complete adjuvant or Freund's incomplete adjuvant can be administered with the antigen. According to the method of calling "DNA immunization", animals are immunized. This method is a method using a phenomenon in which antigen-expressing vectors are introduced into the part and are taken into myocytes on the process of tissue repair, and expresses the antigenic protein (*Nature immunology* (2001), vol. 2, issue 3, p. 261-267) after Cardiotoxin is treated to immune animal's tibialis anterior muscle of hind leg.

PDK1 and AKT Inhibitors

In an embodiment, the invention includes a method of a tumor in a human subject in which tumor cells expressing PDK1 are phosphorylated at T346 (pT346), the method comprising the step of administering a therapeutically effective dose of a PDK1 inhibitor and/or an AKT inhibitor to the human subject. The PDK1 and AKT inhibitors may be any PDK1 and AKT inhibitors known in the art. In particular, the PDK1 and AKT inhibitor may be PDK1 and AKT inhibitors described in more detail in the following paragraphs.

In some embodiments, the PDK1 inhibitor is selected from the group consisting of

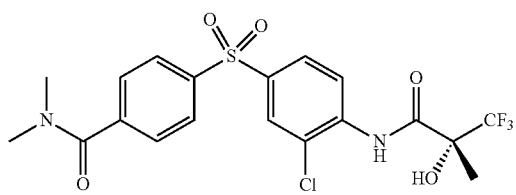 [SMILES: CN(C)C(=O)c1ccc(S(=O)(=O)c2ccc(NC(=O)[C@@](C)(O)C(F)(F)F)c(Cl)c2)cc1]

4-[3-chloro-4-[[(2R)-3,3,3-trifluoro-2-hydroxy-2-methylpropanoyl]amino]phenyl]sulfonyl-N,N-dimethylbenzamide (also called AZD7545);

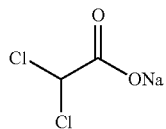

sodium dichloroacetate (also called CERESINE);

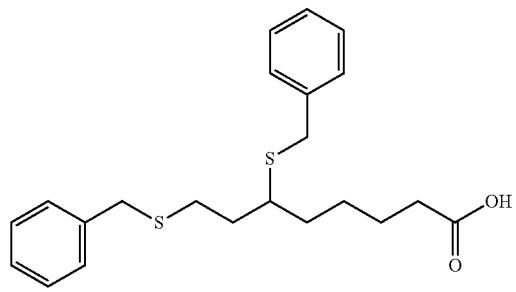 [SMILES: O=C(O)CCCCC(CCSCc1ccccc1)SCc1ccccc1]

6,8-bis(benzylsulfanyl)octanoic acid (also called CPI613); lipoic acid or 6,8-bis[(phenylmethyl)thio]-octanoic acid (also called JTT251); and

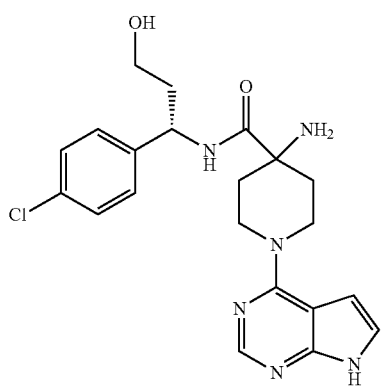 [SMILES: NC1(C(=O)N[C@@H](CCO)c2ccc(Cl)cc2)CCN(c2ncnc3[nH]ccc23)CC1]

4-amino-N-[(1 S)-1-(4-chlorophenyl)-3-hydroxypropyl]-1-(7H-pyrrolo[2,3-d]pyrimidin-4-yl)piperidine-4-carboxamide (AZD5363). For example, U.S. Pat. No. 6,727,284 describes the cresine inhibitors and is herein incorporated by reference in its entirety. U.S. Pat. No. 8,263,653 describes the CPI613 inhibitors and is herein incorporated by reference in its entirety.

In some embodiments, the AKT inhibitor is an AKT2 inhibitor. In additional embodiments, the AKT inhibitor is selected from the group consisting of

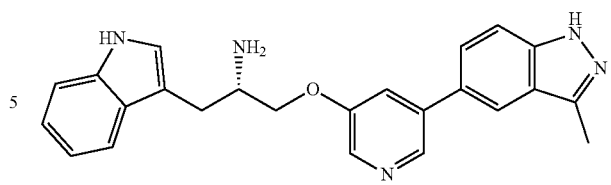

(2s)-1-(1h-Indol-3-Yl)-3-{[5-(3-Methyl-1h-Indazol-5-Yl)pyridin-3-Yl]oxy}propan-2-Amine or 5-{5-[(2S)-2-amino-3-(1H-indol-3-yl)propoxy]pyridin-3-yl}-3-methyl-1H-indazole (also called A-443654); ALM301 described in U.S. Pat. No. 9,221,838, which is herein incorporated by reference in its entirety;

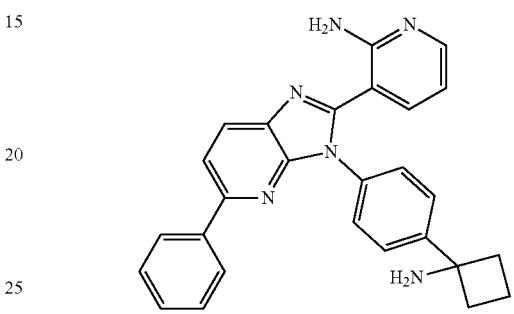

3-(3-(4-(1-aminocyclobutyl)phenyl)-5-phenyl-3H-imidazo[4,5-b]pyridin-2-yl)pyridin-2-amine; COTI2 described in U.S. Pat. No. 8,034,815, which is herein incorporated by reference in its entirety. Suitable AKT inhibitors are also described, for example, in Nitulescu (2016) International Journal of Oncology 48, 869-885, the disclosure of which is incorporated by reference herein. In additional embodiments, the AKT inhibitors may include ATP-competitive inhibitors, such as isoquinoline-5-sulfonamides including

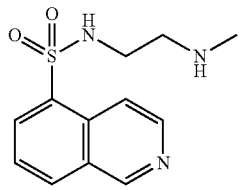 [SMILES: CNCCNS(=O)(=O)c1cccc2cnccc12]

H-8,

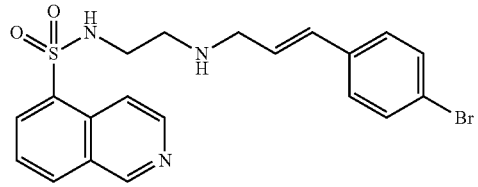 [SMILES: O=S(=O)(NCCNC/C=C/c1ccc(Br)cc1)c1cccc2cnccc12]

H-89 and

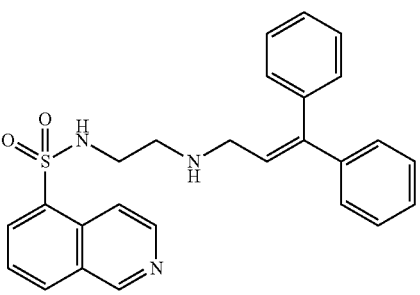 [SMILES: O=S(=O)(NCCNCC=C(c1ccccc1)c1ccccc1)c1cccc2cnccc12]

NL-71-101, aminofurazans including
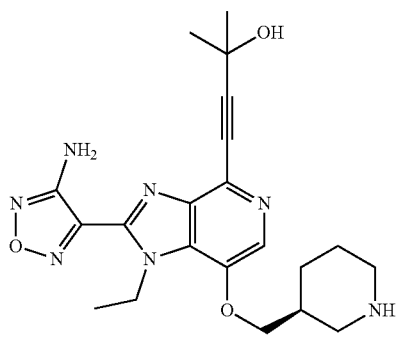 [SMILES: CCn1c(-c2nonc2N)nc2c(C#CC(C)(C)O)ncc(OC[C@H]3CCCNC3)c21]
GSK690693, heterocyclic rings including
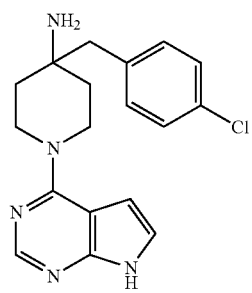 [SMILES: NC1(Cc2ccc(Cl)cc2)CCN(c2ncnc3[nH]ccc23)CC1]
CCT128930,
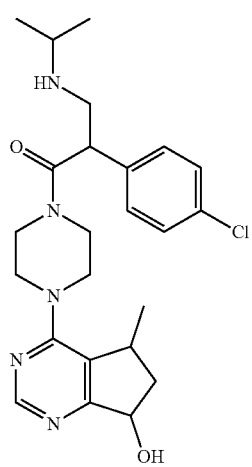 [SMILES: CC(C)NCC(C(=O)N1CCN(c2ncnc3c2C(C)CC3O)CC1)c1ccc(Cl)cc1]
ipatasertib,
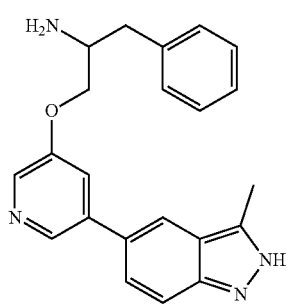 [SMILES: Cc1[nH]nc2ccc(-c3cncc(OCC(N)Cc4ccccc4)c3)cc12]
A-674563 and
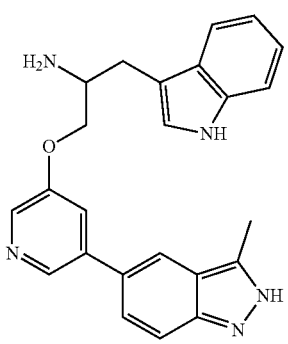 [SMILES: Cc1[nH]nc2ccc(-c3cncc(OCC(N)Cc4c[nH]c5ccccc45)c3)cc12]
A-443654, phenylpyrazole derivatives including.
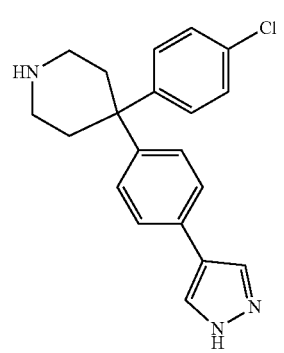 [SMILES: Clc1ccc(C2(c3ccc(-c4cn[nH]c4)cc3)CCNCC2)cc1]
AT7867 and
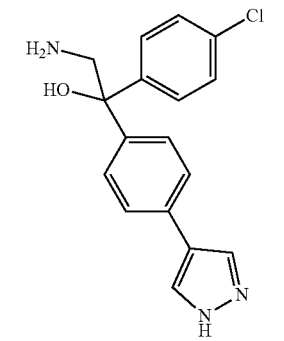 [SMILES: NCC(O)(c1ccc(Cl)cc1)c1ccc(-c2cn[nH]c2)cc1]
AT13148, and thiophenecarbozamide derivatives including
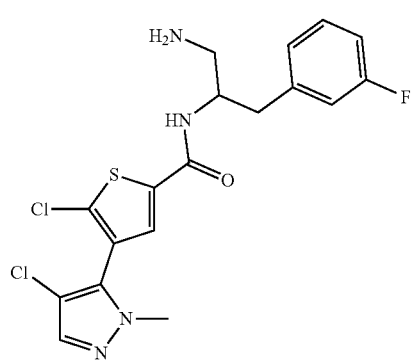 [SMILES: Cn1ncc(Cl)c1-c1cc(C(=O)NC(CN)Cc2cccc(F)c2)sc1Cl]

afuresertib (GSK2110183), 2-pyrimidyl-5-amidothiophene derivative including

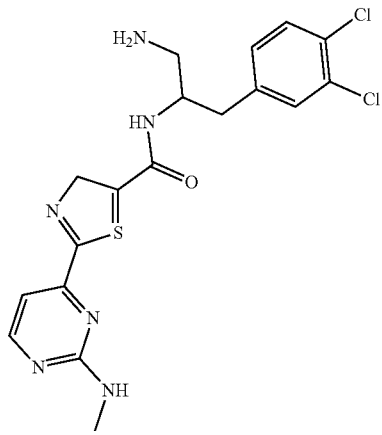

DC120,

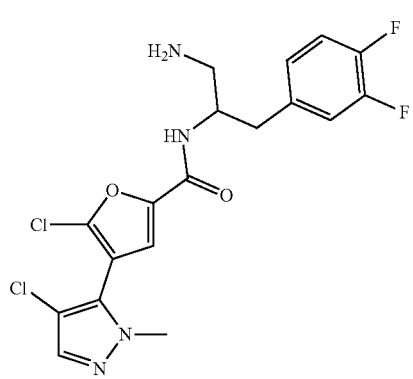 [SMILES: Cn1ncc(Cl)c1-c1cc(C(=O)NC(CN)Cc2ccc(F)c(F)c2)oc1Cl]

uprosertib (GSK2141795); allosteric inhibitors, such as 2,3-diphenylquinoxaline analogues including

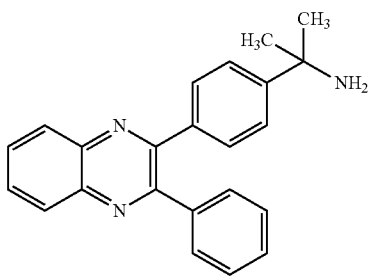

2-[4-(2-aminoprop-2-yl)phenyl]-3-phenylquinoxaline (2,3 diphenylquinoxaline derivative), and

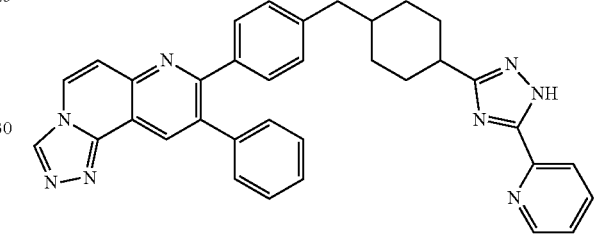

triazolo[3,4-f][1,6]naphthyridin 3(2H) one derivative (MK-2206), alkylphospholipids including

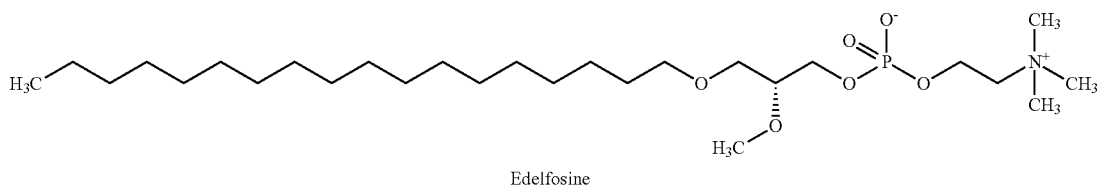
Edelfosine

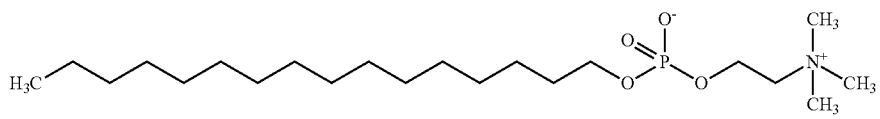
Miltefosine

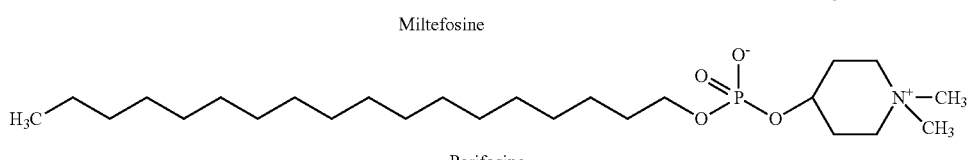
Perifosine

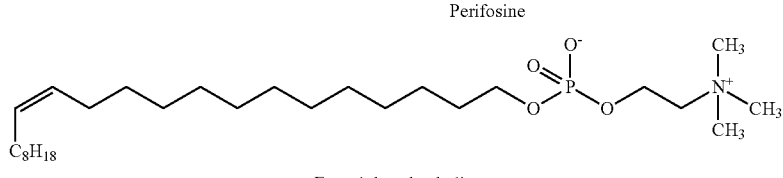
Erucylphosphocholine

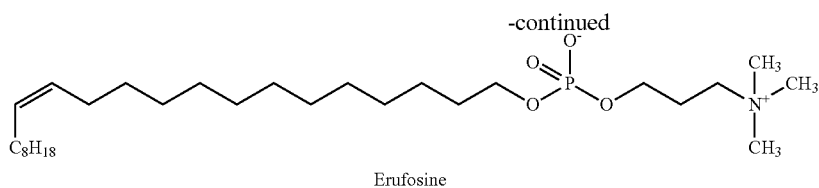
Erufosine ilmofosine (1-Hexadecylmercapto-2-methoxymethyl-3-propyl phosphoric acid monocholine ester; BM 41.440), miltefosine (hexadecylphosphocholine, HePC), perifosine (Octadecyl-(1,1-dimethyl-4-piperidylio) phosphate; D 21266), erucylphosphocholine (ErPC), erufosine

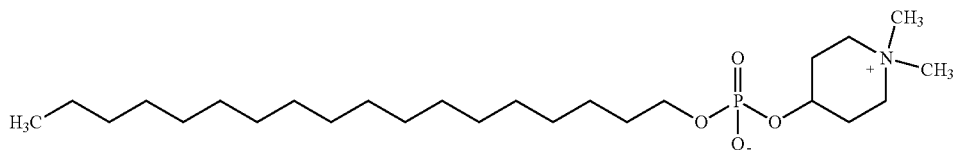

(ErPC3), erucylphosphohomocholine, indole-3-carbinol analogues including Indole 3 carbinol, 3-chloroacetylindole, diindolylmethane, diethyl 6-methoxy-5,7-dihydroindolo[2,3-b]carbazole-2,10-dicarboxylate (SR13668), and

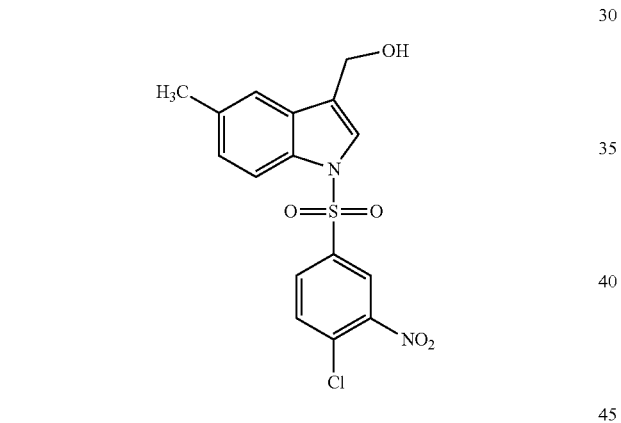

(OSU-A9), sulfonamide and thiourea derivatives including

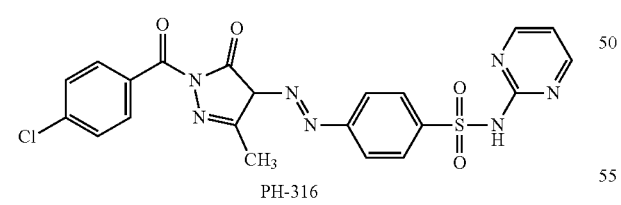
PH-316

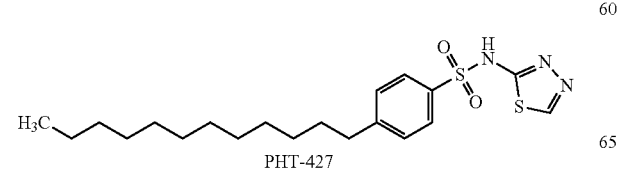
PHT-427

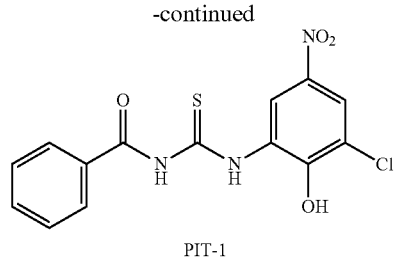
PIT-1

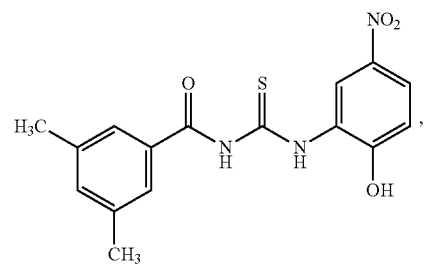
DM-PIT-1 purine derivatives including

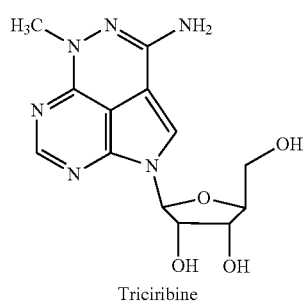
Triciribine

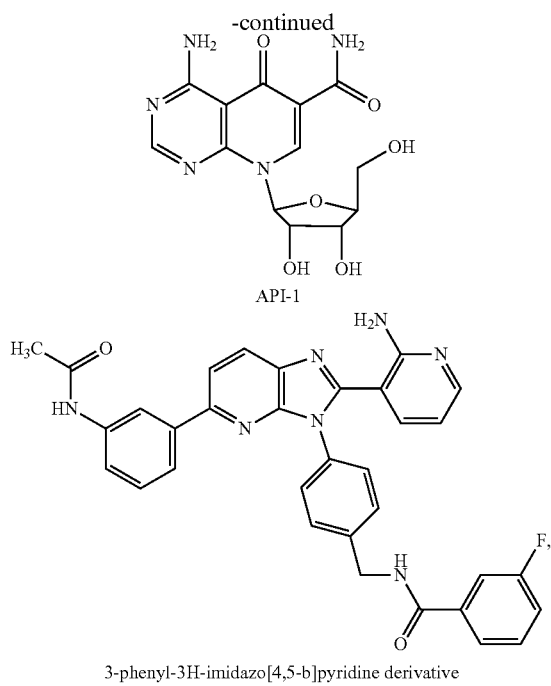

API-1

3-phenyl-3H-imidazo[4,5-b]pyridine derivative triciribine mono-phosphate active analogue (tricyclic nucleotide triciribine phosphate or triciribine phosphate monohydrate (TCN-P), 4-Amino-5,8-dihydro-5-oxo-8-β-D-ribofuranosyl-pyrido[2,3-d]pyrimidine-6-carboxamide) or other structures and derivatives (e.g. 3-methyl-xanthine, quinoline-4-carboxamide and 2-[4-(cyclohexa-1,3-dien-1-yl)-1H-pyrazol-3-yl]phenol, 3-oxo-tirucallic acid, 3α-acetoxy-tirucallic and 3β-acetoxy-tirucallic acids, and acetoxy-tirucallic acid); irreversible inhibitors including

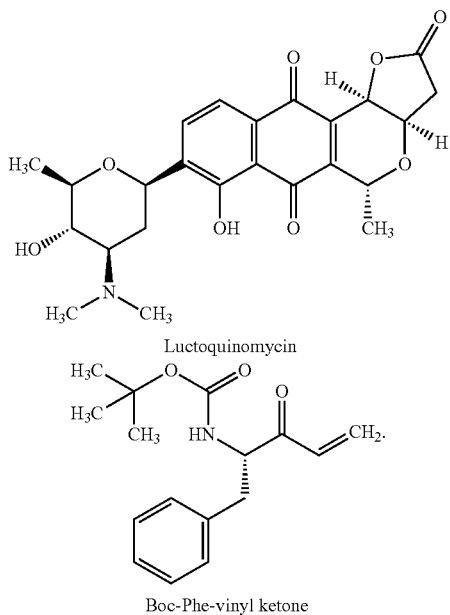

Luctoquinomycin

Boc-Phe-vinyl ketone

Pharmaceutical Compositions for Oral Administration

In some embodiments, the invention provides a pharmaceutical composition for oral administration containing the active pharmaceutical ingredient or combination of active pharmaceutical ingredients, such as the PDK1 and AKT inhibitors described herein, and a pharmaceutical excipient suitable for oral administration.

In some embodiments, the invention provides a solid pharmaceutical composition for oral administration containing: (i) an effective amount of an active pharmaceutical ingredient or combination of active pharmaceutical ingredients, and (ii) a pharmaceutical excipient suitable for oral administration. In selected embodiments, the composition further contains (iii) an effective amount of a third active pharmaceutical ingredient and optionally (iv) an effective amount of a fourth active pharmaceutical ingredient.

In some embodiments, the pharmaceutical composition may be a liquid pharmaceutical composition suitable for oral consumption. Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the active pharmaceutical ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In some embodiments, the invention provides a pharmaceutical composition for injection containing an active pharmaceutical ingredient or combination of active pharmaceutical ingredients, such as PDK1 and AKT inhibitors, and a pharmaceutical excipient suitable for injection.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid and thimerosal.

Sterile injectable solutions are prepared by incorporating an active pharmaceutical ingredient or combination of active pharmaceutical ingredients in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

In some embodiments, the invention provides a kit comprising (1) a composition comprising a therapeutically effective amount of an active pharmaceutical ingredient or combination of active pharmaceutical ingredients or a pharmaceutically acceptable salt, solvate, hydrate, cocrystal, or prodrug thereof, and (2) a diagnostic test for determining whether a patient's cancer is a particular subtype of a cancer. Any of the foregoing diagnostic methods may be utilized in the kit.

The kits described above are for use in the treatment of the diseases and conditions described herein. In an embodiment, the kits are for use in the treatment of cancer. In some embodiments, the kits are for use in treating solid tumor cancers.

In an embodiment, the kits of the present invention are for use in the treatment of cancer described herein.

Dosages and Dosing Regimens

The amounts of the pharmaceutical compositions administered using the methods herein, such as the dosages of PDK1 and AKT inhibitors, will be dependent on the human or mammal being treated, the severity of the disorder or condition, the rate of administration, the disposition of the active pharmaceutical ingredients and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of the pharmaceutical compositions and active pharmaceutical ingredients may be provided in units of mg/kg of body mass or in mg/m2 of body surface area.

In some embodiments, the invention includes a methods of treating a cancer in a human subject suffering from the cancer in which cancer cells express pT346 PDK1, such as glioma expressing pT346 PDK1, the method comprising the steps of administering a therapeutically effective dose of an active pharmaceutical ingredient that is an PDK1 and/or AKT inhibitor to the human subject.

In some embodiments, a pharmaceutical composition or active pharmaceutical ingredient is administered in a single dose. Such administration may be by injection, e.g., intravenous injection, in order to introduce the active pharmaceutical ingredient quickly. However, other routes, including the oral route, may be used as appropriate. A single dose of a pharmaceutical composition may also be used for treatment of an acute condition.

In some embodiments, a pharmaceutical composition or active pharmaceutical ingredient is administered in multiple doses. In an embodiment, a pharmaceutical composition is administered in multiple doses. Dosing may be once, twice, three times, four times, five times, six times, or more than six times per day. Dosing may be once a month, once every two weeks, once a week, or once every other day. In other embodiments, a pharmaceutical composition is administered about once per day to about 6 times per day. In some embodiments, a pharmaceutical composition is administered once daily, while in other embodiments, a pharmaceutical composition is administered twice daily, and in other embodiments a pharmaceutical composition is administered three times daily.

Administration of the active pharmaceutical ingredients in the methods of the invention may continue as long as necessary. In selected embodiments, a pharmaceutical composition is administered for more than 1, 2, 3, 4, 5, 6, 7, 14, or 28 days. In some embodiments, a pharmaceutical composition is administered for less than 28, 14, 7, 6, 5, 4, 3, 2, or 1 day. In some embodiments, a pharmaceutical composition is administered chronically on an ongoing basis—e.g., for the treatment of chronic effects. In some embodiments, the administration of a pharmaceutical composition continues for less than about 7 days. In yet another embodiment the administration continues for more than about 6, 10, 14, 28 days, two months, six months, or one year. In some cases, continuous dosing is achieved and maintained as long as necessary.

In some embodiments, an effective dosage of an active pharmaceutical ingredient disclosed herein is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of an active pharmaceutical ingredient disclosed herein is about 25 mg, about 50 mg, about 75 mg, about 100 mg, about 125 mg, about 150 mg, about 175 mg, about 200 mg, about 225 mg, or about 250 mg.

In some embodiments, an effective dosage of an active pharmaceutical ingredient disclosed herein is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of an active pharmaceutical ingredient disclosed herein is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some embodiments, an effective dosage of an active pharmaceutical ingredient disclosed herein is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg. In some embodiments, an effective dosage of an active pharmaceutical ingredient disclosed herein is about 25 mg, about 50 mg, about 75 mg, about 100 mg, about 125 mg, about 150 mg, about 175 mg, about 200 mg, about 225 mg, or about 250 mg.

In some embodiments, an active pharmaceutical ingredient is administered at a dosage of 10 to 200 mg BID, including 50, 60, 70, 80, 90, 100, 150, or 200 mg BID. In some embodiments, an active pharmaceutical ingredient is administered at a dosage of 10 to 500 mg BID, including 1, 5, 10, 15, 25, 50, 75, 100, 150, 200, 300, 400, or 500 mg BID.

In some instances, dosage levels below the lower limit of the aforesaid ranges may be more than adequate, while in other cases still larger doses may be employed without causing any harmful side effect—e.g., by dividing such larger doses into several small doses for administration throughout the day.

An effective amount of the combination of the active pharmaceutical ingredient may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Cells and Cell Culture.

Human prostate adenocarcinoma PC3 and DU145, glioblastoma (GBM) LN229, and breast adenocarcinoma MCF-7 or MDA-231 cells were obtained from the American Type Culture Collection (ATCC, Manassas, Va.), and maintained in culture according to the supplier's specifications. Hypoxic treatment was carried out using an enclosed chamber (BioSpherix) flushed with a nitrogen and $CO_2$ gas. The $O_2$ and $CO_2$ concentrations in the chamber were maintained at 0.5% and 5%, respectively, using a carbon dioxide & oxygen controller (BioSpherix). These conditions were maintained constant throughout the course of the experiments. Human U251-HRE GBM cells express a luciferase reporter gene under the control of three copies of a Hypoxia-Responsive Element (HRE) sequence (pGL2-Tk-HRE). The cells were infected with a lentiviral vector (pCLL.PGK.mCherry.WPRE, PmW) containing the m-Cherry gene under control of the constitutive PGK promoter. Cells were maintained in RPMI medium supplemented with 10% heat-inactivated fetal bovine serum, penicillin and streptomycin (50 IU/ml), 2 mM glutamine (all from Euroclone) and 2 μg/ml G418 (Sigma Aldrich) in a humidified atmosphere of 5% of $CO_2$ at 37° C.

Primary GBM Cultures and Neurospheres.

Short-term cultures of GBM neurospheres or differentiated monolayers were obtained as described (Caino et al. (2015) Proc Natl Acad Sci USA 112, 8638-8643; Di Cristofori (2015) Oncotarget 6, 17514-17531) from three chemotherapy- and radiotherapy-naive patients surgically treated at the Neurosurgery Division of Fondazione IRCCS Ca' Granda Ospedale Maggiore Policlinico and histologically diagnosed with GBM (WHO grade IV). Post-surgical samples were used after obtaining the patient's signed informed consent and approval from an Institutional Review Board at the same Institution.

Antibodies and Reagents.

The following antibodies to PDK1 (Abcam), Ser293 (precursor protein, corresponding to site 1, Ser264 in the mature protein)-phosphorylated pyruvate dehydrogenase E1 subunit a (pPDHE1α, Millipore), PDHE1α (Cell Signaling), Ser473-phosphorylated Akt (pAkt, Cell Signaling), Ser474-phosphorylated Akt2 (pAkt2, Cell Signaling), Akt2 (Cell Signaling), pan-Akt (Cell Signaling), phospho-Akt consensus substrate antibody (Akt cons Ab) recognizing the sequence RxRxxS/T (Cell Signaling), hexokinase-II (HK2, Cell Signaling), VDAC 1 (Cell Signaling), Hypoxia-Inducible Factor-1α (HIF1α, Cell Signaling), Thr172-phosphorylated AMPKα (Cell Signaling), AMPKα (Cell Signaling), cleaved (active) caspase 3 (Cell Signaling), LC3II (Cell Signaling), PTEN (Cell Signaling), β-tubulin (Sigma-Aldrich) or β-actin (Sigma-Aldrich) were used. A polyclonal antibody to Thr346 (T346)-phosphorylated PDK1 was generated in rabbits using the phospho-peptide, CAPRPRVE pTSRAVPLA (p, phosphorylated residue, underlined), and affinity-purified. Purified recombinant His-tagged PDK1, PDK2, PDK3, PDK4 and Human Pyruvate Dehydrogenase E1-alpha subunit proteins were obtained from Abcam. Kinase active Akt1 and Akt2 were from SignalChem. A GST-tagged GSK3α peptide (Cell Signaling) was used as a control Akt substrate. Sodium dichloroacetate (DCA, Sigma-Aldrich), PX-866 (LC Laboratories), Bafilomycin A1 (Sigma-Aldrich) and MK2206 (Selleck Chemicals) were used. Total protein lysates prepared from adult normal prostate or prostatic adenocarcinoma samples were used. To evaluate physiological hypoxia within primary GBM neurospheres or differentiated cultures, live cells were incubated with the fluorogenic probe Image-iT Hypoxia Reagent (H10498; Molecular Probe; Thermo Fisher Scientific) which has an excitation/emission spectra of 490/610 nm. The probe becomes fluorescent in low-oxygen environments. After imaging, the cultures were fixed in 4% PFA and processed for immunofluorescence analyses.

Transfections.

A human PDK1 cDNA was purchased from GeneCopoeia. Human Akt2 cDNA was purchased from Addgene. Mitochondrial-targeted wild type (WT) Akt2 or Akt kinase-dead (KD) cDNA was generated by fusing the mitochondrial import sequence of cytochrome c oxidase subunit 8 (COX8A) to the N-terminus of each cDNA construct. A PDK1 Thr346→Ala (T346A) mutant cDNA was generated using QuikChange-XL site-directed mutagenesis kit (Stratagene). For gene knockdown experiments, tumor cells were transfected with control, non-targeting small interfering RNA (siRNA) pool (Dharmacon) or specific siRNAs directed to HIF1α (Dharmacon), PTEN (Santa Cruz Biotech), PDK1 (Santa Cruz Biotech), Akt1 (Santa Cruz Biotech) or Akt2 (Santa Cruz Biotech). The various siRNAs were transfected at 10 nM using Oligofectamine (Invitrogen). Transfection of plasmid DNAs was carried out with X-Tremegene (Roche).

Generation of Stable Cell Lines.

PC3 cells stably expressing shRNA targeting PDK1 were generated by infection with lentiviral particles followed by 2-weeks selection with puromycin at 2 μg/ml. A shRNA sequence targeting the 3'UTR in human PDK1 (CGTGAATATGTTGAAGTAGAA) or empty pLKO lentivirus construct was used (Sigma-Aldrich). For reconstitution experiments, PC3 cells carrying stable shRNA knockdown of endogenous PDK1 were transfected with WT or phosphorylation-defective PDK1 T346A mutant cDNA followed by selection in the presence of G418 (500 μg/ml) for 2 weeks.

Mitochondrial Fractionation.

Mitochondrial fractions were prepared from PC3 cells using a Mitochondria Isolation Kit for Cultured Cells (Invitrogen). Briefly, PC3 cells were mechanically disrupted by 50 strokes with a Dounce homogenizer in isolation buffer containing 1 mM DTT plus protease inhibitor cocktail. Cell debris and nuclei were removed by centrifugation at 700 g for 10 min, and mitochondrial fractions were precipitated by centrifugation at 3,500 g for 20 min, followed by additional centrifugation at 11,000 g for 20 min. The final supernatant was used as isolated cytosol fractions. Submitochondrial fractions comprising outer membrane (OM), inner membrane (IM), inter-membrane space (IMS) and matrix were prepared as described in Kang (2007) Cell 131, 257-270.

Proteomics Studies: Identification of Proteins Overexpressed in Hypoxia Using 1D SDS Gel.

PC3 cells were maintained under normoxic or hypoxic conditions for 48 hr, solubilized in buffer containing 20 mM Tris, pH 7.5, 150 mM NaCl, 1 mM EDTA, 1 mM EGTA, 1% Triton X-100 and immunoprecipitated with Akt cons Ab for 18 h at 4° C. The various immunoprecipitates were collected using protein A-magnetic beads (Invitrogen) for 2 hr, washed five times and bound proteins were separated by SDS gel electrophoresis. The entire gel region between ~35 to ~120 kDa based on migration of standard proteins was cut into seven gel slices (Supplemental FIG. 2A) and digested with trypsin as described previously in Chae (2013) Nat Commun 4, 2139. Tryptic peptides were analyzed by LC-MS/MS on a Q Exactive Plus mass spectrometer (Thermo Scientific) coupled with a Nano-ACQUITY UPLC system (Waters). Samples were injected onto a UPLC Symmetry trap column (180 μm i.d.×2 cm packed with 5 μm C18 resin; Waters), and tryptic peptides were separated by RP-HPLC on a BEH C18 nanocapillary analytical column (75 μm i.d.×25 cm, 1.7 μm particle size; Waters) using a 95 min gradient. Eluted peptides were analyzed by the mass spectrometer set to repetitively scan m/z from 400 to 2000. The full MS scan was collected at 70,000 resolution followed by data-dependent MS/MS scans at 17,500 resolution on the 20 most abundant ions. Peptide match was set as preferred, the exclude isotopes option and charge-state screening were enabled to reject singly and unassigned charged ions.

MS/MS spectra were searched using the SEQUEST algorithm in BioWorks (version 3.3.1, Thermo Fisher Scientific) against the indexed human UniRef 100 protein database (September 2013). The reversed sequences of the database and a list of common contaminants were also appended. MS/MS spectra were searched using partial trypsin specificity with up to two missed cleavages, a 15 ppm precursor mass tolerance, 20 mmu fragment ion mass tolerance, static modification of cysteine by carbamidomethylation (+57.0215), and variable modifications for methionine oxidation (+15.9949), and asparagine deamidation (+0.9840). Consensus protein lists were generated by DTASelect v2.0 (Tabb, D. L. et al. (2002) J Proteome Res 1, 21-26) using the following data filter: 10 ppm precursor mass accuracy, ΔCn≥0.05, full tryptic specificity and requiring a minimum of two peptides per protein (Wang, H., et al. (2011) J Proteome Res 10, 4993-5005). The peptide false discovery rate was <1%. Hypoxia/normoxia protein-fold change was determined from the MS/MS spectra counts. To avoid division by zero while reflecting realistic minimal fold changes, proteins not found in normoxia were assigned a spectra count of "<1". Proteins with a minimum 4-fold change and at least 5 MS/MS spectra counts were considered high-confident overexpressed proteins. Mitochondrial proteins were identified by matching the protein ID against the integrated database maintained by MitoMiner (mitominer.mrc-mbu.cam.ac.uk/).

Silac Phosphoproteomics.

Proteins extracted from PC3 cells grown to equilibrium labeling in heavy (H)$^{13}C_6$-lysine $^{13}C_6$-arginine or light (L) $^{12}C_6$-lysine $^{12}C_6$-arginine SILAC medium were mixed. Two experimental samples normoxia (H)/hypoxia (L) and hypoxia (H)/normoxia (L), as well as a control normoxia (H)/normoxia (L) were analyzed. One mg of sample was solubilized in 8 M urea, 50 mM Tris-Cl (pH 8), 1 mM EDTA, 1% phosphatase inhibitors (Sigma), reduced with 5 mM DTT at 37° C. for 45 min, alkylated with 10 mM iodoacetamide at 37° C. for 30 min, and quenched with 10 mM cysteine at 37° C. for 30 min. The samples were then digested with modified trypsin (Promega; enzyme:protein=1:100) for 4 hr at a final urea concentration of 4 M, followed by overnight digestion at a final urea concentration of 2 M after adding another aliquot of trypsin. Tryptic peptides were subsequently desalted using Sep-Pak C18 (Waters). A replicate digest was also performed using the FASP method (Wisniewski, J. R., et al. (2009) Nat Methods 6, 359-362) for each sample. Phosphopeptides were enriched using the Titansphere™ Phos-TiO kit (GL Sciences Inc). Each sample was processed through two Phos-TiO spin tips in series according to the manufacturer's protocol, and subjected to duplicate LC-MS/MS analysis using a 4 hr gradient. For global proteome analysis without phosphopeptide enrichment, 35 µg of each sample was separated on a SDS-PAGE gel. Each gel lane was sliced into 11 equal fractions, digested with trypsin and analyzed by LC-MS/MS using a 95 min gradient.

SILAC data were analyzed with MaxQuant 1.4.1.2 (Cox (2008) Nat Biotechnol 26, 1367-1372). MS/MS data were searched against the human UniRef 100 protein database (September 2013) using full trypsin specificity with up to two missed cleavages, static carboxamidomethylation of Cys, and variable oxidation of: Met, protein N-terminal acetylation and phosphorylation on Ser, Thr and Tyr. Modified peptides were required to have a minimum score of 40. Consensus identification lists were generated with false discovery rates of 1% at protein, peptide and site levels. Reverse hits, contaminants, and identifications without any H/L ratio were removed from all datasets. Phosphopeptides were determined from the Phospho(STY)Sites and modification Specific Peptides tables. Identified phosphosites were also required to have a minimum localization probability of 0.75 and score difference of 5. Fold changes were calculated from the normalized Heavy/Light ratio. A 3 standard deviation (SD) cut-off was determined from the control normoxia (H)/normoxia (L) sample, and was used to identify sites displaying significant change in the experimental samples. Additional information on known phosphosite and phosphosite kinase was obtained from databases maintained at phosphosite.org through the Perseus software. For global proteome analysis, protein identifications were obtained from the protein Groups table, and were required to have at least two razor+unique peptides and a minimum ratio count of two. Fold changes of phosphosites were adjusted by the observed fold change of the respective protein in the global proteome comparison.

Identification of Thr346 Phosphorylation in PDK1.

Gel bands containing equal amount of PDK1 with no Akt phosphorylation, or following phosphorylation by active Akt1 or Akt2 in a kinase assay, were excised, digested with chymotrypsin at 0.02 µg/ml, and analyzed by LC-MS/MS using an 85 min gradient. MS/MS spectra were searched using SEQUEST against an indexed custom human UniRef 100 protein database (September 2013) containing the recombinant PDK1 sequence, reversed sequences and contaminants. Search parameters were used as described above, except the variable modifications interrogated were methionine oxidation (+15.9949), and phosphorylation (+79.9663) on Ser, Thr and Tyr. Consensus protein lists were generated by DTASelect using the following data filter: 10 ppm precursor mass accuracy of ΔCn≥0.05 (Wang, H., et al. (2011) J Proteome Res 10, 4993-5005). Sites were considered positive for Akt phosphorylation if they were identified by more than one MS/MS spectra count, and also not observed in PDK1 control samples. Identified phosphosite was verified by extracted ion chromatogram and manual inspection of MS/MS sequence assignment.

Molecular Modeling.

The structure of PDK1 (PDB code 2Q8F) containing the "ATP lid" (residues 336-356), was rendered using PyMOL software (DeLano Scientific). The ATP molecule was originated from the structure of PDK3-L2-ATP (PDB code 1Y8P), which was superposed onto the structure of PDK1 without the structure of PDK3-L2.

Kinase Assay.

Akt kinase assays were carried out according to the manufacturer's protocol (SignalChem). Briefly, 500 ng of purified PDK1 was incubated with 50 ng of active recombinant Akt for 20 min at 30° C. in buffer containing 5 mM MOPS, pH 7.2, 2.5 mM glycerophosphate, 5 mM $MgCl_2$, 1 mM EGTA, 0.4 mM EDTA, 0.25 mM DTT, and 200 µM ATP. Samples were separated on 10% SDS-polyacrylamide gels, transferred to nitrocellulose membranes, and analyzed with Akt cons Ab (RxRxxS/T), or phospho-specific antibody against T346 phosphorylated-PDK1 (pT346 Ab), by Western blotting. For Akt kinase assays using PDK1 mutant proteins, Flag-tagged WT or mutant PDK1 cDNA was transfected in PC3 cells. Forty-eight h after transfection, cells were lysed and incubated with anti-Flag affinity beads (Sigma Aldrich). To eliminate basal phosphorylation of PDK1, immunoprecipitated PDK1 proteins were dephosphorylated by incubation with 25 U of alkaline phosphatase (New England Biolabs) for 1 hr at 30° C. in 1 mg/ml BSA-containing reaction buffer. After washes in PBS, samples were analyzed in an Akt kinase assay as above.

In some experiments, samples incubated in Akt kinase assays were mixed with 1 µg of recombinant PDHE1α as a PDK1 substrate and further incubated for 5 min at 30° C. Alternatively, WT or mutant PDK1-Flag immunoprecipitates were washed in PBS, pH 7.2, and incubated with 1 µg recombinant PDHE1α in PDK1 kinase buffer containing 20 mM potassium phosphate, pH 7.5, 0.1 mM EDTA, 1 mM MgCl$_2$, 1 mM DTT and 200 µM ATP for 5 min at 30° C. At the end of the incubation, samples were separated by SDS gel electrophoresis and analyzed using antibodies to PDHE1α or phospho-PDHE1α (Ser293), by Western blotting.

PDH Activity Assay.

Enzyme activity was quantified using a microplate assay kit, according to the manufacturer's specifications (Abcam). Briefly, PC3 cells were lysed and centrifuged at 1,000 g for 10 min at 4° C., and aliquots of the supernatants were loaded on anti-PDH antibody-coated 96-well plates. PDH complex enzyme activity, which converts pyruvate to acetyl-CoA in the presence of CoA, was measured by reduction of NAD$^+$ to NADH coupled to the reduction of a reporter dye, and quantified by changes in absorbance at 450 nm for 2 hr at 1 min or 2 min intervals using a plate reader (Beckman Coulter). The rates of activity were expressed in bar graphs as changes in milliOD/min between the start and end points of the measurement.

Analysis of Bioenergetics.

Glucose concentrations were determined in cell culture medium of PC3 transfectants using a glucose kit (Sigma-Aldrich). Briefly, 2×10$^6$ cells were seeded in 10 cm$^2$ tissue culture dishes for 48 hr, and 200 µl aliquots of culture medium were incubated with 1 ml assay mixture, containing 1.5 mM NAD, 1 mM ATP, 1.0 U/ml hexokinase, and 1.0 U/ml G6PDH. Glucose concentrations were determined by measuring the amount of reduced NAD to NADH by G6PDH, and quantified by absorbance at 340 nm. Extracellular lactate concentrations were measured in PC3 cells using a colorimetric assay (Abcam), with quantification of lactate-dependent conversion of NADP to NADPH in the presence of excess lactate dehydrogenase (LDH) by absorbance at 450 nm. Intracellular ATP concentrations were determined by a luciferin-luciferase method using a microplate luminometer (Beckman Coulter) against standard ATP solutions as reference. For oxygen consumption, reconstituted PC3 cells were plated on black-body, clear bottom 96-well plates, and incubated with an oxygen-sensing probe (10 pmol/well). One hundred µl of heavy mineral oil was added to each well to seal the samples from ambient oxygen, and oxygen consumption was determined at increasing time intervals at 37° C. by quantifying the probe fluorescence signal in each well with excitation and emission wavelengths at 370 nm and 625 nm, respectively.

Autophagy.

PC3 cells transfected with various cDNA constructs were fixed in 4% formaldehyde/PBS for 15 min at 22° C., washed, permeabilized with 0.1% Triton X-100/PBS for 5 min, washed, and blocked with 10% normal goat serum/PBS for 1 hr. After washing, cells were incubated with an antibody to LC3-II XP (Cell Signaling) diluted 1:200 in 1% BSA/0.3M glycine/PBS overnight at 4° C. Slides were washed and mounted in DAPI-containing Prolong Gold mounting medium (Invitrogen). At least 20 random fields from 2 independent experiments were analyzed by fluorescence microscopy using a Nikon E600 microscope. A minimum of 280 cells were analyzed to obtain mean values.

Colony Formation Assay.

For analysis of colony-forming ability, 400 PC3 cells were plated in triplicate in 6-multiwell plates. The growth medium was changed twice for a week, then colonies were washed in PBS and fixed/stained for 30 min in 0.5% w/v crystal violet/methanol. Plates were rinsed in tap water and dried before scoring. Macroscopically visible colonies were manually counted.

ROS Measurement.

To detect cellular ROS, PC3 cells were incubated with 5 µM of CellROX Green Reagent (Invitrogen) according to the manufacturer's instructions for 30 min at 37° C. After three washes in PBS, pH 7.4, cells were harvested and analyzed on a FACS Calibur flow cytometer, placing the CellROX Green Reagent signal in FL1. Intact cells were gated in the FSC/SSC plot to exclude small debris. The resulting FL1 data were plotted on a histogram.

Optical Imaging Studies.

For detection of bioluminescence, mice were anesthetized with 4% chloral hydrate v/v (Sigma Aldrich) and then injected intraperitoneally with 150 mg/kg of luciferin (Beetle Luciferin potassium salt, Promega). A bioluminescence signal was quantified after biodistribution, in vivo using the non-invasive optical imaging system, IVIS SPECTRUM/CT (PerkinElmer LifeSciences). The mCherry signal was acquired in the same animals (excitation, 605; emission, 660) using an IVIS imaging system. Animals were also co-injected i.v. with 2 nmol of HypoxiSense680 fluorescent probe, a carbonic anhydrase IX (CAIX)-targeted fluorescent in vivo imaging agent. After 24 hr, mice were analyzed by fluorescence imaging using the following filters, excitation, 640; emission, 700 and excitation, 745; emission, 800. Images were analyzed and scaled after completion of all acquisitions, using an appropriate computer software (Living Image Software; PerkinElmer LifeSciences). The same region of interest (ROI) was applied to all images. For bioluminescence quantification (luciferase), data were expressed as average radiance (photons/second/cm$^2$/steradian), which is a calibrated measurement of photon emission. For fluorescence quantification (mCherry and HypoxiSense probe), data were expressed as Average Radiant Efficiency [(p/s/cm$^2$/sr)/(µW/cm$^2$)], which is a further correction of fluorescent signal detected in each sample, taking into account the intensity for the incident excitation light that is not uniform over the field of view.

Bioinformatics Analysis.

Phosphorylation fold changes were calculated as average fold change across all experiments that showed significant differences or across all experiments if none were significant. The fold changes were then normalized by the global protein expression difference to identify true level of phosphorylation changes. Signal intensity was calculated as a sum of intensities across all experiments. Final list of differentially phosphorylated sites included only sites that were detected as significant (1.6 fold as described above in proteomics section) between normoxia and hypoxia and after correction for global protein expression (at least 1.5-fold difference). Each detected protein's phosphorylation site was annotated with kinases known to target the site through PhosphoSite database (phosphosite.org) using Signaling kinase substrate dataset (dated Sep. 3, 2014). The final protein list for gene network analysis with Ingenuity Pathway Analysis (IPA) software (IPA®, QIAGEN Redwood City, qiagen.com/ingenuity) was extended to include unique proteins with differential phosphorylation as detected by analysis on peptide level and additional unique proteins significantly differentially expressed as detected by global protein expression. Known mitochondrial proteins were identified using information from 3 sources: (1) products with gene ontology annotation GO:0005739 AmiGO (godatabase.org), (2) mitochondrial proteins from Mitominer (mitominer.mrc-mbu.cam.ac.uk) and (3) from Integrated Mitochondrial Protein Index (IMPI) database which includes mitocarta and Mitoprotein database (mitoproteome.org).

IPA Knowledgebase was used to find all mitochondrial functions and diseases and connect significantly affected proteins into a network that also included known mitochondrial proteins determined by the three sources described above. Enrichment analysis of the list of proteins that significantly changed phosphorylation or global expression in response to hypoxia was performed by IPA using "Canonical Pathways" and "Functions" analyses options. Pathways and functions with p-value<$10^{-6}$ that had predicted activation state (Z-score of at least >0.2) are reported.

Patients. A first cohort of 26 patients diagnosed with de novo glioma were enrolled at Fondazione IRCCS Ca' Granda Ospedale Maggiore Policlinico (Milan, Italy) between 2010 and 2011, and described previously (Di Cristofori (2015) Oncotarget 6, 17514-17531). All patients were treated with surgical resection with curative intent. Gliomas were staged according to the WHO classification (Louis (2007) Acta Neuropathol 114, 97-109.), and the clinicopathological and molecular characteristics of the patients' series used in this study are described in Table 1 below. This cohort was used to evaluate the expression of phosphoT346-PDK1 (pPDK1), phosphoPDHE1α (pPDHE1), phosphoT416-Src (pSrc) and nuclear HIF1α reactivity, by immunohistochemistry. Tissue microarrays (TMAs) of glioma or normal brain tissues were as described (Di Cristofori, A. et al. (2015) Oncotarget 6, 17514-17531). Immunohistochemistry slides were digitalized using an Aperio scanner at 20× magnification, and HIF1α nuclear staining was quantified using a nuclear-specific algorithm implemented in Genie Histology Pattern Recognition software (Aperio, Leica Microsystems). To specifically quantify nuclear HIF1α expression in primary GBM culture, the Velocity algorithm that counts and displays red signals (HIF1 α) within the Hoechst signal (nuclei) in each z-stack was used. A second series of 116 patients with de novo glioma who underwent surgery with curative intent between 2008 and 2009 and for which complete clinical and follow-up records were available (Table 3 below), was retrieved from the archives of the Pathology Division. This cohort was used in the present study to correlate the expression of Akt-phosphorylated PDK1 on T346 with prognostic markers of glioma progression, including nuclear HIF1α, MGMT promoter methylation and IDH1 mutational status (wild type (WT)/R132H), and patients' overall survival.

TABLE 1

Clinico-pathological characteristics of the first patient cohort examined in this study.

| Patient ID | Sex | Age (y) | Grade | Ki-67 (%) | HIF1α (%) | HIF1α score | p-PDK1 | p-PDHE | MGMT | IDH1 |
|---|---|---|---|---|---|---|---|---|---|---|
| Astr 1 | M | 53 | II | 4 | 0.66 | NEG | 0 | 0 | M | R132H |
| Astr 2 | F | 74 | II | 5 | 0.74 | NEG | 0 | 0 | UM | WT |
| GBM 1 | F | 61 | IV | 30 | 1.75 | 1 | 1 | 0 | M | WT |
| GBM 2 | F | 30 | IV | 12 | 1.64 | 1 | 2 | 2 | UM | R132H |
| GBM 3 | M | 59 | IV | — | 1.74 | 1 | 1 | 1 | M | R132H |
| GBM 4 | F | 60 | IV | 10 | 1.47 | 1 | 1 | 2 | M | WT |
| GBM 5 | F | 77 | IV | 10 | 6.66 | 2 | 1 | 1 | M | WT |
| GBM 6 | M | 78 | IV | — | 3.50 | 2 | 2 | 1 | M | R132H |
| GBM 7 | M | 69 | IV | 10 | 3.33 | 2 | 2 | 2 | M | WT |
| GBM 8 | F | 68 | IV | — | 3.47 | 2 | 1 | 1 | UM | WT |
| GBM 9 | M | 63 | IV | 18 | 2.09 | 2 | 1 | 2 | UM | WT |
| GBM 10 | M | 48 | IV | 7.5 | 2.06 | 2 | 1 | 0 | M | R132H |
| GBM 11 | M | 51 | IV | 8 | 2.53 | 2 | 2 | 2 | M | WT |
| GBM 12 | F | 55 | IV | — | 5.97 | 2 | 2 | 2 | M | WT |
| GBM 13 | M | 30 | IV | 11 | 2.28 | 2 | 1 | 1 | M | R132H |
| GBM 14 | M | 45 | IV | 7 | 3.26 | 2 | 2 | 1 | UM | WT |
| GBM 15 | M | 69 | IV | 9 | 5.40 | 2 | 1 | 1 | UM | WT |
| GBM 16 | M | 35 | IV | 8 | 4.37 | 2 | 1 | 1 | UM | WT |
| GBM 17 | F | 77 | IV | 11 | 2.49 | 2 | 1 | 0 | UM | R132H |
| GBM 18 | F | 70 | IV | 8 | 4.16 | 2 | 2 | 1 | M | WT |
| GBM 19 | M | 61 | IV | — | 0.04 | NEG | 0 | 0 | M | WT |
| GBM 20 | M | 69 | IV | 9 | 0.41 | NEG | 0 | 0 | UM | WT |
| GBM 21 | M | 35 | IV | 15 | 0.51 | NEG | 1 | 0 | M | R132H |
| GBM 22 | M | 60 | IV | — | 0.61 | NEG | 0 | 0 | UM | WT |
| GBM 23 | F | 49 | IV | — | 0.18 | NEG | 1 | 0 | M | R132H |
| GBM 24 | F | 61 | IV | 8 | 0.90 | NEG | 0 | 0 | UM | WT |

Astr, Astrocytoma;
GBM, glioblastoma;
M, male;
F, female;
MGMT, $O^6$-methylguanine-DNA-methyltransferase;
UM, unmethylated;
M, methylated;
IDH1, cytosolic isocitrate dehydrogenase-1

Xenograft Tumor Growth Studies.

In a first set of experiments, PC3 cells stably transduced with control pLKO or PDK1-directed shRNA were reconstituted with vector, WT PDK1 or T346A PDK1 mutant cDNA at 80% confluency, suspended in PBS, pH 7.4, and injected (0.2 ml containing 2×$10^6$ cells) s.c. into the flank of 6-8 week old male NOD SCIDγ (NSG, NOD.Cg-Prkdc$^{scid}$Il2rg$^{tm1Wjl}$/SzJ) immunocompromised mice (Jackson Laboratory, 3 mice per condition/2 tumors per mouse). The width and length of superficial tumors were measured with a caliper at the indicated time intervals, and tumor volume was calculated according to the formula Vol=width$^2$×length/2. After 21 days Xenograft tumors were harvested, fixed and processed for immunohistochemistry.

An orthotopic murine model of glioblastoma (GBM) was obtained by stereotactic injection (coordinates: 1.5 mm lateral to the bregma, 0 mm behind and 3.0 mm ventral to the dura) (Maes, W. et al. (2009) J Neurooncol 91, 127-139.) of 1×$10^5$U251-HRE-mCherry GBM cells in 2 μl of PBS into 7-8-week-old female nude mice (Harlan Laboratories) at day 0 (Lo Dico (2014) Mol Imaging Biol 16, 210-223). Following surgery, mice were monitored for recovery until complete awakening. Six animals per time point were used and mice were euthanized after 20 or 34 days. Intracranial GBM samples were harvested from the various groups and processed for differential expression of phosphorylated PDK1 or PDHE1, HIF1α or Ki-67 by immunohistochemistry on serial sections.

Statistical Analysis.

Data were analyzed using the two-sided unpaired t or chi-square tests using a GraphPad software package (Prism 6.0) for Windows. Correlation parameters between immunohistochemical (IHC) scores in glioma patients and clinicopathological variables were derived using Mann-Whitney U test or chi-square test for continuous or discrete variable, respectively, using GraphPad Prism or MedCalc (Mariakerke, Belgium) statistical package. Receiver operating characteristics (ROC) curves method was used to test the accuracy of T346 phosphorylated PDK1 to correctly discriminate between glioma patients according to their survival status (alive or dead for the disease) and to generate cut-offs for phosphorylated PDK1 IHC score using the non-arbitrary criterion derived from the Youden's statistic (J, MedCalc Software) as described (Di Cristofori (2015) Oncotarget 6, 17514-17531). The pPDK1 IHC score value that more accurately discriminated between alive or dead patients was >25 and >40 for gliomas or GBM patients, respectively (Youden criterion). Glioma patients were then sorted into low or high-expressor categories and Kaplan-Meier survival curves were compared using the Log-Rank test (MedCalc Software). Data are expressed as mean±SD or mean±SEM of replicates from a representative experiment out of at least two or three independent determinations. A p value of <0.05 was considered as statistically significant.

Example 1: A Mitochondrial Akt Phosphoproteome in Hypoxia

The mitochondrial phosphoproteome of prostate adenocarcinoma PC3 cells exposed to severe hypoxia (<0.5% oxygen for 48 hr) versus normoxia was profiled. A total of 4,236 phosphosites were identified in the phosphopeptide-enriched samples, with a large number of changes in phosphorylation level in hypoxia/normoxia samples (FIGS. 1A and S1A). In total, 1,329 phosphosites showed a significant change (minimum fold-change of 1.6) in at least one sample analyzed (FIG. 1A). By bioinformatics analysis, the mitochondrial phosphoproteome in hypoxia contained regulators of organelle integrity, bioenergetics, gene regulation and proteostasis (FIG. 1B), which are functionally implicated in tumor cell proliferation, motility, invasion and apoptosis (FIG. 9B). To complement these data, changes in the global mitochondrial proteome were examined in hypoxia versus normoxia. A total of 5,583 proteins were identified in this analysis, and 267 of these proteins showed a significant change in hypoxia/normoxia samples (FIG. 9C). Many of the phosphosites were not modulated at the protein level, suggesting that these phosphorylation events were independent of protein expression. In addition, the hypoxia-regulated mitochondrial phosphoproteome contained a discrete "Akt signature" (FIG. 1A), characterized by increased phosphorylation of six Akt target proteins in hypoxia versus normoxia (FIG. 1C).

Based on these results, a role of Akt in the tumor response to hypoxia was also observed. Exposure of PC3 cells to hypoxia resulted in increased recruitment of Akt to mitochondria, whereas the cytosolic levels of Akt were unchanged between hypoxia and normoxia (FIGS. 1D and S1D). The hypoxia-regulated pool of mitochondrial Akt was "active" as it was phosphorylated on Ser473 (FIG. 1D) and persisted for up to 24 hr after re-oxygenation (FIGS. 1E and S1E). Consistent with these results, hypoxia was accompanied by increased phosphorylation of a set of mitochondrial proteins recognized by an antibody to the Akt consensus phosphorylation sequence, RxRxxS/T (Akt cons Ab) (FIG. 1F).

Preincubation of mitochondrial extracts with Akt cons Ab (FIG. 1F), or silencing Akt2 by small interfering RNA (siRNA) (FIG. 9F), removed the mitochondrial proteins recognized by Akt cons Ab in hypoxia, confirming the specificity of this response and Akt-directed phosphorylation activity in mitochondria in hypoxia. Silencing Akt1 had minimal effect (FIG. 9F). siRNA silencing of HIF1α did not affect Akt recruitment to mitochondria in hypoxia (FIG. 9G), suggesting that this pathway did not require HIF1-dependent transcription. In addition, depletion of HIF1α did not affect Akt levels in the cytosol or mitochondria under normoxic conditions, whereas phosphorylated Akt2 levels were increased in the cytosol in response to hypoxia (FIG. 9G). As detected by Akt cons Ab, the expression levels of downstream Akt-phosphorylated target molecules were unchanged in normoxic or hypoxic conditions (FIG. 1F). In response to hypoxia, active Akt was found predominantly in the mitochondrial inner membrane, and, to a lesser extent, the matrix (FIG. 9H).

The mechanism(s) of how Akt is recruited to mitochondria in hypoxia was further investigated. Blocking the chaperone activity of heat shock protein-90 (Hsp90) with 17-allylaminogeldanamycin (17-AAG) prevented the accumulation of mitochondrial Akt in hypoxia (FIG. 1G). Also, scavenging mitochondrial ROS with MitoTempo (MT) inhibited Akt recruitment to mitochondria (FIG. 1H). The antioxidant N-acetyl cysteine (NAC) had no effect (FIG. 1H), identifying mitochondria-derived ROS as a critical stimulus for mitochondrial accumulation of Akt in hypoxia.

Example 2: PDK1 is a Phosphorylation Target of Mitochondrial Akt in Hypoxia

A 1D proteomics screen was set up to identify mitochondrial proteins phosphorylated by Akt in hypoxia (FIG. 2A). Immune complexes precipitated with Akt cons Ab from normoxic or hypoxic PC3 cells contained bands with ~35 to ~120 kDa molecular weight that were more abundant in hypoxia (FIG. 10A). Preclearing mitochondrial extracts with Akt cons Ab removed most of these proteins, validating the specificity of the immunoprecipitation step. From these experiments, by mass spectrometry, 84 high-confidence Akt substrates differentially expressed in hypoxia (Table 2 below) were identified.

TABLE 2

High-confidence overexpressed proteins identified in hypoxia versus normoxia.

| ID | Gene name | MW | Spectra Count Normoxia | Spectra Count Hypoxia | Hypoxia/ Normoxia Fold Change |
|---|---|---|---|---|---|
| Known Mitochondrial Proteins Identified | | | | | |
| Q92797 | SYMPK | 141,148 | 1 | 5 | 5.0 |
| Q86W56 | PARG | 111,110 | 1 | 5 | 5.0 |
| P36776 | LONP1 | 106,489 | 4 | 23 | 5.8 |

TABLE 2-continued

High-confidence overexpressed proteins identified in hypoxia versus normoxia.

| ID | Gene name | MW | Spectra Count Normoxia | Spectra Count Hypoxia | Hypoxia/Normoxia Fold Change |
|---|---|---|---|---|---|
| P52789 | HK2 | 102,380 | 12 | 64 | 5.3 |
| Q86VP1 | TAX1BP1 | 90,877 | 0 | 5 | >5* |
| P13674 | P4HA1 | 61,049 | 0 | 9 | >9* |
| Q16851 | UGP2 | 56,940 | 1 | 11 | 11.0 |
| Q96HE7 | ERO1L | 54,393 | 0 | 10 | >10* |
| P11166 | SLC2A1 | 54,084 | 0 | 15 | >15* |
| Q6YP21 | CCBL2 | 51,400 | 0 | 6 | >6* |
| P36551 | CPOX | 50,152 | 2 | 8 | 4.0 |
| Q15118 | PDK1 | 49,244 | 2 | 11 | 5.5 |
| Q9Y305-2 | ACOT9 | 46,355 | 1 | 7 | 7.0 |
| Q9NX46 | ADPRHL2 | 38,947 | 0 | 7 | >7* |
| Q5T440 | IBA57 | 38,155 | 1 | 5 | 5.0 |
| P62937 | PPIA | 18,012 | 1 | 6 | 6.0 |
| Additional Proteins Identified** | | | | | |
| Q9P2R6 | RERE | 172,423 | 1 | 5 | 5.0 |
| Q96ST3 | SIN3A | 145,175 | 0 | 6 | >6* |
| O60841 | EIF5B | 138,827 | 1 | 6 | 6.0 |
| O95819-2 | MAP4K4 | 138,417 | 2 | 9 | 4.5 |
| Q9Y4H2 | IRS2 | 137,334 | 0 | 7 | >7* |
| P00533 | EGFR | 134,277 | 9 | 36 | 4.0 |
| Q6ZS17-3 | FAM65A | 133,426 | 0 | 5 | >5* |
| Q14203-2 | DCTN1 | 127,404 | 1 | 5 | 5.0 |
| Q9Y3M8-2 | STARD13 | 123,893 | 0 | 7 | >7* |
| O14776-2 | TCERG1 | 121,690 | 0 | 7 | >7* |
| O75044 | SRGAP2 | 120,880 | 2 | 10 | 5.0 |
| O95486 | SEC24A | 119,749 | 1 | 9 | 9.0 |
| A0AVT1 | UBA6 | 117,970 | 1 | 6 | 6.0 |
| Q9NWH9 | SLTM | 117,149 | 0 | 5 | >5* |
| Q6PJG2 | ELMSAN1 | 114,989 | 1 | 25 | 25.0 |
| O94855-2 | SEC24D | 113,081 | 0 | 5 | >5* |
| Q75QN2-2 | INTS8 | 111,115 | 1 | 6 | 6.0 |
| O14974-4 | PPP1R12A | 109,104 | 1 | 7 | 7.0 |
| P19838-2 | NFKB1 | 105,427 | 1 | 5 | 5.0 |
| Q9BZQ8 | FAM129A | 103,135 | 0 | 5 | >5* |
| Q05086-3 | UBE3A | 100,102 | 1 | 5 | 5.0 |
| Q9ULJ3-2 | ZBTB21 | 95,807 | 0 | 5 | >5* |
| Q9Y5B0-4 | CTDP1 | 93,485 | 1 | 5 | 5.0 |
| Q9H5V8 | CDCP1 | 92,932 | 3 | 15 | 5.0 |
| Q9Y597 | KCTD3 | 88,984 | 1 | 8 | 8.0 |
| O00469-2 | PLOD2 | 87,098 | 2 | 12 | 6.0 |
| Q8TED9-2 | AFAP1L1 | 81,750 | 0 | 5 | >5* |
| Q8IVL5 | LEPREL1 | 80,985 | 0 | 7 | >7* |
| Q8N556 | AFAP1 | 80,725 | 2 | 10 | 5.0 |
| P48147 | PREP | 80,700 | 0 | 5 | >5* |
| Q04446 | GBE1 | 80,474 | 2 | 9 | 4.5 |
| Q684P5 | RAP1GAP2 | 80,056 | 3 | 14 | 4.7 |
| Q8IZ21-2 | PHACTR4 | 79,129 | 2 | 8 | 4.0 |
| P49761 | CLK3 | 73,515 | 3 | 15 | 5.0 |
| Q9NQW7-2 | XPNPEP1 | 67,227 | 1 | 7 | 7.0 |
| Q5T1V6-2 | DDX59 | 64,572 | 1 | 5 | 5.0 |
| Q96DX4 | RSPRY1 | 64,180 | 0 | 5 | >5* |
| Q9P270 | SLAIN2 | 62,543 | 1 | 6 | 6.0 |
| Q01201 | RELB | 62,135 | 1 | 5 | 5.0 |
| Q5NKV8 | ICAM1 | 57,882 | 1 | 8 | 8.0 |
| P31751 | AKT2 | 55,769 | 1 | 6 | 6.0 |
| P43490 | NAMPT | 55,521 | 3 | 14 | 4.7 |
| Q15750 | TAB1 | 54,644 | 2 | 10 | 5.0 |
| Q16877 | PFKFB4 | 54,040 | 1 | 7 | 7.0 |
| Q13424 | SNTA1 | 53,895 | 1 | 5 | 5.0 |
| O75312 | ZNF259 | 50,925 | 1 | 6 | 6.0 |
| Q9UJM3 | ERRFI1 | 50,560 | 1 | 10 | 10.0 |
| P14921 | ETS1 | 50,408 | 0 | 7 | >7* |
| O15427 | SLC16A3 | 49,469 | 2 | 16 | 8.0 |
| P05455 | SSB | 46,837 | 3 | 12 | 4.0 |
| Q13077 | TRAF1 | 46,164 | 2 | 10 | 5.0 |
| Q9GZT9 | EGLN1 | 46,021 | 2 | 9 | 4.5 |
| Q96QF0-4 | RAB3IP | 45,217 | 1 | 6 | 6.0 |
| Q9BY76 | ANGPTL4 | 45,214 | 0 | 6 | >6* |
| Q92597 | NDRG1 | 42,835 | 6 | 57 | 9.5 |
| P52788 | SMS | 41,268 | 0 | 6 | >6* |
| Q9H410 | DSN1 | 40,067 | 1 | 5 | 5.0 |
| P08397 | HMBS | 39,330 | 1 | 7 | 7.0 |
| Q9NXG2 | THUMPD1 | 39,315 | 1 | 5 | 5.0 |
| Q6ZSR9 | | 37,976 | 2 | 12 | 6.0 |
| Q9Y576 | ASB1 | 37,014 | 1 | 6 | 6.0 |
| P17676 | CEBPB | 36,106 | 1 | 6 | 6.0 |
| Q53FA7 | TP53I3 | 35,536 | 1 | 5 | 5.0 |
| Q9HC38-2 | GLOD4 | 33,233 | 2 | 8 | 4.0 |
| Q14135-4 | VGLL4 | 31,883 | 1 | 5 | 5.0 |
| Q9Y3A2 | UTP11L | 30,447 | 1 | 5 | 5.0 |
| Q9BVG4 | PBDC1 | 26,057 | 1 | 5 | 5.0 |
| Q9NZT1 | CALML5 | 15,892 | 1 | 8 | 8.0 |

*To determine a realistic minimum fold change, a normoxia spectra count of <1 was assigned.
**The presence of cytosolic proteins may reflect a low level contamination of mitochondrial extracts with cytosolic fractions.

Sixteen of these molecules were known mitochondrial proteins (FIG. 2B), including hypoxia- and HIF1-regulated effectors of bioenergetics (UGP2, SLC2A1, PDK1, HK2), extracellular matrix remodeling (P4HA1), $Ca^{2+}$ homeostasis at the ER-mitochondria interface (Ero1L), oxidative phosphorylation (LonP1, IBA57), and metabolism (Acot9). Due to previously published work suggesting the importance of PDK1 in the tumor hypoxic response, PDK1 was experimented as a potential substrate of mitochondrial Akt in hypoxia. In kinase assays, active Akt1 or Akt2 readily phosphorylated PDK1, as well as control GSK3α, as determined by Western blotting with Akt cons Ab (FIG. 2C). This phosphorylation event was selective for PDK1, as related PDK2, PDK3 or PDK4 isoforms were unreactive (FIG. 2D). In addition, PDK1 immune complexes reacted with Akt cons Ab preferentially in hypoxia (FIG. 2E), and reciprocally, immune complexes precipitated with Akt cons Ab in hypoxia contained PDK1 (FIG. 10B), consistent with the model of Akt phosphorylation of PDK1 in hypoxia.

Potential Akt phosphorylation sites was observed in PDK1 by LC-MS/MS analysis of chymotrypsin digests of Akt-phosphorylated PDK1 in a kinase assay separated by SDS-PAGE (FIG. 10C). Thr346 (T346) was identified in a number of PDK1 chymotryptic peptides, including the sequence STAPRPRVEpTSRAVPL (m/z=908.9751) as the sole phospho-amino acid modified by Akt1 or Akt2, compared to control (FIG. 2F). The PDK1 sequence surrounding T346 matched an Akt consensus phosphorylation site, RxRxxS/T (FIG. 10D), which was not present in PDK2, PDK3 or PDK4 (FIG. 10E). Consistent with these data, active Akt2 phosphorylated wild type (WT) PDK1 but not a phosphorylation-defective Thr346→Ala (T346A) PDK1 mutant in transfected PC3 cells (FIG. 2G). In the PDK1 crystal structure, T346 is predicted to localize to a flexible, "ATP lid" hinge region (FIG. 2H), positioned to affect ATP loading and kinase activation.

To independently validate these findings, a phosphospecific antibody to phosphorylated T346 (pT346 Ab) in PDK1 was generated. The pT346 Ab dose-dependently reacted with the phosphorylated PDK1 peptide CAPRPRVE(pT)SRAVPLA (SEQ ID NO: 5), but not the non-phosphorylated sequence (FIG. 10F). A second antibody raised against the non-phosphorylated sequence recognized the non-phosphorylated PDK1 peptide (FIG. 10G). Under these conditions, pT346 Ab reacted with Akt2-phosphorylated WT PDK1, but not T346A PDK1 mutant (FIG. 2I). Consistent with the model that T346 phosphorylation is hypoxia-sensitive, WT PDK1, but not T346A PDK1, precipitated from hypoxic PC3 cells reacted with pT346 Ab (FIG. 2J). pT346 Ab only weakly reacted with WT or T346A PDK1 precipitated from normoxic cells (FIG. 2J).

Finally, clones of PC3 cells stably silenced for endogenous PDK1 by short hairpin RNA (shRNA) were generated. pT346 Ab did not react with these cells in normoxia (FIG. 10H). In contrast, pLKO transfectants reacted with pT346 Ab in hypoxia, and this response was abolished by shRNA silencing of PDK1 (FIG. 10H).

Example 3: Akt-PDK1 Phosphorylation Axis in Hypoxia

Expression of WT PDK1 in hypoxic PC3 cells increased the phosphorylation of the E1α catalytic subunit (PDHE1) of the PDC (FIG. 3A) on site 1 (Ser264 in the mature protein), one of three regulatory phosphorylation sites (Patel, M. S., Nemeria, N. S., Furey, W., and Jordan, F. (2014). The pyruvate dehydrogenase complexes: structure-based function and regulation. J Biol Chem 289, 16615-16623). Conversely, expression of T346A PDK1 mutant reduced PDHE1 phosphorylation in hypoxia (FIG. 3A), and no PDHE1 phosphorylation was detected in normoxia (FIG. 3A). Immune complexes of WT or T346A PDK1 mutant contained comparable amounts of the PDC component, PDHE1α, suggesting that T346 does not contribute to a PDK1-PDC complex (FIG. 11A). In a kinase assay, active Akt2 increased PDK1 phosphorylation of PDHE1 (FIG. 3B). While WT PDK1 phosphorylated PDHE1 in the presence of Akt2 (FIG. 3C), T346A PDK1 mutant was ineffective (FIG. 3C). Consistent with these data, increased PDHE1 phosphorylation was detected only in the presence of Akt2 and PDK1, but not PDK2, PDK3 or PDK4 (FIG. 11B). Silencing of Akt2 inhibited PDHE1 phosphorylation in hypoxia, whereas Akt1 knockdown only had a partial effect (FIG. 3D). As a complementary approach, a pan-Akt small molecule inhibitor, MK2206, which indistinguishably suppressed Akt phosphorylation in hypoxia and normoxia was used (FIG. 11C). Incubation of PC3 cells with MK2206 suppressed PDHE1 phosphorylation in hypoxia (FIG. 3E). This response was specific because PDK1 immunoprecipitated from MK2206-treated cells also failed to phosphorylate PDHE1 in a kinase assay in hypoxia (FIG. 11D). In normoxia, MK2206 had no effect on PDHE1 phosphorylation in cell extracts (FIG. 3E) or in a kinase assay with immunoprecipitated PDK1 (FIG. 11D), validating the specificity of Akt-directed phosphorylation in hypoxic conditions.

As an independent approach, WT or kinase-dead (KD) Akt2 constructs targeted to the mitochondria by the cytochrome c oxidase subunit 8 mitochondrial import sequence were generated. Similar to the endogenous protein, mitochondrial-targeted Akt2 accumulated in the various submitochondrial fractions (FIG. 11E). Functionally, mitochondrial-targeted Akt2-KD inhibited PDHE1 phosphorylation in hypoxic PC3 cells (FIG. 3F), whereas non-mitochondrial targeted Akt2-KD had no effect. There was no PDHE1 phosphorylation in the cytosol of hypoxic or normoxic tumor cells, and Akt2-KD or mitochondrial-targeted Akt2-KD had no effect in these settings (FIG. 11F). Reciprocally, forced expression of mitochondrial-targeted WT Akt2 was sufficient to increase PDHE1 phosphorylation even in the absence of hypoxia (FIG. 11G).

Finally, PDK1-depleted cells were reconstituted with various PDK1 cDNAs. Expression of WT PDK1 in these settings restored PDHE1 phosphorylation in hypoxia, whereas T346A PDK1 mutant had no effect (FIG. 3G). With respect to its enzymatic function, PDK1 knockdown increased PDH activity in normoxic PC3 cells (FIG. 3H). Hypoxic cells showed reduced PDH activity, and this response was partially rescued by shRNA silencing of PDK1 (FIG. 3H). Reconstitution of these cells with WT PDK1, but not T346A PDK1 mutant, suppressed PDH activity in hypoxia (FIG. 3I). In addition, expression of Akt-KD or mitochondrial-targeted Akt-KD in PC3 cells had no effect on PDH activity in normoxia, but modestly elevated PDH function in hypoxia (FIG. 11H), consistent with loss of an Akt-regulated inhibitory function of PDK1 in these settings. Vector or non-mitochondrial targeted Akt2-KD had no effect (FIG. 11H).

Example 4: Mitochondrial Akt-PDK1 Phosphorylation Controls Tumor Metabolic Reprogramming To understand how mitochondrial Akt-PDK1 signaling affects tumor behavior, potential changes in cancer metabolism were observed. Consistent with previous studies, hypoxia stimulated glycolytic metabolism in tumor cells, characterized by increased glucose consumption (FIG. 3J) and lactate production (FIG. 3K). Mitochondrial Akt-PDK1 signaling was important for this response, as PDK1 knockdown reduced glucose consumption in hypoxia, whereas reconstitution of targeted cells with WT PDK1, but not T346A PDK1 mutant, restored glycolysis (FIG. 3J). Similarly, Akt inhibition with MK2206 (FIG. 3K) or silencing of Akt2 (FIG. 3L) impaired metabolic reprogramming, reducing lactate production in hypoxia. Normoxic cultures were not affected (FIGS. 3K and 3L), and Akt1 knockdown had only partial effect (FIG. 3L). Consistent with a metabolic switch towards glycolysis (Kim, J. W., Tchernyshyov, I., Semenza, G. L., and Dang, C. V. (2006). HIF-1-mediated expression of pyruvate dehydrogenase kinase: a metabolic switch required for cellular adaptation to hypoxia. Cell Metab 3, 177-185.), PC3 cells reconstituted with WT PDK1 exhibited reduced oxygen consumption, a marker of oxidative phosphorylation, whereas expression of T346A PDK1 mutant restored oxygen consumption (FIG. 3M), further supporting a role of mitochondrial Akt-PDK1 signaling in hypoxic metabolic reprogramming.

Example 5: Mitochondrial Akt-PDK1 Phosphorylation In Vivo

When analyzed in time-course experiments, hypoxia increased phosphorylation of Akt1 and Akt2, as well as PDHE1 starting at 3 and 6 hr, respectively (FIG. 12A). The overall hypoxic response under these conditions was cell type-specific. Akt inhibition strongly reduced PDHE1 phosphorylation in prostate adenocarcinoma (DU145), lung adenocarcinoma (A549) and glioblastoma (LN229), but had no effect on PDHE1 phosphorylation in breast adenocarcinoma cells MCF-7 (ER$^+$) or MDA-231 (ER$^-$) (FIG. 12B). Knockdown of PTEN in MCF-7 cells increased PDHE1 phosphorylation in normoxia and, to a lesser extent, hypoxia, whereas LN229 cells were unaffected (FIG. 12C), suggesting that PTEN status may differentially affect hypoxia-stimulated mitochondrial Akt-PDK1 signaling depending on the tumor cell type.

To examine a more "physiologic" model of tumor hypoxia, 3D cultures of patient-derived, stem cell-enriched GBM neurospheres were observed (Di Cristofori, A., et al. (2015) Oncotarget 6, 17514-17531). These cultures become hypoxic in their "core", as determined by expression of a hypoxia probe (FIGS. 4A and 12D and 12E). Under these conditions, GBM neurospheres exhibited strong phosphorylation of PDK1, as determined by immunofluorescence with pT346 Ab (FIG. 4A). Conversely, differentiated GBM cells depleted of stem cells and growing as monolayers were normoxic, contained cytosolic HIF1α, and did not react with pT346 Ab (FIG. 4A). Pre-absorption of pT346 Ab with the immunizing peptide abolished reactivity with GBM (FIG. 12D).

Next, Akt phosphorylation of PDK1 was observed in primary, patient-derived GBM tissue samples (Table 1 below).

GBMs with a high score (≥2) for nuclear HIF1α showed increased phosphorylation of PDK1 by Akt (pT346 Ab), as well as phosphorylation of PDHE1 and Src, a major determinant of glioma invasiveness (Du (2009) Nat Biotechnol 27, 77-83.), in hypoxic areas (FIGS. 4B and S4F). In contrast, GBMs with undetectable nuclear HIF1α (score=0) showed low to undetectable levels of PDK1-PDHE1 phosphorylation (FIGS. 4C and S4F). In these patients, phosphorylation of PDK1 (pT346 Ab) (FIG. 4D) or PDHE1 phosphorylation (FIG. 4E) correlated with expression of nuclear HIF1α. Reciprocally, PDHE1 phosphorylation correlated with the expression of Akt-phosphorylated PDK1 (pT346 Ab) (FIG. 4F), reinforcing a link between hypoxia and mitochondrial Akt-PDK1 phosphorylation in primary patient samples.

Example 6: Mitochondrial Akt-PDK1 Regulation of Tumor Cell Proliferation in Hypoxia To test a role of a mitochondrial Akt-PDK1 signaling in tumor growth in vivo, human U251 GBM cells expressing a luciferase reporter under the control of a HIF1-responsive element (HRE) and a mCherry reporter under a constitutive PGK promoter was observed to quantify cell viability. Stereotactic intracranial injection of these cells in immunocompromised mice gave rise to GBMs characterized by HIF1-directed luciferase activity and reactivity with a hypoxia-sensitive marker (FIGS. 5A and 5B). Despite low oxygenation, these orthotopic GBMs remained viable, as determined by high mCherry expression (FIGS. 5A and 5B) and exhibited a time-dependent increase in the number of mitotic tumor cells (FIG. 13A). These proliferating cells stained intensely positive for Akt-phosphorylated PDK1 (FIGS. 5C and 13B and 13C), correlating with increased HIF1 activity (FIG. 13D). PDHE1 was also highly phosphorylated in intracranial GBMs (FIG. 5C).

The requirement of mitochondrial Akt-PDK1 signaling in regulating proliferation under hypoxic conditions was observed. siRNA knockdown of Akt1 or Akt2 (FIG. 5D) or stable shRNA knockdown of PDK1 (FIG. 5E) suppressed tumor cell proliferation in hypoxia. Normoxic cultures were partially affected (FIGS. 5D and 5E). When cells were analyzed for cell cycle transitions, MK2206 or the PDK1 inhibitor dichloroacetate (DCA) suppressed S-phase progression in hypoxia and increased the population of tumor cells in G1/sub-G1 phase (FIG. 13E). Finally, stable silencing of PDK1 abolished PC3 colony formation in hypoxia, a marker of tumorigenicity (FIGS. 5F and 5G), whereas normoxic growth was not significantly affected. Together, these data point to an important role of mitochondrial Akt-PDK1 signaling in maintaining tumor cell proliferation in hypoxia.

Example 7: Mitochondrial Akt Regulation of Stress Signaling in Hypoxia

The downstream implications of defective mitochondrial Akt-PDK1 signaling were next investigated. First, inhibition of Akt with MK2206 (FIG. 6A) or stable shRNA silencing of PDK1 (FIG. 6B) increased aberrant ROS production in tumor cells, especially in hypoxia. This was associated with decreased tumor cell viability (FIG. 6C), and appearance of cleaved caspase 3 (FIG. 6D), a marker of apoptosis. In normoxia, cleaved caspase 3 was undetectable. Confirming the specificity of this response, exposure of tumor cells to a small molecule inhibitor of PI3K, PX-866 did not result in caspase activation (FIG. 6D). Reconstitution of these cells with WT PDK1, but not T346A PDK1 mutant, partially rescued tumor cell viability in hypoxia (FIG. 6E). Normoxic cultures were not affected, further supporting a role of PDK1 signaling selectively in hypoxia.

As a second downstream pathway of tumor maintenance modulated by bioenergetics, stable knockdown of PDK1 (FIG. 6F) or siRNA silencing of Akt1 or Akt2 (FIG. 6G) in hypoxia increased the phosphorylation of the energy stress sensor, AMP-regulated kinase (AMPK). This response was associated with concomitant activation of autophagy, as determined by LC3 conversion to a lipidated form (FIGS. 6F and 6G), and punctate LC3 fluorescence staining (FIGS. 6H and 6I). Normoxic cultures showed a minimal level of autophagy induction after PDK1 silencing (FIGS. 6F and 6G and 14A). In PDK1-depleted cells, re-expression of WT PDK1, but not T346A PDK1 mutant, attenuated AMPK phosphorylation and reduced autophagy in hypoxia (FIGS. 6H and 6I and 14B).

Example 8: Requirement of Hypoxic Mitochondrial Reprogramming for Tumor Growth In Vivo Next, the question was if mitochondrial Akt-PDK1 signaling was important for tumor growth in vivo. shRNA silencing of PDK1 significantly impaired the growth of PC3 xenograft tumors implanted in immunocompromised mice (FIG. 7A). Re-expression of WT PDK1 in these cells restored tumor growth in vivo (FIGS. 7B and 7C), whereas T346A PDK1 mutant further impaired tumor growth (FIG. 7C). By immunohistochemistry, PC3 tumors harboring WT PDK1 showed increased cell proliferation, reduced apoptosis and lower levels of autophagy, compared to tumors reconstituted with T346A PDK1 mutant (FIGS. 7D and 7E). In addition, tumors with loss of endogenous PDK1 showed a trend towards increased apoptosis and heightened autophagy in vivo, whereas tumor cell proliferation by Ki-67 staining was unchanged (FIGS. 7F and G). Taken together, these results suggest that mitochondrial Akt-PDK1 signaling promotes tumor adaptation to hypoxia, and specifically enables continued tumor cell proliferation despite an unfavorable microenvironment (FIG. 7H).

To test the relevance of this model in human cancer, the prognostic impact of Akt phosphorylation of PDK1 was observed in a clinically-annotated cohort of 116 glioma patients (Table 3 below).

TABLE 3

Clinico-pathological and molecular characteristics of the second cohort of glioma patients used for prognostic analysis of pPDK1 (T346) and patients' survival (n = 116).

| Grade | Tumor type (abbreviation) | n | Age[1] | Gender M/F | MGMT methylated cases (n, %) | IDH1$^{R132H}$ (n, %) |
|---|---|---|---|---|---|---|
| Grade II (n = 36) | Astrocytoma (Astr) | 7 | 50 [23-76] | 5M/2F | 5 (71%) | 4 (57%) |
| | Oligodendroglioma (OD) | 29 | 48 [31-71] | 17M/12F | 23 (79%) | 19 (66%) |
| Grade III (n = 11) | Anaplastic Astrocytoma (AA) | 15 | 58 [35-70] | 9M/6F | 9 (60%) | 5 (30%) |
| | Anaplastic Oligodendroglioma (AO) | 4 | 50 [42-60] | 2M/2F | 4 (100%) | 3 (75%) |
| Grade IV | Glioblastoma (GBM) | 61 | 55 [24-82] | 38M/23F | 31 (51%) | 9 (15%) |

[1]Mean patient age at diagnosis in years with range is provided

Undetectable in normal brain parenchyma, the expression of Akt phosphorylated PDK1 on T346 progressively increased in gliomas, with the highest reactivity observed in glioblastoma (FIGS. 8A and 8B). PDK1 phosphorylation on T346 segregated with other markers of disease progression, including HIF1α expression (FIG. 8C), wild type status of isocitrate dehydrogenase-1 (IDH1) (FIG. 8D), and unmethylated MGMT promoter (FIG. 8E). Consistent with this prognostic profile, elevated expression of Akt-phosphorylated PDK1, as determined by ROC curves analysis (FIGS. 15A and 15B), was significantly associated with reduced overall survival in patients with gliomas (p=0.006; HR=2.2; 95% CI: 1.17-4.12; FIG. 8F) as well as patients with GBM (p=0.032; HR=2.03; 95% CI: 0.95-4.32; FIG. 8G).

There have accordingly been discussed above a number of embodiments and illustrative examples according to the present invention. Additional variations and modifications of those embodiments and examples in accordance with the invention will be apparent in addition to those specifically set forth above. Accordingly, it is to be understood that the above disclosure of the invention is not limiting but is set forth in order to facilitate an understanding of the invention. The scope of the invention including modifications and additions as noted above is also not limited by the following appended claims.

The invention claimed is:

1. A method of treating cancer in a human subject in which cancer cells express Pyruvate Dehydrogenase Kinase-1 (PDK1) that is phosphorylated at T346 (pT346 PDK1), the method comprising the steps of isolating a biological sample from the human subject and detecting pT346 PDK1 in the biological sample, and administering a therapeutically effective dose of a PDK1 inhibitor and/or an Protein Kinase B-beta (AKT) inhibitor to the human subject.

2. The method according to claim 1, wherein the cancer is a hypoxic tumor.

3. The method according to claim 1, wherein the cancer is selected from the group consisting of glioma, prostate cancer and breast cancer.

4. The method according to claim 1, wherein the pT346 PDK1 in the biological sample is compared to a level of pT346 PDK in normoxic cells.

5. The method according to claim 1, wherein the biological sample is a tissue biopsy or blood sample.

6. The method according to claim 1, wherein the method comprises administering the PDK1 and the AKT inhibitor to the human subject.

7. The method according to claim 1, wherein the PDK1 inhibitor is selected from the group consisting of:

4-[3-chloro-4-[[(2R)-3,3,3-trifluoro-2-hydroxy-2-methyl-propanoyl]amino]phenyl]sulfonyl-N,N-dimethylbenzamide (AZD7545);

sodium dichloroacetate (Ceresine);

6,8-bis(benzylsulfanyl)octanoic acid (CPI613);

lipoic acid; and

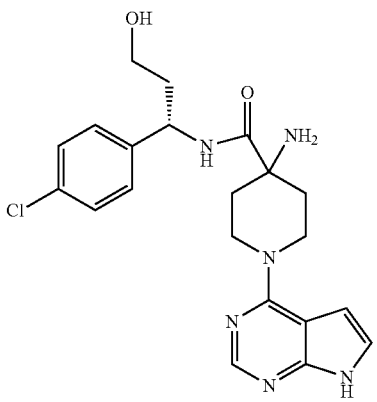 [SMILES: NC1(C(=O)N[C@@H](CCO)c2ccc(Cl)cc2)CCN(c2ncnc3[nH]ccc23)CC1]

4-amino-N-[(1S)-1-(4-chlorophenyl)-3-hydroxypropyl]-1-(7H-pyrrolo[2,3-d]pyrimidin-4-yl)piperidine-4-carboxamide (AZD5363).

8. The method according to claim 1, wherein the AKT inhibitor is selected from the group consisting of:

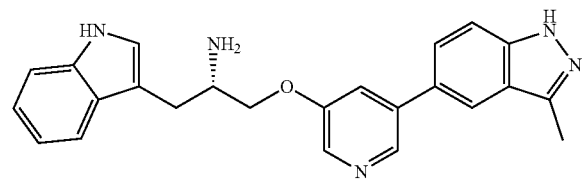 [SMILES: Cc1n[nH]c2ccc(-c3cncc(OC[C@@H](N)Cc4c[nH]c5ccccc45)c3)cc12]

(2s)-1-(1h-Indol-3-Yl)-3-{[5-(3-Methyl-1h-Indazol-5-Yl)pyridin-3-Yl]oxy}propan-2-Amine (A443654);
5-{5-[(2S)-2-amino-3-(1H-indol-3-yl)propoxy]pyridin-3-yl}-3-methyl-1H-indazole;
6-(4-(1-aminocyclobutyl)phenyl)-1-methyl-7-phenyl-1H-pyrido[2,3-b][1,4]oxazin-2(3H)-one  2-(6-(4-(1-aminocyclobutyl)phenyl)-2-oxo-7-phenyl-2,3-dihydro-1H-pyrido[2-,3-b][1,4]oxazin-1yl)acetonitrile;
2-(6-(4-(1-aminocyclobutyl)phenyl)-2-oxo-7-phenyl-2,3-dihydro-1H-pyrido[2-,3-b][1,4]oxazin-1yl)acetonitrile;

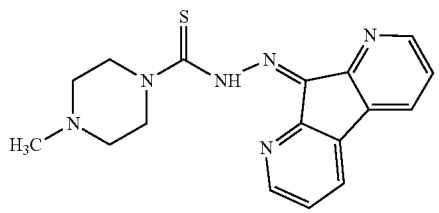 [SMILES: CN1CCN(C(=S)NN=C2c3ncccc3-c3cccnc32)CC1]

3-(3-(4-(1-aminocyclobutyl)phenyl)-5-phenyl-3H-imidazo[4,5-b]pyridin-2-yl)pyridin-2-amine;

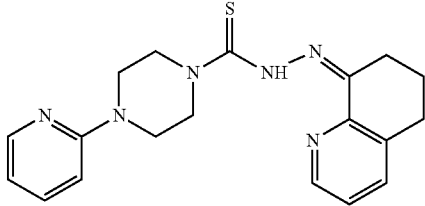 [SMILES: S=C(N/N=C1/CCCc2cccnc21)N1CCN(c2ccccn2)CC1]

N'-(9H-cyclopenta[1,2-b:4,3-b']dipyridin-9-ylidene)-4-methylpiperazine-1-carbothiohydrazide; and

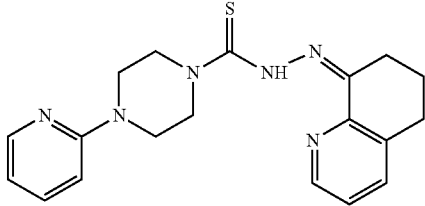 [SMILES: S=C(N/N=C1/CCCc2cccnc21)N1CCN(c2ccccn2)CC1]

(Z)—N'-(6,7-dihydroquinolin-8(5H)-ylidene)-4-(pyridin-2-yl)piperazine-1-carbothiohydrazide.

\* \* \* \* \*

SEQUENCE LISTING

```
<160> NUMBER OF SEQ ID NOS: 10

<210> SEQ ID NO 1
<211> LENGTH: 436
<212> TYPE: PRT
<213> ORGANISM: Artificial Sequence
<220> FEATURE:
<223> OTHER INFORMATION: human PDK1

<400> SEQUENCE: 1

Met Arg Leu Ala Arg Leu Leu Arg Gly Ala Ala Leu Ala Gly Pro Gly
1               5                   10                  15

Pro Gly Leu Arg Ala Ala Gly Phe Ser Arg Ser Phe Ser Ser Asp Ser
            20                  25                  30

Gly Ser Ser Pro Ala Ser Glu Arg Gly Val Pro Gly Gln Val Asp Phe
        35                  40                  45

Tyr Ala Arg Phe Ser Pro Ser Pro Leu Ser Met Lys Gln Phe Leu Asp
    50                  55                  60

Phe Gly Ser Val Asn Ala Cys Glu Lys Thr Ser Phe Met Phe Leu Arg
65                  70                  75                  80

Gln Glu Leu Pro Val Arg Leu Ala Asn Ile Met Lys Glu Ile Ser Leu
                85                  90                  95

Leu Pro Asp Asn Leu Leu Arg Thr Pro Ser Val Gln Leu Val Gln Ser
            100                 105                 110

Trp Tyr Ile Gln Ser Leu Gln Glu Leu Leu Asp Phe Lys Asp Lys Ser
        115                 120                 125

Ala Glu Asp Ala Lys Ala Ile Tyr Asp Phe Thr Asp Thr Val Ile Arg
    130                 135                 140
```

```
Ile Arg Asn Arg His Asn Asp Val Ile Pro Thr Met Ala Gln Gly Val
145                 150                 155                 160

Ile Glu Tyr Lys Glu Ser Phe Gly Val Asp Pro Val Thr Ser Gln Asn
            165                 170                 175

Val Gln Tyr Phe Leu Asp Arg Phe Tyr Met Ser Arg Ile Ser Ile Arg
        180                 185                 190

Met Leu Leu Asn Gln His Ser Leu Leu Phe Gly Gly Lys Gly Lys Gly
            195                 200                 205

Ser Pro Ser His Arg Lys His Ile Gly Ser Ile Asn Pro Asn Cys Asn
        210                 215                 220

Val Leu Glu Val Ile Lys Asp Gly Tyr Glu Asn Ala Arg Arg Leu Cys
225                 230                 235                 240

Asp Leu Tyr Tyr Ile Asn Ser Pro Glu Leu Glu Leu Glu Leu Asn
            245                 250                 255

Ala Lys Ser Pro Gly Gln Pro Ile Gln Val Val Tyr Val Pro Ser His
            260                 265                 270

Leu Tyr His Met Val Phe Glu Leu Phe Lys Asn Ala Met Arg Ala Thr
            275                 280                 285

Met Glu His His Ala Asn Arg Gly Val Tyr Pro Pro Ile Gln Val His
            290                 295                 300

Val Thr Leu Gly Asn Glu Asp Leu Thr Val Lys Met Ser Asp Arg Gly
305                 310                 315                 320

Gly Gly Val Pro Leu Arg Lys Ile Asp Arg Leu Phe Asn Tyr Met Tyr
                325                 330                 335

Ser Thr Ala Pro Arg Pro Arg Val Glu Thr Ser Arg Ala Val Pro Leu
            340                 345                 350

Ala Gly Phe Gly Tyr Gly Leu Pro Ile Ser Arg Leu Tyr Ala Gln Tyr
            355                 360                 365

Phe Gln Gly Asp Leu Lys Leu Tyr Ser Leu Glu Gly Tyr Gly Thr Asp
            370                 375                 380

Ala Val Ile Tyr Ile Lys Ala Leu Ser Thr Asp Ser Ile Glu Arg Leu
385                 390                 395                 400

Pro Val Tyr Asn Lys Ala Ala Trp Lys His Tyr Asn Thr Asn His Glu
                405                 410                 415

Ala Asp Asp Trp Cys Val Pro Ser Arg Glu Pro Lys Asp Met Thr Thr
                420                 425                 430

Phe Arg Ser Ala
        435

<210> SEQ ID NO 2
<211> LENGTH: 16
<212> TYPE: PRT
<213> ORGANISM: Artificial Sequence
<220> FEATURE:
<223> OTHER INFORMATION: PDK1 phosphorylated T346 chymotryptic peptide
<220> FEATURE:
<221> NAME/KEY: MISC_FEATURE
<222> LOCATION: (10)..(10)
<223> OTHER INFORMATION: phosphorylation

<400> SEQUENCE: 2

Ser Thr Ala Pro Arg Pro Arg Val Glu Thr Ser Arg Ala Val Pro Leu
1               5                   10                  15

<210> SEQ ID NO 3
<211> LENGTH: 14
<212> TYPE: PRT
```

```
<213> ORGANISM: Artificial Sequence
<220> FEATURE:
<223> OTHER INFORMATION: PDK1 non-phosphorylated T346 chymotryptic
      peptide

<400> SEQUENCE: 3

Ala Pro Arg Pro Arg Val Glu Thr Ser Arg Ala Val Pro Leu
1               5                   10

<210> SEQ ID NO 4
<211> LENGTH: 21
<212> TYPE: DNA
<213> ORGANISM: Artificial Sequence
<220> FEATURE:
<223> OTHER INFORMATION: human PDK1

<400> SEQUENCE: 4
cgtgaatatg ttgaagtaga a                                              21

<210> SEQ ID NO 5
<211> LENGTH: 16
<212> TYPE: PRT
<213> ORGANISM: Artificial Sequence
<220> FEATURE:
<223> OTHER INFORMATION: phosphorylated PDK1 peptide
<220> FEATURE:
<221> NAME/KEY: MISC_FEATURE
<222> LOCATION: (9)..(9)
<223> OTHER INFORMATION: phosphorylated

<400> SEQUENCE: 5

Cys Ala Pro Arg Pro Arg Val Glu Thr Ser Arg Ala Val Pro Leu Ala
1               5                   10                  15

<210> SEQ ID NO 6
<211> LENGTH: 21
<212> TYPE: PRT
<213> ORGANISM: Artificial Sequence
<220> FEATURE:
<223> OTHER INFORMATION: PDK1

<400> SEQUENCE: 6

Tyr Ser Thr Ala Pro Arg Pro Arg Val Glu Thr Ser Arg Ala Val Pro
1               5                   10                  15

Leu Ala Gly Phe Gly
            20

<210> SEQ ID NO 7
<211> LENGTH: 20
<212> TYPE: PRT
<213> ORGANISM: Artificial Sequence
<220> FEATURE:
<223> OTHER INFORMATION: PDK2

<400> SEQUENCE: 7

Tyr Ser Thr Ala Pro Thr Pro Gln Pro Gly Thr Gly Gly Thr Pro Leu
1               5                   10                  15

Ala Gly Phe Gly
            20

<210> SEQ ID NO 8
<211> LENGTH: 21
<212> TYPE: PRT
<213> ORGANISM: Artificial Sequence
<220> FEATURE:
<223> OTHER INFORMATION: PDK2
```

```
<400> SEQUENCE: 8

Tyr Ser Thr Ala Pro Arg Pro Ser Leu Glu Pro Thr Arg Ala Ala Pro
1               5                   10                  15

Leu Ala Gly Phe Gly
            20

<210> SEQ ID NO 9
<211> LENGTH: 21
<212> TYPE: PRT
<213> ORGANISM: Artificial Sequence
<220> FEATURE:
<223> OTHER INFORMATION: PDK4

<400> SEQUENCE: 9

Tyr Ser Thr Ala Pro Thr Pro Val Met Asp Asn Ser Arg Asn Ala Pro
1               5                   10                  15

Leu Ala Gly Phe Gly
            20

<210> SEQ ID NO 10
<211> LENGTH: 15
<212> TYPE: PRT
<213> ORGANISM: Artificial Sequence
<220> FEATURE:
<223> OTHER INFORMATION: PDK1

<400> SEQUENCE: 10

Ala Pro Arg Pro Arg Val Glu Thr Ser Arg Ala Val Pro Leu Ala
1               5                   10                  15
```